US011312968B2

(12) United States Patent
Dai et al.

(10) Patent No.: US 11,312,968 B2
(45) Date of Patent: Apr. 26, 2022

(54) YEAST STRAINS AND METHODS FOR PRODUCING COLLAGEN

(71) Applicant: MODERN MEADOW, INC., Brooklyn, NY (US)

(72) Inventors: Lixin Dai, Livingston, NJ (US); Julia Borden, San Mateo, CA (US); Jeffrey Nelson, Brooklyn, NY (US); Kristin Ruebling-Jass, Union, NJ (US)

(73) Assignee: MODERN MEADOW, INC., Nutley, NJ (US)

( * ) Notice: Subject to any disclaimer, the term of this patent is extended or adjusted under 35 U.S.C. 154(b) by 182 days.

(21) Appl. No.: 16/023,525

(22) Filed: Jun. 29, 2018

(65) Prior Publication Data

US 2019/0002893 A1 Jan. 3, 2019

Related U.S. Application Data

(60) Provisional application No. 62/526,912, filed on Jun. 29, 2017.

(51) Int. Cl.

| | |
|---|---|
| ***C12Q 1/68*** | (2018.01) |
| ***C12N 15/81*** | (2006.01) |
| ***C07K 14/78*** | (2006.01) |
| ***C12P 21/02*** | (2006.01) |
| ***C08J 3/24*** | (2006.01) |
| ***C12N 1/16*** | (2006.01) |
| ***C12N 1/18*** | (2006.01) |
| ***C12R 1/72*** | (2006.01) |
| ***C12R 1/78*** | (2006.01) |
| ***C12R 1/84*** | (2006.01) |
| ***C12R 1/85*** | (2006.01) |
| ***D01F 4/00*** | (2006.01) |
| ***D06N 3/00*** | (2006.01) |
| ***C12N 9/02*** | (2006.01) |
| *C12N 15/10* | (2006.01) |

(52) U.S. Cl.

CPC .............. *C12N 15/81* (2013.01); *C07K 14/78* (2013.01); *C12N 9/0071* (2013.01); *C12P 21/02* (2013.01); *D01F 4/00* (2013.01); *D06N 3/00* (2013.01); *C08J 3/24* (2013.01); *C12N 1/165* (2021.05); *C12N 1/185* (2021.05); *C12R 2001/72* (2021.05); *C12R 2001/78* (2021.05); *C12R 2001/84* (2021.05); *C12R 2001/85* (2021.05)

(58) Field of Classification Search

CPC ...................................................... C12N 15/81

See application file for complete search history.

(56) References Cited

U.S. PATENT DOCUMENTS

| | | | | |
|---|---|---|---|---|
| 6,428,978 | B1 | 8/2002 | Olsen et al. | |
| 6,451,557 | B1 | 9/2002 | Vaughan et al. | |
| 6,472,171 | B1 | 10/2002 | Toman et al. | |
| 6,992,172 | B1 | 1/2006 | Chang et al. | |
| 8,188,230 | B2 | 5/2012 | Van Heerde et al. | |
| 10,301,440 | B2 | 5/2019 | Purcell et al. | |
| 10,370,504 | B2 | 8/2019 | Purcell et al. | |
| 10,370,505 | B2 | 8/2019 | Purcell et al. | |
| 10,519,285 | B2 | 12/2019 | Purcell et al. | |
| 2008/0139477 | A1 | 6/2008 | Vaughan et al. | |
| 2015/0011407 | A1 | 1/2015 | Vogl et al. | |
| 2016/0046692 | A1 * | 2/2016 | Ramshaw | C07K 14/195 530/356 |
| 2017/0233536 | A1 | 8/2017 | Purcell et al. | |
| 2017/0233537 | A1 | 8/2017 | Purcell et al. | |
| 2017/0233943 | A1 | 8/2017 | Purcell et al. | |
| 2017/0233944 | A1 | 8/2017 | Purcell et al. | |
| 2019/0040400 | A1 | 2/2019 | Dai et al. | |
| 2019/0092838 | A1 | 3/2019 | Dai et al. | |
| 2019/0093116 | A1 | 3/2019 | Dai et al. | |

FOREIGN PATENT DOCUMENTS

| | | | | |
|---|---|---|---|---|
| CN | 106256911 | A | 12/2016 | |
| EP | 1 232 182 | A2 | 8/2002 | |
| EP | 1232182 | B1 | 10/2007 | |
| EP | 2 862 933 | A2 | 4/2015 | |
| WO | WO 97/14431 | A1 | 4/1997 | |
| WO | WO 98/18918 | A1 | 5/1998 | |
| WO | WO-0134647 | A2 * | 5/2001 | C12N 15/8257 |
| WO | WO-2014170460 | A2 * | 10/2014 | C07K 14/43504 |
| WO | WO 2019/060672 | A1 | 3/2019 | |

OTHER PUBLICATIONS

Gustafsson et al., Trends in Biotech., 22, 7, 346-353, (Year: 2004).*
Sinclair et al., Protein Exp. and Purif., 26, 96-105 (Year: 2005).*
Sinclair et. al. 2002. Synonymous codon usage bias and the expression of human glucocerebrosidase in the methylotrophic yeast, Pichia pastoris. Protein Exp. And Purif., 26, 96-105 (Year: 2002).*
Nokelainen. Recombinant Human Collagens: Characterization of type II collagen expressed in insect cells and production of types 1-111 collagen in yeast *Pichia pastoris*, Department of Medical Biochemistry, University of Oulu 2000: pp. 1-72 (Year: 2000).*
Extended European Search Report dated Mar. 26, 2019 in Patent Application No. 18180892.4. citing documents AA-AE, AO-AS, and AX therein, 10 pages.
Wells, H.C. et al. "Collagen Fibril Diameter and Leather Strength" Journal of Agricultural and Food Chemistry, vol. 61, No. 47, XP055387091, 2013, pp. 11524-11531.

(Continued)

*Primary Examiner* — Nancy J Leith
*Assistant Examiner* — Tiffany Nicole Grooms
(74) *Attorney, Agent, or Firm* — Sterne, Kessler, Goldstein & Fox P.L.L.C.

(57) ABSTRACT

Strains of yeast genetically engineered to produce increased amounts of non-hydroxylated collagen or hydroxylated collagen are described. An all-in-one vector including the DNA necessary to produce collagen, promotors, and hydroxylating enzymes is also described. Methods for producing non-hydroxylated or hydroxylated collagen are also provided.

33 Claims, 12 Drawing Sheets

Specification includes a Sequence Listing.

(56) References Cited

OTHER PUBLICATIONS

Collagen alpha-1(I) chain precursor [Bos Taurus], NCBI Reference Sequesnce: NP 001029211.1 *available at* https:// www.ncbi.nlm.nih.gov/protein/77404252 (accessed on Dec. 18, 2019).

Collagen alpha-2(I) chain precursor [Bos taurus], NCBI Reference Sequence: NP_776945.1, available at https://www.ncbi.nlm.nih.gov/protein/27806257 last accessed Dec. 19, 2019).

Collagen alpha-1(III) chain precursor [Bos taurus], NCBI Reference Sequence: NP 001070299.1, available at https://www.ncbi.nlm.nih.gov/protein/116003881 last accessed Dec. 19, 2019.

* cited by examiner

YEAST STRAINS AND METHODS FOR PRODUCING COLLAGEN

CROSS REFERENCE TO RELATED APPLICATIONS

This application is related to U.S. Patent Application No. 62/526,912 filed Jun. 29, 2017, the entire contents of which are incorporated by reference.

REFERENCE TO SEQUENCE LISTING SUBMITTED ELECTRONICALLY

The content of the electronically submitted sequence listing in ASCII text file (Name 4431_0120002_Seg-listingST25; Size: 165,817 bytes; and Date of Creation: Jun. 15, 2021) filed with the application is incorporated herein by reference in its entirety.

BACKGROUND OF THE INVENTION

Field of the Invention

This invention relates to genetically engineered strains of yeast and methods for producing collagen. The strains are engineered to increase the amount of collagen produced and improve the stability of collagen produced. The collagen may be useful for the production of bio fabricated leather materials and the like.

Description of Related Art

Leather.

Leather is used in a vast variety of applications, including furniture upholstery, clothing, shoes, luggage, handbag and accessories, and automotive applications. The estimated global trade value in leather is approximately US $100 billion per year (*Future Trends in the World Leather Products Industry and Trade*, United Nations Industrial Development Organization, Vienna, 2010) and there is a continuing and increasing demand for leather products. New ways to meet this demand are required in view of the economic, environmental and social costs of producing leather. To keep up with technological and aesthetic trends, producers and users of leather products seek new materials exhibiting superior strength, uniformity, processability and fashionable and appealing aesthetic properties that incorporate natural components.

Given population growth and the global environment, there will be a need for alternative materials that have leather-like aesthetics and improved functionalities. Leather is animal hide and consists almost entirely of collagen. There is a need for a source of collagen that can be converted to bio fabricated leather materials.

Collagen.

Collagen is the main component of leather. Skin, or animal hide, contains significant amounts of collagen, a fibrous protein. Collagen is a generic term for a family of at least 28 distinct collagen types; animal skin is typically Type I collagen, although other types of collagen can be used in forming leather including type III collagen.

Collagens are characterized by a repeating triplet of amino acids, $-(Gly-X-Y)_n-$ and approximately one-third of the amino acid residues in collagen are glycine. X is often proline and Y is often hydroxyproline, though there may be up to 400 possible Gly-X-Y triplets. Different animals may produce different amino acid compositions of the collagen, which may result in different properties and in differences in the resulting leather.

The structure of collagen can consist of three intertwined peptide chains of differing lengths. Collagen triple helices (or monomers) may be produced from alpha-chains of about 1,050 amino acids long, so that the triple helix takes the form of a rod of about approximately 300 nm long, with a diameter of approximately 1.5 nm.

Collagen fibers may have a range of diameters depending on the type of animal hide. In addition to type I collagen, skin (hides) may include other types of collagen as well, including type III collagen (reticulin), type IV collagen, and type VII collagen.

Various types of collagen exist throughout the mammalian body. For example, besides being the main component of skin and animal hide, Type I collagen also exists in cartilage, tendon, vascular ligature, organs, muscle, and the organic portion of bone. Successful efforts have been made to isolate collagen from various regions of the mammalian body in addition to the animal skin or hide. Decades ago, researchers found that at neutral pH, acid-solubilized collagen self-assembled into fibrils composed of the same cross-striated patterns observed in native tissue; Schmitt F. O. J. Cell. Comp Physiol. 1942; 20:11). This led to use of collagen in tissue engineering and a variety of biomedical applications. In more recent years, collagen has been harvested from bacteria and yeast using recombinant techniques.

Regardless of the type of collagen, all are formed and stabilized through a combination of physical and chemical interactions including electrostatic interactions including salt bridging, hydrogen bonding, Van der Waals interactions, dipole-dipole forces, polarization forces, hydrophobic interactions, and covalent bonding often catalyzed by enzymatic reactions. For Type I collagen fibrils, fibers, and fiber bundles, its complex assembly is achieved in vivo during development and is critical in providing mechanical support to the tissue while allowing for cellular motility and nutrient transport. Various distinct collagen types have been identified in vertebrates. These include bovine, ovine, porcine, chicken, and human collagens.

Generally, the collagen types are numbered by Roman numerals, and the chains found in each collagen type are identified by Arabic numerals. Detailed descriptions of structure and biological functions of the various different types of naturally occurring collagens are available in the art; see, e.g., Ayad et al. (1998) The Extracellular Matrix Facts Book, Academic Press, San Diego, Calif.; Burgeson, R E., and Nimmi (1992) "Collagen types: Molecular Structure and Tissue Distribution" in Clin. Orthop. 282:250-272; Kielty, C. M. et al. (1993) "The Collagen Family: Structure, Assembly And Organization In The Extracellular Matrix," Connective Tissue And Its Heritable Disorders, Molecular Genetics, And Medical Aspects, Royce, P. M. and B. Steinmann eds., Wiley-Liss, NY, pp. 103-147; and Prockop, D. J- and K. I. Kivirikko (1995) "Collagens: Molecular Biology, Diseases, and Potentials for Therapy," Annu. Rev. Biochem., 64:403-434.)

Type I collagen is the major fibrillar collagen of bone and skin comprising approximately 80-90% of an organism's total collagen. Type I collagen is the major structural macromolecule present in the extracellular matrix of multicellular organisms and comprises approximately 20% of total protein mass. Type I collagen is a heterotrimeric molecule comprising two $\alpha1(I)$ chains and one $\alpha2(I)$ chain, encoded by the COL1A1 and COL1A2 genes, respectively. Other collagen types are less abundant than type I collagen, and exhibit different distribution patterns. For example, type II collagen is the predominant collagen in cartilage and vitreous humor, while type III collagen is found at high levels in blood vessels and to a lesser extent in skin.

Type II collagen is a homotrimeric collagen comprising three identical a1(II) chains encoded by the COL2A1 gene. Purified type II collagen may be prepared from tissues by, methods known in the art, for example, by procedures described in Miller and Rhodes (1982) Methods In Enzymology 82:33-64.

Type III collagen is a major fibrillar collagen found in skin and vascular tissues. Type III collagen is a homotrimeric collagen comprising three identical α1(III) chains encoded by the COL3A1 gene. Methods for purifying type III collagen from tissues can be found in, for example, Byers et al. (1974) Biochemistry 13:5243-5248; and Miller and Rhodes, supra.

Type IV collagen is found in basement membranes in the form of sheets rather than fibrils. Most commonly, type IV collagen contains two α1(IV) chains and one α2(IV) chain. The particular chains comprising type IV collagen are tissue-specific. Type IV collagen may be purified using, for example, the procedures described in Furuto and Miller (1987) Methods in Enzymology, 144:41-61, Academic Press.

Type V collagen is a fibrillar collagen found in, primarily, bones, tendon, cornea, skin, and blood vessels. Type V collagen exists in both homotrimeric and heterotrimeric forms. One form of type V collagen is a heterotrimer of two α1(V) chains and one α2(V) chain. Another form of type V collagen is a heterotrimer of α1(V), α2(V), and α3(V) chains. A further form of type V collagen is a homotrimer of α1(V). Methods for isolating type V collagen from natural sources can be found, for example, in Elstow and Weiss (1983) Collagen Rel. Res. 3:181-193, and Abedin et al. (1982) Biosci. Rep. 2:493-502.

Type VI collagen has a small triple helical region and two large non-collagenous remainder portions. Type VI collagen is a heterotrimer comprising α1(VI), α2(VI), and α3(VI) chains. Type VI collagen is found in many connective tissues. Descriptions of how to purify type VI collagen from natural sources can be found, for example, in Wu et al. (1987) Biochem. J. 248:373-381, and Kielty et al. (1991) J. Cell Sci. 99:797-807.

Type VII collagen is a fibrillar collagen found in particular epithelial tissues. Type VII collagen is a homotrimeric molecule of three α1(VII) chains. Descriptions of how to purify type VII collagen from tissue can be found in, for example, Lunstrum et al. (1986) J. Biol. Chem. 261:9042-9048, and Bentz et al. (1983) Proc. Natl. Acad. Sci. USA 80:3168-3172. Type VIII collagen can be found in Descemet's membrane in the cornea. Type VIII collagen is a heterotrimer comprising two α1(VIII) chains and one α2(VIII) chain, although other chain compositions have been reported. Methods for the purification of type VIII collagen from nature can be found, for example, in Benya and Padilla (1986) J. Biol. Chem. 261:4160-4169, and Kapoor et al. (1986) Biochemistry 25:3930-3937.

Type IX collagen is a fibril-associated collagen found in cartilage and vitreous humor. Type IX collagen is a heterotrimeric molecule comprising α1(IX), α2(IX), and α3(IX) chains. Type IX collagen has been classified as a FACIT (Fibril Associated Collagens with Interrupted Triple Helices) collagen, possessing several triple helical domains separated by non-triple helical domains. Procedures for purifying type IX collagen can be found, for example, in Duance, et al. (1984) Biochem. J. 221:885-889; Ayad et al. (1989) Biochem. J. 262:753-761; and Grant et al. (1988) The Control of Tissue Damage, Glauert, A. M., ed., Elsevier Science Publishers, Amsterdam, pp. 3-28.

Type X collagen is a homotrimeric compound of α1(X) chains. Type X collagen has been isolated from, for example, hypertrophic cartilage found in growth plates; see, e.g., Apte et al. (1992) Eur J Biochem 206 (1):217-24.

Type XI collagen can be found in cartilaginous tissues associated with type II and type IX collagens, and in other locations in the body. Type XI collagen is a heterotrimeric molecule comprising α1(XI), α2(XI), and α3(XI) chains. Methods for purifying type XI collagen can be found, for example, in Grant et al., supra.

Type XII collagen is a FACIT collagen found primarily in association with type I collagen. Type XII collagen is a homotrimeric molecule comprising three α1(XII) chains. Methods for purifying type XII collagen and variants thereof can be found, for example, in Dublet et al. (1989) J. Biol. Chem. 264:13150-13156; Lunstrum et al. (1992) J. Biol. Chem. 267:20087-20092; and Watt et al. (1992) J. Biol. Chem. 267:20093-20099.

Type XIII is a non-fibrillar collagen found, for example, in skin, intestine, bone, cartilage, and striated muscle. A detailed description of type XIII collagen may be found, for example, in Juvonen et al. (1992) J. Biol. Chem. 267: 24700-24707.

Type XIV is a FACIT collagen characterized as a homotrimeric molecule comprising α1(XIV) chains. Methods for isolating type XIV collagen can be found, for example, in Aubert-Foucher et al. (1992) J. Biol. Chem. 267:15759-15764, and Watt et al., supra.

Type XV collagen is homologous in structure to type XVIII collagen. Information about the structure and isolation of natural type XV collagen can be found, for example, in Myers et al. (1992) Proc. Natl. Acad. Sci. USA 89:10144-10148; Huebner et al. (1992) Genomics 14:220-224; Kivirikko et al. (1994) J. Biol. Chem. 269:4773-4779; and Muragaki, J. (1994) Biol. Chem. 264:4042-4046.

Type XVI collagen is a fibril-associated collagen, found, for example, in skin, lung fibroblast, and keratinocytes. Information on the structure of type XVI collagen and the gene encoding type XVI collagen can be found, for example, in Pan et al. (1992) Proc. Natl. Acad. Sci. USA 89:6565-6569; and Yamaguchi et al. (1992) J. Biochem. 112:856-863.

Type XVII collagen is a hemidesmosal transmembrane collagen, also known at the bullous pemphigoid antigen. Information on the structure of type XVII collagen and the gene encoding type XVII collagen can be found, for example, in Li et al. (1993) J. Biol. Chem. 268(12):8825-8834; and McGrath et al. (1995) Nat. Genet. 11(1):83-86.

Type XVIII collagen is similar in structure to type XV collagen and can be isolated from the liver. Descriptions of the structures and isolation of type XVIII collagen from natural sources can be found, for example, in Rehn and Pihlajaniemi (1994) Proc. Natl. Acad. Sci USA 91:4234-4238; Oh et al. (1994) Proc. Natl. Acad. Sci USA 91:4229-4233; Rehn et al. (1994) J. Biol. Chem. 269:13924-13935; and Oh et al. (1994) Genomics 19:494-499.

Type XIX collagen is believed to be another member of the FACIT collagen family, and has been found in mRNA isolated from rhabdomyosarcoma cells. Descriptions of the structures and isolation of type XIX collagen can be found, for example, in Inoguchi et al. (1995) J. Biochem. 117:137-146; Yoshioka et al. (1992) Genomics 13:884-886; and Myers et al., J. Biol. Chem. 289:18549-18557 (1994).

Type XX collagen is a newly found member of the FACIT collagenous family, and has been identified in chick cornea.

(See, e.g., Gordon et al. (1999) FASEB Journal 13:A1119; and Gordon et al. (1998), IOVS 39:S1128.)

Any type of collagen, truncated collagen, unmodified or post-translationally modified, or amino acid sequence-modified collagen that can be fibrillated and crosslinked by the methods described herein can be used to produce a bio fabricated material or bio fabricated leather. Biofabricated leather may contain a substantially homogenous collagen, such as only Type I or Type III collagen or may contain mixtures of 2, 3, 4 or more different kinds of collagens.

Recombinant Collagen.

Recombinant expression of collagen and collagen-like proteins is known by Bell, EP 1232182B1, Bovine collagen and method for producing recombinant gelatin; Olsen, et al., U.S. Pat. No. 6,428,978, Methods for the production of gelatin and fill-length triple helical collagen in recombinant cells; VanHeerde, et al., U.S. Pat. No. 8,188,230, Method for recombinant microorganism expression and isolation of collagen-like polypeptides, the disclosures of which are hereby incorporated by reference. Such recombinant collagens have not been used to produce leather.

Prokaryotic expression. In prokaryotic systems, such as bacterial systems, a number of expression vectors may be advantageously selected depending upon the use intended for the expressed polypeptide. For example, when large quantities of the animal collagens and gelatins of the invention are to be produced, such as for the generation of antibodies, vectors which direct the expression of high levels of fusion protein products that are readily purified may be desirable. Such vectors include, but are not limited to, the *E. coli* expression vector pUR278 (Ruther et al. (1983) EMBO J. 2:1791), in which the coding sequence may be ligated into the vector in frame with the lac Z coding region so that a hybrid AS-lacZ protein is produced; pIN vectors (Inouye et al. (1985) Nucleic Acids Res. 13:3101-3109 and Van Heeke et al. (1989) J. Biol. Chem. 264:5503-5509); and the like, the disclosures of which are hereby incorporated by reference. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety. A recombinant collagen may comprise collagen molecules that have not been post-translationally modified, e.g., not glycosylated or hydroxylated, or may comprise one or more post-translational modifications, for example, modifications that facilitate fibrillation and formation of unbundled and randomly oriented fibrils of collagen molecules.

A recombinant collagen molecule can comprise a fragment of the amino acid sequence of a native collagen molecule that can form trimeric collagen fibrils or a modified collagen molecule or truncated collagen molecule having an amino acid sequence at least 70, 80, 90, 95, 96, 97, 98, or 99% identical or similar to a native collagen amino acid sequence (or to a fibril forming region thereof or to a segment substantially comprising [Gly-X-Y]n), such as those of bovine collagen, described by SEQ ID NOS: 1, 2 or 3 and by amino acid sequences of Col1A1, Col1A2, and Col3A1, described by Accession Nos. NP 001029211.1 fwww.ncbi.nlm.nih.gov/protein/77404252, last accessed Feb. 9, 2017), NP 776945.1 (www.ncbi.nlm.nih.gov/protein/27806257, last accessed Feb. 9, 2017) and NP 001070299.1 (www.ncbi.nlm.nih.gov/protein/116003881, last accessed Feb. 9, 2017) which are incorporated by reference.

Such recombinant or modified collagen molecules will generally comprise the repeated $-(Gly-X-Y)_n-$ sequence described herein.

BLASTN may be used to identify a polynucleotide sequence having at least 70%, 75%, 80%, 85%, 87.5%, 90%, 92.5%, 95%, 97.5%, 98%, or 99% sequence identity to a reference polynucleotide such as a polynucleotide encoding a collagen polypeptide or encoding the amino acid sequences of SEQ ID NOS: 1, 2 or 3. A representative BLAS TN setting optimized to find highly similar sequences uses an Expect Threshold of 10 and a Wordsize of 28, max matches in query range of 0, match/mismatch scores of 1/−2, and linear gap cost. Low complexity regions may be filtered or masked. Default settings of a Standard Nucleotide BLAST are described by and incorporated by reference to blast.ncbi.nlm.nih.gov/Blast.cgi?PROGRAM=blastn& PAGE_TYPE=BlastSearch&LIN K_LOC=blasthome (last accessed Jan. 27, 2017).

BLASTP can be used to identify an amino acid sequence having at least 70%, 75%, 80%, 85%, 87.5%, 90%, 92.5%, 95%, 97.5%, 98%, or 99% sequence identity, or similarity to a reference amino acid, such as a collagen amino acid sequence, using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Other default settings for BLASTP are described by and incorporated by reference to the disclosure available at: blast.ncbi.nlm.nih-.gov/Blast.cgi?PROGRAM=blastp&P AGE_TYPE=BlastSearch&LINK_LOC=blasthome (last accessed Jan. 27, 2017).

Yeast Expression.

Collagen molecules may be produced in a yeast expression system. In yeast, a number of vectors containing constitutive or inducible promoters known in the art may be used; Ausubel et al., supra, Vol. 2, Chapter 13; Grant et al. (1987) Expression and Secretion Vectors for Yeast, in Methods in Enzymology, Ed. Wu & Grossman, Acad. Press, N.Y. 153:516-544; Glover (1986) DNA Cloning, Vol. II, IRL Press, Wash., D.C., Ch. 3; Bitter (1987) Heterologous Gene Expression in Yeast, in Methods in Enzymology, Eds. Berger & Kimmel, Acad. Press, N.Y. 152:673-684; and The Molecular Biology of the Yeast *Saccharomyces*, Eds. Strathern et al., Cold Spring Harbor Press, Vols. I and II (1982), the disclosures of which are hereby incorporated by reference.

Collagen can be expressed using host cells, for example, from the yeast *Saccharomyces cerevisiae*. This particular yeast can be used with any of a large number of expression vectors. Commonly employed expression vectors are shuttle vectors containing the 2P origin of replication for propagation in yeast and the Col E1 origin for *E. coli*, for efficient transcription of the foreign gene. A typical example of such vectors based on 2P plasmids is pWYG4, which has the 2P ORI-STB elements, the GAL1-10 promoter, and the 2P D gene terminator. In this vector, an NcoI cloning site is used to insert the gene for the polypeptide to be expressed, and to provide the ATG start codon. Another expression vector is pWYG7L, which has intact 2αORI, STB, REP1 and REP2, and the GAL1-10 promoter, and uses the FLP terminator. In this vector, the encoding polynucleotide is inserted in the polylinker with its 5' ends at a BamHI or Nco1 site. The vector containing the inserted polynucleotide is transformed into *S. cerevisiae* either after removal of the cell wall to produce spheroplasts that take up DNA on treatment with calcium and polyethylene glycol or by treatment of intact cells with lithium ions.

Alternatively, DNA can be introduced by electroporation. Transformants can be selected, for example, using host yeast cells that are auxotrophic for leucine, tryptophan, uracil, or histidine together with selectable marker genes such as LEU2, TRP1, URA3, HIS3, or LEU2-D.

In one embodiment, polynucleotides encoding collagen are introduced into host cells of the yeast *Pichia*. Species of non-*Saccharomyces* yeast such as *Pichia pastoris* appear to have special advantages in producing high yields of recombinant protein in scaled up procedures. Additionally, a *Pichia* expression kit is available from Invitrogen Corporation (San Diego, Calif.).

There are a number of methanol responsive genes in methylotrophic yeasts such as *Pichia pastoris*, the expression of each being controlled by methanol responsive regulatory regions, also referred to as promoters. Any of such methanol responsive promoters are suitable for use in the practice of the present invention. Examples of specific regulatory regions include the AOX1 promoter, the AOX2 promoter, the dihydroxyacetone synthase (DAS), the P40 promoter, and the promoter for the catalase gene from *P. pastoris*, etc.

The methylotrophic yeast *Hansenula polymorpha* has also been used. Growth on methanol results in the induction of key enzymes of the methanol metabolism, such as MOX (methanol oxidase), DAS (dihydroxyacetone synthase), and FMDH (formate dehydrogenase). These enzymes can constitute up to 30-40% of the total cell protein. The genes encoding MOX, DAS, and FMDH production are controlled by strong promoters induced by growth on methanol and repressed by growth on glucose. Any or all three of these promoters may be used to obtain high-level expression of heterologous genes in *H. polymorpha*. Therefore, in one aspect, a polynucleotide encoding animal collagen or fragments or variants thereof is cloned into an expression vector under the control of an inducible *H. polymorpha* promoter. If secretion of the product is desired, a polynucleotide encoding a signal sequence for secretion in yeast is fused in frame with the polynucleotide. In a further embodiment, the expression vector preferably contains an auxotrophic marker gene, such as URA3 or LEU2, which may be used to complement the deficiency of an auxotrophic host.

The expression vector is then used to transform *H. polymorpha* host cells using techniques known to those of skill in the art. A useful feature of *H. polymorpha* transformation is the spontaneous integration of up to 100 copies of the expression vector into the genome. In most cases, the integrated polynucleotide forms multimers exhibiting a head-to-tail arrangement. The integrated foreign polynucleotide has been shown to be mitotically stable in several recombinant strains, even under non-selective conditions. This phenomena of high copy integration further adds to the high productivity potential of the system.

Fungal Expression.

Filamentous fungi has also been used to produce the present polypeptides. Vectors for expressing and/or secreting recombinant proteins in filamentous fungi are well known, and one of skill in the art could use these vectors to express the recombinant animal collagens of the present invention.

Plant Expression.

An animal collagen has been produced in a plant or plant cells. In cases where plant expression vectors are used, the expression of sequences encoding the collagens of the invention may be driven by any of a number of promoters. For example, viral promoters such as the 35S RNA and 19S RNA promoters of CaMV (Brisson et al. (1984) Nature 310:511-514), or the coat protein promoter of TMV (Takamatsu et al. (1987) EMBO J. 6:307-311) may be used; alternatively, plant promoters such as the small subunit of RUBISCO (Coruzzi et al. (1984) EMBO J. 3:1671-1680; Broglie et al. (1984) Science 224:838-843) or heat shock promoters, e.g., soybean hsp17.5-E or hsp17.3-B (Gurley et al. (1986) Mol. Cell. Biol. 6:559-565) may be used. These constructs can be introduced into plant cells by a variety of methods known to those of skill in the art, such as by using Ti plasmids, Ri plasmids, plant virus vectors, direct DNA transformation, microinjection, electroporation, etc. For reviews of such techniques see, for example, Weissbach & Weissbach, Methods for Plant Molecular Biology, Academic Press, NY, Section VIII, pp. 421-463 (1988); Grierson & Corey, Plant Molecular Biology, 2d Ed., Blackie, London, Ch. 7-9 (1988); Transgenic Plants: A Production System for Industrial and Pharmaceutical Proteins, Owen and Pen eds., John Wiley & Sons, 1996; Transgenic Plants, Galun and Breiman eds, Imperial College Press, 1997; and Applied Plant Biotechnology. Chopra, Malik, and Bhat eds., Science Publishers, Inc., 1999.

Plant cells do not naturally produce sufficient amounts of post-translational enzymes to efficiently produce stable collagen. Therefore, where hydroxylation is desired, plant cells used to express animal collagens are supplemented with the necessary post-translational enzymes to sufficiently produce stable collagen. In a preferred embodiment of the present invention, the post-translational enzyme is prolyl 4-hydroxylase.

Methods of producing the animal collagens in plant systems has been achieved by providing a biomass from plants or plant cells, wherein the plants or plant cells comprise at least one coding sequence is operably linked to a promoter to effect the expression of the polypeptide, and the polypeptide is then extracted from the biomass. Alternatively, the polypeptide can be non-extracted, e.g., expressed into the endosperm.

Plant expression vectors and reporter genes are generally known in the art; see, e.g., Gruber et al. (1993) in *Methods of Plant Molecular Biology and Biotechnology*, CRC Press. Typically, the expression vector comprises a nucleic acid construct generated, for example, recombinantly or synthetically, and comprising a promoter that functions in a plant cell, wherein such promoter is operably linked to a nucleic acid sequence encoding an animal collagen or fragments or variants thereof, or a post-translational enzyme important to the biosynthesis of collagen.

Promoters drive the level of protein expression in plants. To produce a desired level of protein expression in plants, expression may be under the direction of a plant promoter. Promoters suitable for use are generally available in the art; see, e.g., PCT Publication No. WO 91/19806. Examples of promoters that may be used include non-constitutive promoters or constitutive promoters. These promoters include, but are not limited to, the promoter for the small subunit of ribulose-1,5-bis-phosphate carboxylase; promoters from tumor-inducing plasmids of *Agrobacterium tumefaciens*, such as the RUBISCO nopaline synthase (NOS) and octopine synthase promoters; bacterial T-DNA promoters such as mas and ocs promoters; and viral promoters such as the cauliflower mosaic virus (CaMV) 19S and 35S promoters or the figwort mosaic virus 35S promoter.

The polynucleotide sequences can be placed under the transcriptional control of a constitutive promoter, directing expression of the collagen or post-translational enzyme in most tissues of a plant. The polynucleotide sequence is under the control of the cauliflower mosaic virus (CaMV) 35S promoter. The double stranded caulimorvirus family has provided the single most important promoter expression for transgene expression in plants, in particular, the 35S promoter; see, e.g., Kay et al. (1987) Science 236:1299. Additional promoters from this family such as the figwort mosaic virus promoter, etc., have been described in the art, and may also be used; see, e.g., Sanger et al. (1990) Plant Mol. Biol. 14:433-443; Medberry et al. (1992) Plant Cell 4:195-192; and Yin and Beachy (1995) Plant J. 7:969-980.

The promoters used in polynucleotide constructs for expressing collagen may be modified, if desired, to affect their control characteristics. For example, the CaMV promoter may be ligated to the portion of the RUBISCO gene that represses the expression of RUBISCO in the absence of light, to create a promoter which is active in leaves, but not in roots. The resulting chimeric promoter may be used as described herein.

Constitutive plant promoters having general expression properties known in the art may be used with the expression vectors of the present invention. These promoters are abundantly expressed in most plant tissues and include, for example, the actin promoter and the ubiquitin promoter; see, e.g., McElroy et al. (1990) Plant Cell 2:163-171; and Christensen et al. (1992) Plant Mol. Biol. 18:675-689.

Alternatively, the polypeptide may be expressed in a specific tissue, cell type, or under more precise environmental conditions or developmental control. Promoters directing expression in these instances are known as inducible promoters. In the case where a tissue-specific promoter is used, protein expression is particularly high in the tissue from which extraction of the protein is desired. Depending on the desired tissue, expression may be targeted to the endosperm, aleurone layer, embryo (or its parts as scutellum and cotyledons), pericarp, stem, leaves tubers, roots, etc. Examples of known tissue-specific promoters include the tuber-directed class I patatin promoter, the promoters associated with potato tuber ADPGPP genes, the soybean promoter of β-conglycinin (7S protein) which drives seed-directed transcription, and seed-directed promoters from the zein genes of maize endosperm; see, e.g., Bevan et al. (1986) Nucleic Acids Res. 14: 4625-38; Muller et al. (1990) Mol. Gen. Genet. 224:136-46; Bray (1987) Planta 172: 364-370; and Pedersen et al. (1982) Cell 29: 1015-26.

Collagen polypeptides can be produced in seed by way of seed-based production techniques using, for example, canola, corn, soybeans, rice and barley seed. In such a process, for example, the product is recovered during seed germination; see, e.g., PCT Publication Numbers WO 9940210; WO 9916890; WO 9907206; U.S. Pat. Nos. 5,866,121; 5,792,933; and all references cited therein. Promoters that may be used to direct the expression of the polypeptides may be heterologous or non-heterologous. These promoters can also be used to drive expression of antisense nucleic acids to reduce, increase, or alter concentration and composition of the present animal collagens in a desired tissue.

Other modifications that may be made to increase and/or maximize transcription polypeptides in a plant or plant cell are standard and known to those in the art. For example a vector comprising a polynucleotide sequence encoding a recombinant animal collagen, or a fragment or variant thereof, operably linked to a promoter may further comprise at least one factor that modifies the transcription rate of collagen or related post-translational enzymes, including, but not limited to, peptide export signal sequence, codon usage, introns, polyadenylation, and transcription termination sites. Methods of modifying constructs to increase expression levels in plants are generally known in the art; see, e.g. Rogers et al. (1985) J. Biol. Chem. 260:3731; and Cornejo et al. (1993) Plant Mol Biol 23:567-58. In engineering a plant system that affects the rate of transcription of collagens and related post-translational enzymes, various factors known in the art, including regulatory sequences such as positively or negatively acting sequences, enhancers and silencers, as well as chromatin structure can affect the rate of transcription in plants. At least one of these factors may be utilized when expressing a recombinant animal collagen, including but not limited to the collagen types described above.

The vectors comprising polynucleotides will typically comprise a marker gene which confers a selectable phenotype on plant cells. Usually, the selectable marker gene will encode antibiotic resistance, with suitable genes including at least one set of genes coding for resistance to the antibiotic spectinomycin, the streptomycin phophotransferase (SPT) gene coding for streptomycin resistance, the neomycin phophotransferase (NPTH) gene encoding kanamycin or geneticin resistance, the hygromycin resistance, genes coding for resistance to herbicides which act to inhibit the action of acetolactate synthase (ALS), in particular, the sulfonylurea-type herbicides; e.g., the acetolactate synthase (ALS) gene containing mutations leading to such resistance in particular the S4 and/or Hra mutations, genes coding for resistance to herbicides which act to inhibit action of glutamine synthase, such as phophinothricin or basta; e.g. the bar gene, or other similar genes known in the art. The bar gene encodes resistance to the herbicide basta, the nptII gene encodes resistance to the antibiotics kanamycin and geneticin, and the ALS gene encodes resistance to the herbicide chlorsulfuron.

Typical vectors useful for expression of foreign genes in plants are well known in the art, including, but not limited to, vectors derived from the tumor-inducing (Ti) plasmid of *Agrobacterium tumefaciens*. These vectors are plant integrating vectors that upon transformation, integrate a portion of the DNA into the genome of the host plant; see e.g., Rogers et al. (1987) Meth In Enzymol. 153:253-277; Schardl et al. (1987) Gene 61:1-11; and Berger et al., Proc. Natl. Acad. Sci. U.S.A. 86:8402-8406.

Vectors comprising sequences encoding the polypeptides and vectors comprising post-translational enzymes or subunits thereof may be co-introduced into the desired plant. Procedures for transforming plant cells are available in the art, for example, direct gene transfer, in vitro protoplast transformation, plant virus-mediated transformation, liposome-mediated transformation, microinjection, electroporation, *Agrobacterium* mediated transformation, and particle bombardment; see e.g., Paszkowski et al. (1984) EMBO J. 3:2717-2722; U.S. Pat. No. 4,684,611; European Application No. 0 67 553; U.S. Pat. Nos. 4,407,956; 4,536,475; Crossway et al. (1986) Biotechniques 4:320-334; Riggs et al. (1986) Proc. Natl. Acad. Sci USA 83:5602-5606; Hinchee et al. (1988) Biotechnology 6:915-921; and U.S. Pat. No. 4,945,050.) Standard methods for the transformation of, e.g., rice, wheat, corn, sorghum, and barley are described in the art; see, e.g., Christou et al. (1992) Trends in Biotechnology 10: 239 and Lee et al. (1991) Proc. Nat'l Acad. Sci. USA 88:6389. Wheat can be transformed by techniques similar to those employed for transforming corn or rice. Furthermore, Casas et al. (1993) Proc. Nat'l Acad. Sci. USA 90:11212, describe a method for transforming sorghum, while Wan et al. (1994) Plant Physiol. 104: 37, teach a method for transforming barley. Suitable methods for corn transformation are provided by Fromm et al. (1990) Bio/Technology 8:833 and by Gordon-Kamm et al., supra.

Additional methods that may be used to generate plants that produce animal collagens are established in the art; see, e.g., U.S. Pat. Nos. 5,959,091; 5,859,347; 5,763,241; 5,659,122; 5,593,874; 5,495,071; 5,424,412; 5,362,865; 5,229,112; 5,981,841; 5,959,179; 5,932,439; 5,869,720; 5,804,425; 5,763,245; 5,716,837; 5,689,052; 5,633,435; 5,631,152; 5,627,061; 5,602,321; 5,589,612; 5,510,253; 5,503,999; 5,378,619; 5,349,124; 5,304,730; 5,185,253; 4,970,168; European Publication No. EPA 00709462; European Publication No. EPA 00578627; European Publication No. EPA 00531273; European Publication No. EPA 00426641; PCT Publication No. WO 99/31248; PCT Publication No. WO 98/58069; PCT Publication No. WO 98/45457; PCT Publication No. WO 98/31812; PCT Publication No. WO 98/08962; PCT Publication No. WO 97/48814; PCT Publication No. WO 97/30582; and PCT Publication No. WO 9717459.

Insect Expression.

Another alternative expression system for collagen is an insect system. Baculoviruses are very efficient expression vectors for the large scale production of various recombinant proteins in insect cells. The methods as described in Luckow et al. (1989) Virology 170:31-39 and Gruenwald, S. and Heitz, J. (1993) Baculovirus Expression Vector System: Procedures & Methods Manual, Pharmingen, San Diego, Calif., can be employed to construct expression vectors containing a collagen coding sequence for the collagens of the invention and the appropriate transcriptional/translational control signals. For example, recombinant production of proteins can be achieved in insect cells, by infection of baculovirus vectors encoding the polypeptide. The production of recombinant collagen, collagen-like or collagenous polypeptides with stable triple helices can involve the co-infection of insect cells with three baculoviruses, one encoding the animal collagen to be expressed and one each encoding the α subunit and β subunit of prolyl 4-hydroxylase. This insect cell system allows for production of recombinant proteins in large quantities. In one such system, *Autographa californica* nuclear polyhidrosis virus (AcNPV) is used as a vector to express foreign genes. This virus grows in *Spodoptera frugiperda* cells. Coding sequences for collagen or collagen-like polypeptides may be cloned into non-essential regions (for example the polyhedron gene) of the virus and placed under control of an AcNPV promoter (for example, the polyhedron promoter). Successful insertion of a coding sequence will result in inactivation of the polyhedron gene and production of non-occluded recombinant virus; e.g., viruses lacking the proteinaceous coat coded for by the polyhedron gene. These recombinant viruses are then used to infect *Spodoptera frugiperda* cells in which the inserted gene is expressed; see, e.g., Smith et al. (1983) J. Virol. 46:584; and U.S. Pat. No. 4,215,051. Further examples of this expression system may be found in, for example, Ausubel et al. above.

Animal Expression.

In animal host cells, a number of expression systems may be utilized. In cases where an adenovirus is used as an expression vector, polynucleotide sequences encoding collagen or collagen-like polypeptides may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the encoded polypeptides in infected hosts; see, e.g., Logan & Shenk, Proc. Natl. Acad. Sci. USA 81:3655-3659 (1984). Alternatively, the vaccinia 7.5 K promoter may be used; see, e.g., Mackett et al. (1982) Proc. Natl. Acad. Sci. USA 79:7415-7419; Mackett et al. (1982) J. Virol. 49:857-864; and Panicali et al. (1982) Proc. Natl. Acad. Sci. USA 79:4927-4931.

A preferred expression system in mammalian host cells is the Semliki Forest virus. Infection of mammalian host cells, for example, baby hamster kidney (BHK) cells and Chinese hamster ovary (CHO) cells can yield very high recombinant expression levels. Semliki Forest virus is a preferred expression system as the virus has a broad host range such that infection of mammalian cell lines will be possible. More specifically, Semliki Forest virus can be used in a wide range of hosts, as the system is not based on chromosomal integration, and thus provides an easier way of obtaining modifications of the recombinant animal collagens in studies aiming at identifying structure function relationships and testing the effects of various hybrid molecules. Methods for constructing Semliki Forest virus vectors for expression of exogenous proteins in mammalian host cells are described in, for example, Olkkonen et al. (1994) Methods Cell Biol 43:43-53.

Non-human transgenic animals may also be used to express the polypeptides. Such systems can be constructed by operably linking the polynucleotide of the invention to a promoter, along with other required or optional regulatory sequences capable of effecting expression in mammary glands. Likewise, required or optional post-translational enzymes may be produced simultaneously in the target cells employing suitable expression systems. Methods of using non-human transgenic animals to recombinantly produce proteins are known in the art; see, e.g., U.S. Pat. Nos. 4,736,866; 5,824,838; 5,487,992; and 5,614,396.

The references cited in the sections above which describe the production of recombinant collagens are each incorporated by reference. Despite the teaching of prior art, there is a continuing need for yeast strains with increased collagen production and increased collagen stability.

SUMMARY OF THE INVENTION

Among its other embodiments, the invention is directed to strains of yeast genetically engineered to produce non-hydroxylated collagen. In an alternative embodiment, the present invention provides strains of engineered yeast to produce hydroxylated collagen. In one embodiment, the present invention provides an all-in-one vector including the DNA necessary to produce collagen, the promotor, and/or the hydroxylating enzymes. Methods for producing non-hydroxylated or hydroxylated collagen are also provided.

DETAILED DESCRIPTION OF THE INVENTION

Figure 1:
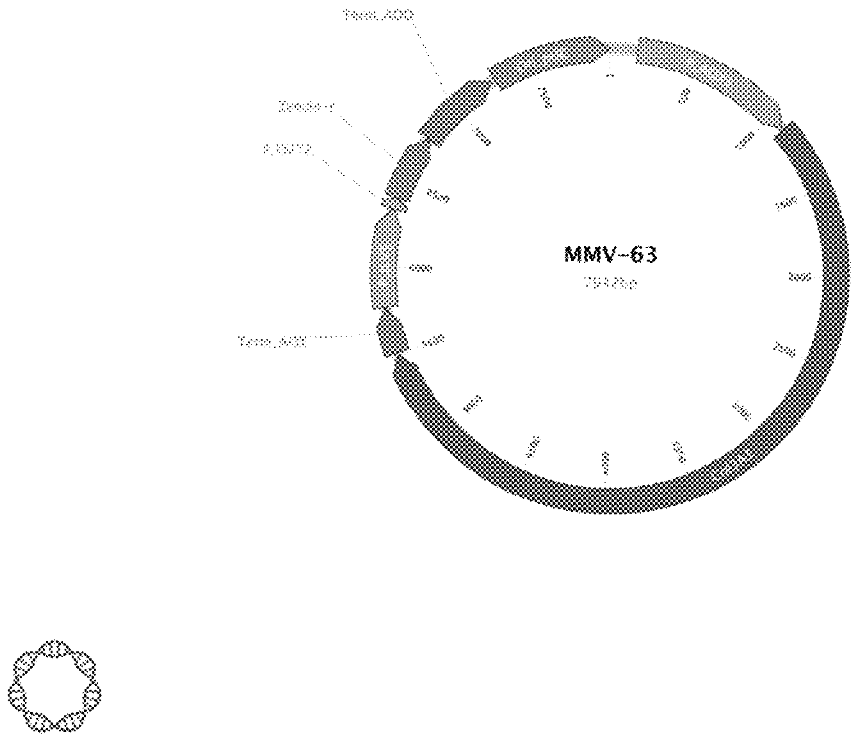
FIG. 1 shows the vector diagram of MMV 63 which was designed to produce non-hydroxylated collagen.

The present invention utilizes yeast to produce collagen. Suitable yeast includes, but are not limited to, those of the genus *Arxula, Candida, Komagataella, Pichia, Hansenula, Ogataea, Saccharomyces, Cryptococcus* and combinations thereof. The yeast maybe modified or hybridized. Hybridized yeast are mixed breeding of different strains of the same species, different species of the same genus or strains of different genera.

Foreign DNA is inserted into the yeast genome or maintains episomal to produce collagen. The DNA sequence for the collagen is introduced into the yeast via a vector. It is known in the art that modification to the DNA, such as codon optimization, may improve the ability and efficiency of the yeast to translate the DNA. Foreign DNAs are any non-yeast host DNA and include for example, but not limited to, mammalian, *Caenorhabditis elegans* and bacteria. Suitable mammalian DNA for collagen production in yeast include, but is not limited to, bovine, porcine, kangaroo, alligator, crocodile, elephant, giraffe, zebra, llama, alpaca, lamb, dinosaur and combinations thereof.

The DNA is inserted on a vector, suitable vectors include, but are not limited to, pHTX1-BiDi-P4HA-Pre-P4HB hygro, pHTX1-BiDi-P4HA-PHO1-P4HB hygro, pGCW14-pGAP1-BiDi-P4HA-Prepro-P4HB G418, pGCW14-pGAP1-BiDi-P4HA-PHO1-P4HB Hygro, pDF-Col3A1 optimized Zeocin, pCAT-Col3A1 optimized Zeocin, pDF-Col3A1 optimized Zeocin with AOX1 landing pad, pHTX1-BiDi-P4HA-Pre-Pro-P4HB hygro. The vectors typically include at least one restriction site for linearization of DNA.

It is known in the art that promotors can improve the production of proteins. Promoters are DNA sequences included in the vectors. Suitable promoters for use in the present invention include, but are not limited to, AOX1 methanol induced promoter, PDF de-repressed promoter, PCAT de-repressed promoter, Das1-Das2 methanol induced bi-directional promoter, PHTX1 constitutive Bi-directional promoter, a CHO histone promoter, PGCW14-PGAP1 constitutive Bi-directional promoter and combinations thereof.

A terminator is required at the end of each open reading frame utilized in the vectors incorporated into the yeast. The DNA sequence for the terminator is inserted into the vector.

An origin of replication is necessary to initiate replication. The DNA sequence for the origin of replication is inserted into the vector. The vector may additionally be empisomally maintained.

A DNA sequence containing homology to the yeast genome is necessary and is incorporated into the vector.

Selection markers are used to select yeast cells that have been successfully transformed. The markers sometimes are related to antibiotic resistance. The markers may also be related to the ability to grow with or without certain amino acids (auxotrophic markers). Suitable auxotrophic markers include, but are not limited to ADE, HIS, URA, LEU, LYS, TRP and combinations thereof. A DNA sequence for a selection marker is incorporated into the vector.

Prior to post-translational modification, collagen is non-hydroxylated and degrades in the presence of high pepsin concentration, for example a 1:200 Pepsin may be used to cleave the N-terminal and the C-terminal propeptides of collagen to enable fibrillation, which enables converting collagen to bio fabricated material. Therefore, it is useful to provide hydroxylated collagen. To enable the production of hydroxylated collagen, at least one second protein may be necessary. This second protein is an enzyme known as Prolyl 4-hydroxylase subunit alpha-1, hereafter "P4HA1" and Prolyl 4-hydroxylase subunit beta, hereafter "P4HB". P4HA1 and P4HB DNA may be inserted into the yeast on a vector to hydroxylate the collagen. Hydroxylated collagen has better thermostability compared to non-hydroxylated collagen and is resistant to high concentration pepsin digestion, for example 1:25 to 1:1, total protein to pepsin ratio.

The engineered yeasts above require multiple vectors and each step in the process of loading vectors into the cell can be very time consuming. Multiple vectors also carry multiple selection markers making it difficult to reuse markers when adding new DNA. We have surprisingly found that an "all-in-one vector" could be constructed with the DNA of the collagen and the DNA of P4HA and P4HB combined on a single vector. Promoters and signal sequences can be modularly added at specified cloning sites. The DNA can be inserted in yeast for hydroxylated or non-hydroxylated collagen depending on the presence or absence of the promotors. The all-in-one vector includes sites for linearization to insert the DNA into the yeast including both for random and site directed integration into the genome.

The term "collagen" refers to any one of the known collagen types, including collagen types I through XX, as well as to any other collagens, whether natural, synthetic, semi-synthetic, or recombinant. It includes all of the collagens, modified collagens and collagen-like proteins described herein. The term also encompasses procollagens and collagen-like proteins or collagenous proteins comprising the motif (Gly-X-Y)n where n is an integer. It encompasses molecules of collagen and collagen-like proteins, trimers of collagen molecules, fibrils of collagen, and fibers of collagen fibrils. It also refers to chemically, enzymatically or recombinantly-modified collagens or collagen-like molecules that can be fibrillated as well as fragments of collagen, collagen-like molecules and collagenous molecules capable of assembling into a nanofiber.

In some embodiments, amino acid residues, such as lysine and proline, in a collagen or collagen-like protein may lack hydroxylation or may have a lesser or greater degree of hydroxylation than a corresponding natural or unmodified collagen or collagen-like protein. In other embodiments, amino acid residues in a collagen or collagen-like protein may lack glycosylation or may have a lesser or greater degree of glycosylation than a corresponding natural or unmodified collagen or collagen-like protein.

The collagen in a collagen composition may homogenously contain a single type of collagen molecule, such as 100% bovine Type I collagen or 100% Type III bovine collagen, or may contain a mixture of different kinds of collagen molecules or collagen-like molecules, such as a mixture of bovine Type I and Type III molecules. Such mixtures may include >0%, 10, 20, 30, 40, 50, 60, 70, 80, 90, 95, 99 or <100% of the individual collagen or collagen-like protein components. This range includes all intermediate values. For example, a collagen composition may contain 30% Type I collagen and 70% Type III collagen, or may contain 33.3% of Type I collagen, 33.3% of Type II collagen, and 33.3% of Type III collagen, where the percentage of collagen is based on the total mass of collagen in the composition or on the molecular percentages of collagen molecules.

The engineered yeast cells described above can be utilized to produce collagen. In order to do so, the cells are placed in media within a fermentation chamber or vat and fed dissolved oxygen and a source of carbon, under controlled pH conditions for a period of time ranging from twelve hours to 1 week. Suitable media include but are not limited to buffered glycerol complex media (BMGY), buffered methanol complex media (BMMY), and yeast extract peptone dextrose (YPD). Due to the fact that collagen is produced in the yeast cell, in order to isolate the collagen, one must either use a secretory strain of yeast or lyse the yeast cells to release the collagen. The collagen may then be purified through know techniques such as centrifugation, precipitation and the like.

The collagen disclosed herein makes it possible to produce a bio fabricated leather. Methods for converting collagen to bio fabricated leather are taught in patent applications U.S. application Ser. Nos. 15/433,566, 15/433,650, 15/433,632, 15/433,693, 15/433,777, 15/433,675, 15/433,676 and 15/433,877, the disclosures of which are hereby incorporated by reference.

Embodiments of the Invention

The invention includes, but is not limited to genetically engineered strains of yeast and methods for producing collagen.

In a first embodiment, the present invention is directed to a strain of yeast that produces non-hydroxylated collagen including a yeast host; a recombinant DNA of a target protein; and a promoter.

In a second embodiment, the present invention is directed to a strain of yeast that produces hydroxylated collagen including a yeast host; a recombinant DNA of a target protein; a DNA of a second target protein; and at least one promoter.

In a third embodiment, the present invention is directed to an all-in-one vector including a DNA of a target protein; a DNA of a second target protein; and a DNA for at least one promotor. Examples: Gelatin, Collagen I, and to introduce more than one gene.

In a fourth embodiment, the present invention is directed to a method for making collagen.

In a fifth embodiment, the present invention is directed to a method for making hydroxylated collagen.

Detailed Description of Embodiments

As used herein, the term DNA means Deoxyribonucleic Acid.

As used herein, the term titer means the amount of target protein produced.

As used herein, the term bio fabricated leather means the use of biology, engineering and design to create a material with leather-like properties.

As used herein, the term all-in-one vector means a vector that includes all DNAs necessary to produce a desired recombinant protein.

As used herein, the term stable collagen means that after being exposed to high concentration of pepsin at least 75% of the initial concentration of collagen is still present.

The following non-limiting Examples are illustrative of the present invention. The scope of the invention is not limited to the details described in these Examples.

Example 1

Yeast Intended to Produce Recombinant Collagen

Wild type *Pichia pastoris* from DNA 2.0 was obtained. A MMV 63 (Sequence 9) DNA sequence including a collagen sequence was inserted into wild type *Pichia pastoris* which generated strain PP28. MMV63 was digested by Pme I and transformed into PP1 (Wild Type *Pichia pastoris* strain) to generate PP28. The vector MMV63 is shown in FIG. 1.

Native bovine collagen was sequenced (Sequence 1) and the sequence was amplified using the following polymerase chain reaction "PCR" protocol to create a linear DNA sequence:

PfuUltra II Fusion HS DNA Polymerase Protocol

For a 50 ul reaction:

| Component | Volume | Final Concentration |
|---|---|---|
| Pfu polymerase | 1 ul | |
| 10 mM dNTP | 1 ul | 200 uM |
| 10× Pfu ultra HF reaction Buffer | 5 ul | 1.0x |
| Primer 1, 5 uM | 1 ul | 0.1 uM |
| Primer 2, 5 uM | 1 ul | 0.1 uM |
| DNA | Variable | 5-30 ng |
| water | Total volume made up with water to 50 ul | |

*One of ordinary skill in the art appreciates that multiple primers may be used based on the DNA to be amplified.

Thermocycler Protocol for <10 kb of DNA:

95 C for 2 min, 30 cycles of 95 C for 20 seconds, [primer melting temperature-5 C for 20 seconds 72 C for 15 seconds if <1 kb, otherwise 15 sec per kB, 72 C for 3 min, and 4 C forever.

The linear DNA was cloned following the Gibson Procedure, as follows;

For 2-3 fragments, 0.02-0.5 pmol DNA was used. For 4-6 fragments, 0.2-1.0 pmol DNA was used.

Pmols=(weight in ng)×1000/(base pairs×650 daltons)

Or use NEBioCalculator

Optimized efficiency is 50-100 ng vector with 2-3 fold excess insert (use 5 fold excess if <200 bp). Total volume of PCR fragments should not exceed 20%.

1. Set up following reaction:

| | Recommended Amount of Fragments Used for Assembly | | |
|---|---|---|---|
| | 2-3 Fragment Assembly | 4-6 Fragment Assembly | Positive Control** |
| Total Amount of Fragments | 0.02-0.5 pmols* X µl | 0.2-1 pmols* X µl | 10 µl |
| Gibson Assembly Master Mix (2x) | 10 µl | 10 µl | 10 µl |
| Deionized $H_2O$ | 10-X µl | 10-X µl | 0 |
| Total Volume | 20 µl*** | 20 µl*** | 20 µl |

2. Incubate in thermocycler at 50 C for 15 min (2-3 frag) or 60 min (4-6 frag). Store at ice or −20 C before transformation
3. Transform NEB 5-alpha cells with 2 ul of assembly reaction.

The clones were transformed into *E. Coli* following the procedure below:

Thaw 50 ul competent cells (typically 5 alpha) on ice
Add 10-100 ng DNA in 2 ul volume
Let sit on ice for 5 min
Heat shock at 42 C for 10 seconds
Let sit on ice for 5 min
Meanwhile, prepare tubes or plate with 1 ml Super optimal broth with catabolite repression ("SOC") liquid medium
Transfer competent cells into appropriate tube or well on plate
Let shake at 37 C for 1 hour for outgrowth
Meanwhile, label plates and place in 37 C incubator to warm up.
Spin at 10,000 g for 30 s to concentrate cells at bottom
Remove and discard 800 ul of SOC. You should have ~200 ul leftover
Add entire 200 ul to room temperature agar plates. Alternatively, add 10% (20 ul) to plate 1 and 90% (180 ul) to plate 2.
Spread on plate using sterile glass beads.
Incubate at 37 C overnight The transformed cells were grown out into colonies and *E. Coli* Colony PCR was performed according to the procedure below:

GoTaq Green Master Mix Protocol (Taq Polymerase)
For 20 ul reaction:

| Component | Volume | Final Concentration |
|---|---|---|
| GoTaq Green MM 2x | 10 ul | 1x |
| Primer 1, 5 uM | 1 ul | 0.1 uM |
| Primer 2, 5 uM | 1 ul | 0.1 uM |
| Colony | tooth pick | |
| water | 8 ul | |

Thermocycler Protocol:
95 C for 2 min
28 cycles of
95 C for 30 seconds
[primer melting temperature-5 C] for 30 seconds
72 C for 1 minute per kB
72 C for 5 min
4 C forever To screen the colonies for effectiveness of transformation, agarose DNA Gel procedure was followed as described below:

To make an x % agarose gel (typically 8-12%):

1. Measure X g agarose to achieve your desired percentage. 1 g=1 ml. For example, to make a 1% gel you measure 1 g agarose into 100 ml Tris base, acetic acid, and ethylene diamine tetraacetic acid buffer ("TAE")
2. Add agarose to 250 ml flask
3. Bring to 100 ml TAE buffer, or your desired volume
4. Microwave until liquid is clear. For 1% in 100 ml, this takes ~1 min 30 seconds.
5. Add SYBR Safe DNA stain to 1× (it is at 10,000×, so add your total agarose volume in ml/10 to get total ul to add. For example, if you have 100 ml agarose, add 10 ul)
6. Pour into mold. Remember to add the well slots.
7. Wait 45 min to 1 hr for gel to dry.

To run a gel:

1. Remove the well mold from the dried gel
2. Remove the gel+plastic support (don't take gel off plastic support) and transfer to gel box
3. Pour TAE over gel so that it is completely submerged
4. Load 10-20 ul of ladder. 100 ng should be more than enough to visualize.
5. Load your DNA samples (after they have been mixed with gel loading dye). Gel loading dye is 6× and should be diluted to 1× to load samples (ex: mix 4 ul dye+20 ul DNA and load all 24 ul). DNA PCRed with GoTaq® Green Master Mix already have dye incorporated into the mix, and do not need to have dye added. 100 ng should be more than enough to visualize. Some samples may need to be diluted.
6. Place the wired top on the gel box. The negative (black) should be on the side with the wells.
7. Plug gel box into power supply. Run at 100-120 voltage for 10-30 min.

*Dye migrates opposite from DNA (toward (−) charge). This is why running a gel longer/multiple times is inadvisable and you will not be able to visualize anything. Do not re-use gels. Pour new ones instead. You can also put dye into the buffer itself, which may help with visualization.

In order to purify the vector from *E. Coli* a DNA prep kit was utilized as described in Zymo Research mini prep kit, following manufacturer's protocol.

Sanger sequencing was performed by Genewiz or Eurofins according to vendor's protocol. The results confirmed that after obtaining transformed clones the DNA sequence is correct.

Large scale DNA preparation was performed using Midi Preparation Kit as described in manufacturer's protocol. Obtained kit from Zymo Research. The results show we generated a significant amount of circular DNA or plasmids.

Plasmids were converted to linear DNA using the Restriction Digestion Guide (from Addgene) as described below:

Select restriction enzymes to digest your plasmid.
Note: To determine which restriction enzymes will cut your DNA sequence (and where they will cut), use a sequence analysis program such as Addgene's Sequence Analyzer.
Determine an appropriate reaction buffer by reading the instructions for your enzyme.
Note: If you are conducting a double digest (digesting with two enzymes at the same time), you will need to determine the best buffer that works for both of your enzymes. Most companies will have a compatibility chart, such as the double digest finder tool from NEB. If you cannot find a buffer that is appropriate for both of your enzymes, you will need to digest with one enzyme first in the buffer for enzyme 1, re-purify the cut plasmid, and then conduct the second digest in the buffer for enzyme 2.

In a 1.5 mL tube combine the following:

DNA

Restriction Enzyme(s)

Buffer (1×)

BSA (if recommended by manufacturer)

$dH_2O$ up to total volume

Note: The amount of DNA that you cut depends on your application. Diagnostic digests typically involve ~500 ng of DNA, while molecular cloning often requires 1-3 μg of DNA. The total reaction volume usually varies from 10-50 μL depending on application and is largely determined by the volume of DNA to be cut.

Note: See Tips and FAQ section below for note on determination of restriction enzyme volume to use.

Note: A typical restriction digestion reaction could look like this:

1 μg DNA

1 μL of each Restriction Enzyme

3 μL 10× Buffer

3 μL 10×BSA (if recommended)

x μL $dH_2O$ (to bring total volume to 30 μL)

Mix gently by pipetting.

Incubate tube at appropriate temperature (usually 37° C.) for 1 hour. Always follow the manufacturer's instructions.

Note: Depending on the application and the amount of DNA in the reaction, incubation time can range from 45 min to overnight.

The DNA was purified using the Phenol-Chloroform DNA Extraction and Purification procedure described below:

Materials 1. 3M NaOAc (Sodium Acetate)
2. 100% Ethanol, cold
3. 70% Ethanol, cold
4. Phenol-Chloroform-Isoamyl Alcohol in 25:24:1 ratio Procedure 1. Add 10% volume of NaOAc to DNA (ex: 50 ul to 500 ul)
2. Add equal volume of phenol-chloroform-isopropanol, careful to take from the bottom/heavier phase; vortex
3. Centrifuge at 12,000 g for 5 min
4. Transfer top phase to a new tube
5. Add 2.5 volumes of cold 100% ethanol, vortex. The liquid should look cloudy if there is a lot of DNA.
6. Put at −80 C for 10 minutes, or on dry ice
7. Centrifuge at max speed for 10 minutes, at 4 C if possible. Remove majority of the supernatant (leave ~50 ul)
8. Wash with 1 ml cold 70% ethanol, adding wash with no additional mechanical action (do not actively disturb pellet).
9. Centrifuge for 5 min at max speed
10. Remove the majority of the 70% ethanol; leave to air dry for 10-30 min
11. Resuspend in 20-30 ul of water or TE buffer Notes:

Optimized volumes for microfuge tubes:

400 ul DNA 40 ul NaOAc 440 ul Phenol-Chloroform-Isoamyl Alcohol

Top phase recovered ~400 ul

Add 1 ml 100% ETOH

The DNA was transformed into yeast cells according to the procedure below: *Pichia* Electroporation Protocol (Bio-Rad Gene Pulser Xcell™ Total System #1652660)

*Pichia* strain—WT *Pichia* from DNA2.0 transformed with P4HA/B co-expression plasmid and selected on Hygro plate (200 ug/ml). Clone #4

1. Single colony was inoculated in 100 ml YPD medium and grown at 30 degrees overnight with shaking (215 rpm).
2. Next day the culture reaches OD600 ~3.5 (~3-5×$10^7$ cells/OD600). Dilute the culture with fresh YPD to OD600 ~1.7 and grow for another hour at 30 degree with shaking (215 rpm).
3. Spin down the cells at 3,500 g for 5 min; wash once with water and resuspend in 10 ml 10 mM Tris-HCl (pH 7.5), 100 mM LiAc, 10 mM DTT (add fresh), 0.6 M Sorbitol
4. For each transformation, aliquot 8×$10^8$ cells into 8 ml 10 mM Tris-HCl (pH 7.5), 100 mM LiAc, 10 mM DTT, 0.6 M Sorbitol and incubate at room temperature for 30 min.
5. Spin down the cells at 5000 g for 5 mins and wash with ice cold 1.5 ml 1M Sorbitol 3 times and resuspend in 80 ul ice cold 1M Sorbitol
6. Add various amount (about 5 ug) of linearized DNA to the cells and mix by pipetting.
7. Add cells and DNA mixture (80-100 ul) into 0.2 cm cuvette and pulse using *Pichia*—protocol (1500 v, 25 uF, 200Ω)
8. Immediately transfer the cells into 1 ml mixture of YPD and 1M Sorbitol (1:1) and incubate at 30 degree for >2 hour
9. Plate the cells at different densities.

Inoculate single colonies into 2 mL BMGY media in a 24 deep well plate and grew out for at least 48 hours at 30 degree Celsius with shaking at 900 rpm. The resulting cells were tested for collagen using cell lysis, SDS-page and pepsin assay following the procedure below.

The cells were lysed using the following procedure:

Preparation of 1× lysis buffer. The following recipe is suitable for preparing a combination of 50 samples.

2.5 ml 1 M HEPES; final concentration 50 mM.

438.3 mg NaCl; final concentration 150 mM.

5 ml Glycerol; final concentration 10%.

0.5 ml Triton X-100; final concentration 1%.

42 ml Millipure water.

Store buffer at 4° C. for 1 month.

Using a Qiagen TissueLyser, lyse *Pichia pastoris* cells.

Speed: 30 hz

Time: 15 min (continuous)

Centrifuge lysate at 2500 rpm for 15 mins on tabletop centrifuge. Collect about 600 ul of supernatant in a fresh tube or 96 well deep plate. Discard pellet.

SDS-Page was performed using the following procedure:

Preparation of Buffers and Solutions

Mix 50 ml of Pierce™ 20×Tris-Acetate SDS Buffer with 950 ml of Millipure Water to make 1×Tris-Acetate SDS Buffer.

Add 1500 ml of 1×Tris-Acetate SDS Buffer to each chamber of the Mini or Midi Gel Tank.

SDS-PAGE—Each gel will contain the following: Molecular Weight Markers, Negative Control, Positive Control(s), Samples.

Gel Preparation

Open plastic casing around gel.

Remove well comb from gel.

Remove white tape from gel.

Place gel into Midi Gel Tank as per manufacturer instructions.

Rinse gel wells with 5 ml of 1×Tris-Acetate SDS Buffer 1 ml at a time.

Aspirate bubbles and ensure all wells are submerged in 1×Tris-Acetate SDS Buffer.

Sample Preparation for Loading SDS-PAGE gel.

Thaw samples and controls on ice.

Dilute LDS buffer to 2× and add 10% 2-Mercaptoethanol final volume, make up the volume with water.

Mix each sample and LDS+2-ME in 1:1 ratio

Briefly vortex and centrifuge samples.

Incubate all samples at 70° C. for 7 minutes

Allow samples to cool to room temperature and briefly centrifuge.

Sample Loading

Add 20 μL of controls and samples and 10 ul molecular weight standards to each well Electrophoresis for 1 to 4 Midi Gel Tanks Create a one-step program on the PowerEase® 300W.

Step one is 150 V for one hour and 10 minutes.

Attach the lid of the Midi Gel Tank to the base as per the manufacturer's instructions.

Attach the power cables to the correct outlets on the PowerEase® 300W, making sure the red cable is attached to the red outlet, and the black cable is attached to the black outlet.

Repeat as necessary for up to 4 Midi Gel Tanks.

Run the one step program.

Prepare the gel for transfer.

Turn off PowerEase® 300W.

Unplug the Midi Gel Tank cables from the PowerEase® 300W.

Remove the lid from the Midi Gel Tank.

Remove the gel from the Midi Gel Tank.

Using the gel knife included with the Midi Gel Tank open the gel's plastic casing by wedging the blade of the knife into the plastic crevice and torqueing the knife. Repeat this motion along the crevice until the plastic case is separated into two.

Hold the plastic case with the gel attached to it gel-side down over the Nalgene™ Staining Box containing water and gently press the gel knife into the anode grove to release the gel into the Staining Box.

Repeat the following procedure 3 times to wash the gel in Millipore water.

Incubate for 30 seconds

Decant the water

Coomassie staining:

Add 10-20 ml of PageBlue Protein Staining Solution and incubate at room temperature for 60 minutes with gentle agitation on a shaker. Gels may be stained overnight without affecting the background.

Discard the staining solution and rinse the gel two times with MilliporeMillipure water. Discard the staining solution and water in a designated biohazard waste container, not down the drain.

Add 20 ml of water to destain. For complete destaining, it will take 10-12 hours. For faster destaining, add some methanol to water. Replacing water frequently will enhance destaining.

The pepsin assay was performed with the following procedure:

1. Before pepsin treatment perform BCA assay to obtain the total protein of each sample per Thermo Scientific protocol. Normalize the total protein to the lowest concentration for all samples. (Note: if lowest total protein concentration is less than 0.5 mg/mL do not use that concentration for normalization)
2. Put 100 uL of lysate in a microcentrifuge tube.
3. Create a master mix containing the following:
   a. 37% HCl (0.6 mL of acid per 100 mL) and
   b. Pepsin (stock is 1 mg/mL in deionized water, and final addition of pepsin should be at a 1:25 ratio pepsin:total protein (weight:weight).
   c. Based on step #1 normalization of total protein the amount of pepsin will vary for final addition, adjust using spreadsheet created.
4. After addition of pepsin, mix 3× with pipet and allow the samples to incubate for an hour at room temperature for the pepsin reaction to take place.
5. After an hour, add 1:1 volume of LDS loading buffer containing β-mercaptoethanol to each sample and allow to incubate for 7 minutes at 70° C. (In this situation 100 uL of LDS should be added).
6. Then spin at 14,000 rpm for 1 minute to remove the turbidity.
7. Add 18 uL from the top of sample onto a 3-8% TAE (using TAE buffer) and run gel for 1 hr 10 minutes at 150V. Or after boiling you can immediately place samples into −80° C. until a gel needs to be run.

The results are shown in Table 1 below.

Example 2

Yeast Producing Recombinant Collagen

Figure 2:
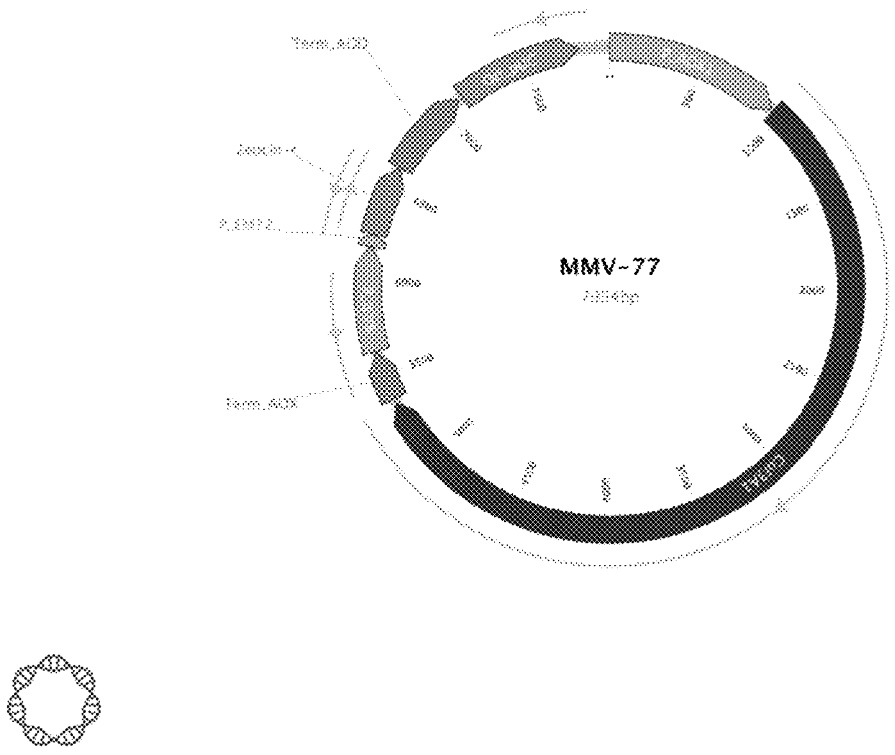
FIG. 2 shows the vector diagram of MMV77 which was designed to produce non-hydroxylated collagen.

Example 1 was repeated following the same procedures and protocols with the following changes: A DNA MMV77 (Sequence 10) sequence including a bovine collagen sequence optimized for *Pichia* expression (Bovine col3A1 optimized, sequence 2) was inserted into the yeast. A pAOX1 promoter (Sequence 3) was used to drive the expression of collagen sequence. A YPD plate containing Zeocin at 500 ug/ml was used to select successful transformants. The resulting strain was PP8. The vector MMV77 is shown in FIG. 2.

Restriction digestion was done using Pme I.

The strains were grown out in BMMY media and tested for collagen. The results are shown in Table 1 below.

Example 3

Yeast Producing Increased Amount of Recombinant Collagen

Figure 3:
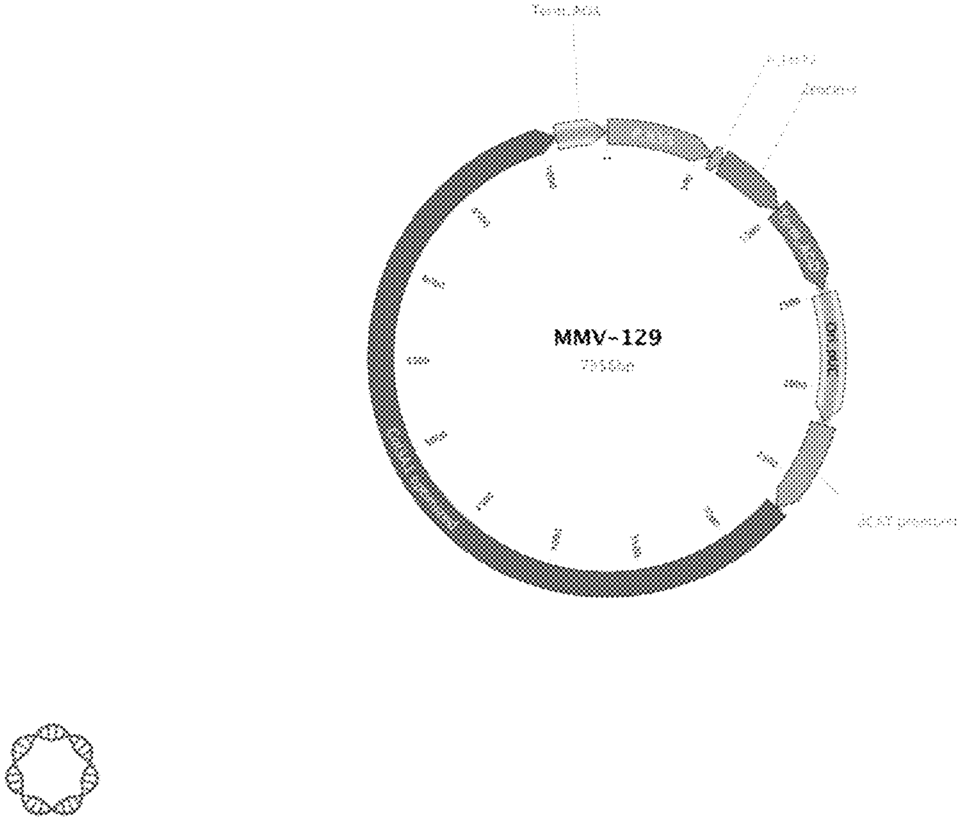
FIG. 3 shows the vector diagram of MMV 129 which was designed to produce non-hydroxylated collagen.
Figure 4:
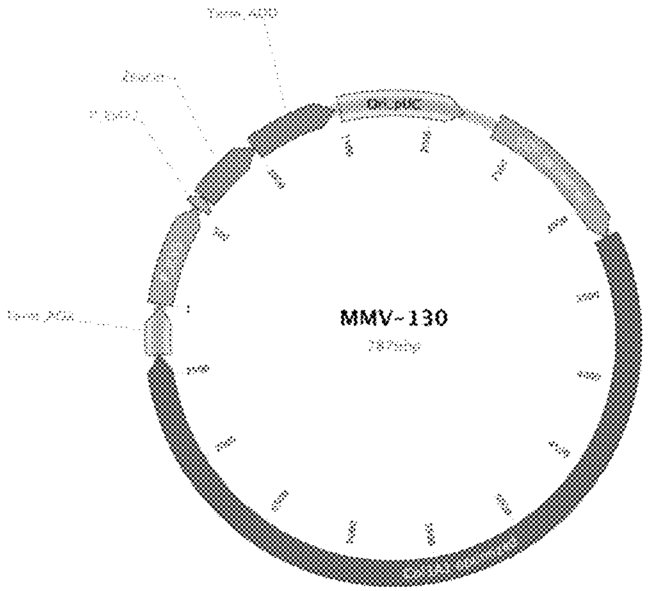
FIG. 4 shows the vector diagram of MMV 130 which was designed to produce non-hydroxylated collagen.

Example 1 was repeated following the same procedures and protocols with the following changes: A DNA MMV-129 (sequence 11) sequence including a bovine collagen sequence optimized for *Pichia* expression was inserted into the yeast. A pCAT promoter (Sequence 7) was used to drive the expression of collagen sequence. A YPD plate containing Zeocin at 500 ug/ml was used to select successful transformants. The resulting strain was PP123. MMV129 was digested by Swa I and transformed into PP1 to generate PP123. The vector MMV129 is shown in FIG. 3.

The strains were grown out in BMGY media and tested for collagen. The results are shown in Table 1 below.

Example 4

Yeast Producing Optimal Amount of Recombinant Collagen

Example 1 was repeated following the same procedures and protocols with the following changes:

A DNA MMV-130 (Sequence 12) sequence including a bovine collagen sequence (Sequence 2) optimized for *Pichia* expression was inserted into the yeast. A pDF promoter (Sequence 6) was used to drive the expression of collagen sequence. An AOX1 landing pad (cut by Pme I, sequence 8) was used to help site specific integration of the vector into the *Pichia* genome. A YPD plate containing Zeocin at 500 ug/ml was used to select successful transformants. The resulting strain was PP153. MMV130 was digested by Pme I and transformed into PP1 to generate PP153. (Bovine col3A1 optimized, sequence 2).

Phenol extraction was not used and PureLink PCR purification kit was used to recover linearized DNA.

The strains were grown out in BMGY media and tested for collagen. The results are shown in Table 1 below.

Example 5

Yeast Intended to Produce Recombinant Hydroxylated Collagen

Figure 5:
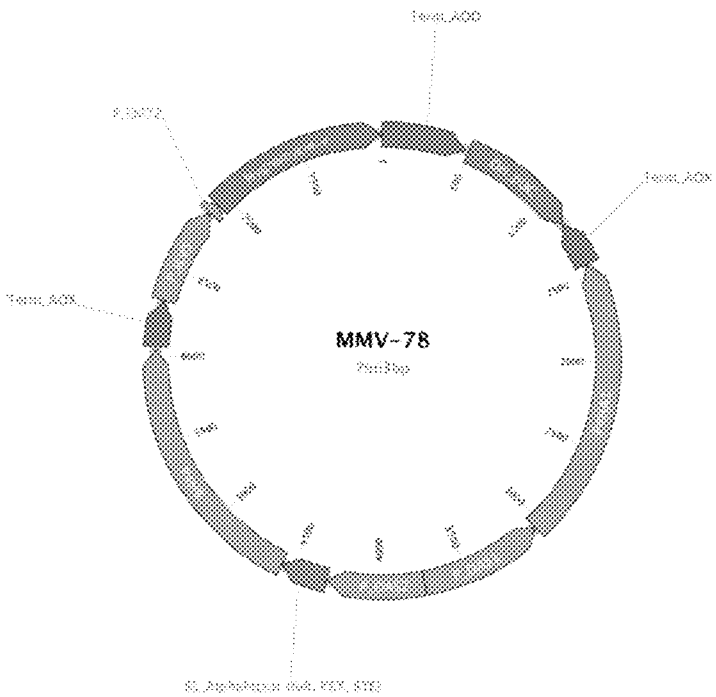
FIG. 5 shows the vector diagram of MMV 78 which was designed to produce hydroxylated collagen.

Example 2 was repeated following the same procedures and protocols with the following changes: One DNA vector, MMV-78 (Sequence 13), containing both bovine P4HA (Sequence 4) and bovine P4HB (sequence 5) sequences were inserted into the yeast. MMV78 was digested by Pme I and transformed into PP1 to generate PP8. Both P4HA and P4HB contain their endogenous signal peptides and are driven by the Das1-Das2 bi-directional promoter (Sequence 25). The DNA was digested by Kpn I and transformed into PP8 to generate PP3. Sequence 2. The vector MMV78 is shown in FIG. 5.

The strains were grown out in BMMY media and tested for collagen and hydroxylation. The results are shown in Table 1 below.

Example 6

Yeast Producing Recombinant Hydroxylated Collagen

Example 2 was repeated following the same procedures and protocols with the following changes: One DNA vector, MMV-78, containing both bovine P4HA and bovine P4HB sequences were inserted into the yeast. Both P4HA and P4HB contain their endogenous signal peptides and are driven by the Das1-Das2 bi-directional promoter. The DNA was digested by Kpn I and transformed into PP8 to generate PP3. Sequence 2.

Figure 6:
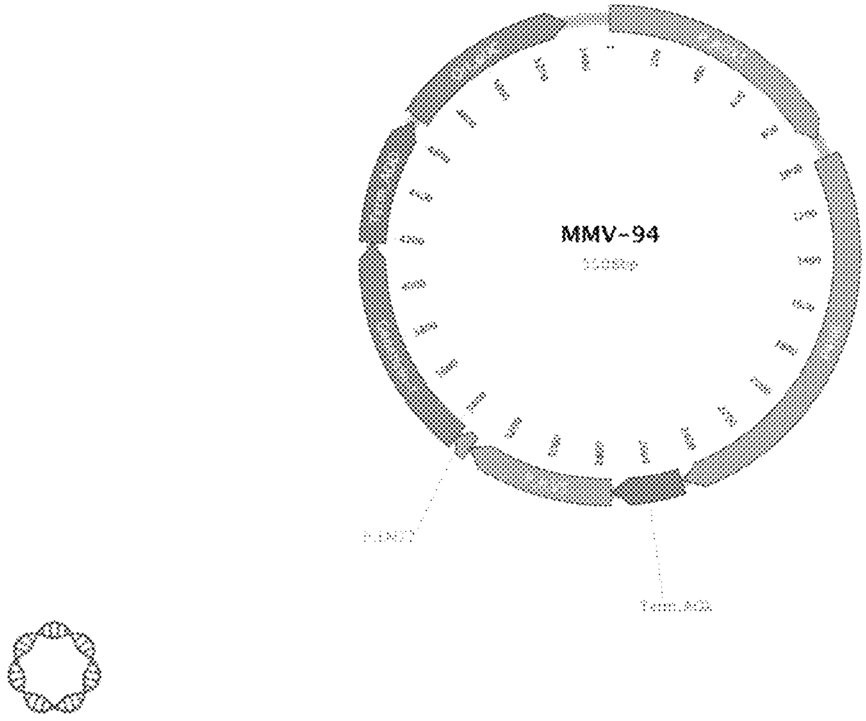
FIG. 6 shows the vector diagram of MMV 94 which was designed to produce hydroxylated collagen.

Another vector, MMV-94 (Sequence 14), containing P4HB driven by pAOX1 promoter was used and was also inserted into the yeast. The endogenous signal peptide of P4HB was replaced by PHO1 signal peptide. The resulting strain was PP38. MMV94 was digested by Avr II and transformed into PP3 to generate PP38. The vector MMV94 is shown in FIG. 6.

The strains were grown out in BMMY media and tested for collagen and hydroxylation. The results are shown in Table 1 below.

Example 7

Yeast Producing Increased Amount of Recombinant Hydroxylated Collagen

Figure 7:
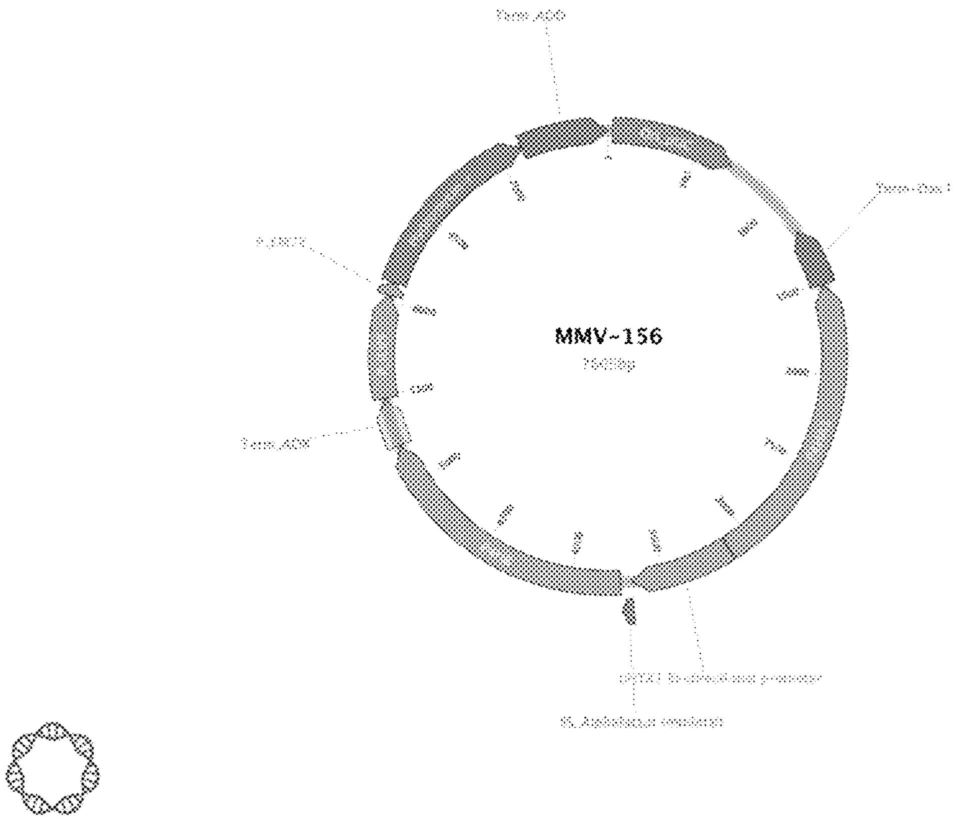
FIG. 7 shows the vector diagram of MMV 156 which was designed to produce hydroxylated collagen.

Example 4 was repeated following the same procedures and protocols with the following changes: One DNA vector, MMV-156 (Sequence 15), containing both bovine P4HA and bovine P4HB sequences were inserted into the yeast. The P4HA contains its endogenous signal peptides and P4HB signal sequence was replaced with Alpha-factor Pre (Sequence 21) sequence. Both genes were driven by the pHTX1 bi-directional promoter (Sequence 25). MMV156 was digested by Bam HI and transformed into PP153 to generate PP154. Sequence 2. The vector MMV156 is shown in FIG. 7. The strains were grown out in BMGY media and tested for collagen and hydroxylation. The results are shown in Table 1 below.

Example 8

Yeast Producing Optimal Amount Recombinant Hydroxylated Collagen

Example 4 was repeated following the same procedures and protocols with the following changes: One DNA vector, MMV-156, containing both bovine P4HA and bovine P4HB sequences were inserted into the yeast. The P4HA contains its endogenous signal peptides and P4HB signal sequence was replaced with Alpha-factor Pre sequence. Both genes were driven by the pHTX1 bi-directional promoter. The DNA was digested by Swa I and transformed into PP153 to generate PP154. Sequence 2.

Figure 8:
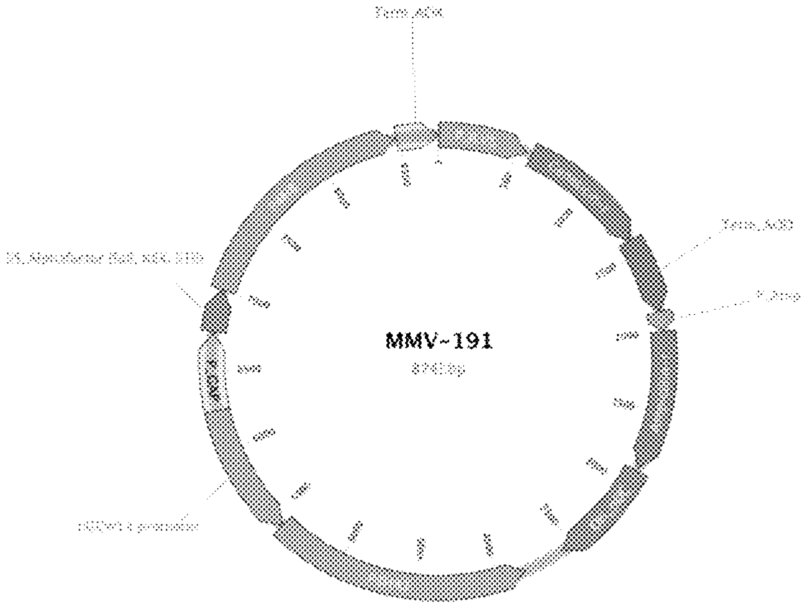
FIG. 8 shows the vector diagram of MMV 191 which was designed to produce hydroxylated collagen.
Figure 9:
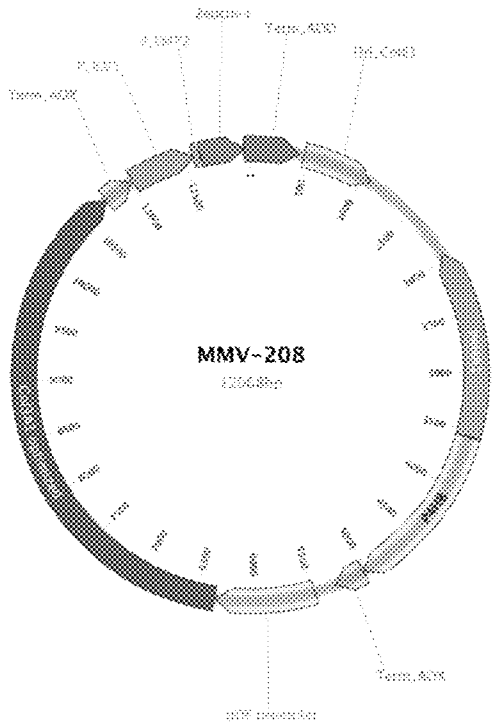
FIG. 9 shows an all-in-one vector MMV 208 which was designed to produce non-hydroxylated or hydroxylated collagen.
Figure 9:
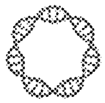
Figure 10:
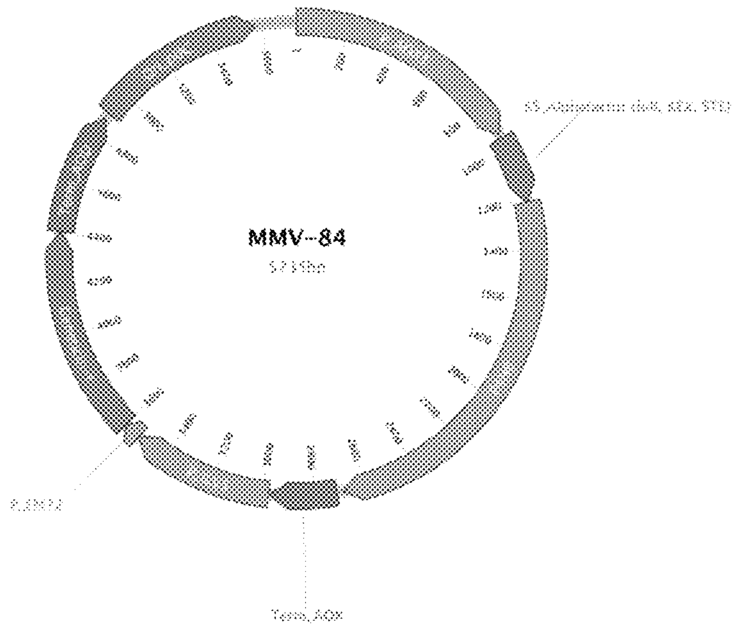
FIG. 10 shows the vector diagram of MMV84
Figure 11:
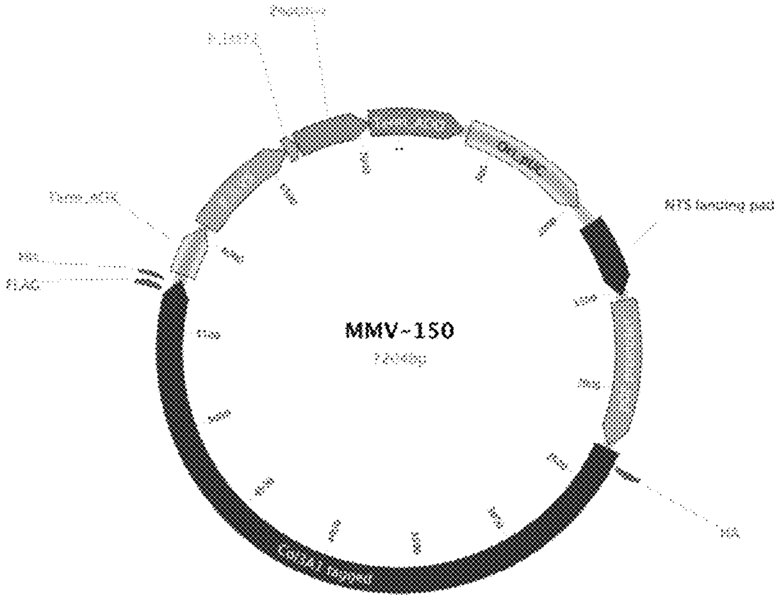
FIG. 11 shows the vector diagram of MMV 150
Figure 12:
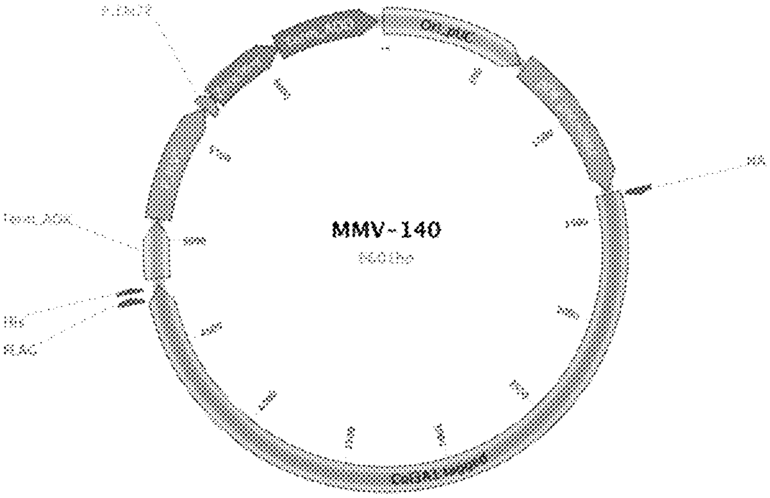
FIG. 12 shows the vector diagram of MMV140

Another vector, MMV-191 (Sequence 16), containing both P4HA and P4HB was also inserted into the yeast. The extra copy of P4HA contains its endogenous signal peptide and the signal sequence of the extra copy of P4HB was replaced with Alpha-factor Pre-Pro (Sequence 22) sequence. The extra copies of P4HA and P4HB were driven by the pGCW14-GAP1 bi-directional promoter (Sequence 23). MMV 191 was digested by Bam HI and transformed into PP154 to generate PP268. The vector MMV191 is shown in FIG. 8. The strains were grown out in BMGY media and tested for collagen and hydroxylation. The results are shown in Table 1 below.

Example 9

All-In-One Vector

The methods and procedures of example 1 were utilized to create an all-in-one vector. The All-in-One vector contains DNA of collagen and associated promoter and terminator, the DNA for the enzymes that hydroxylate the collagen and associated promoters and terminators, the DNA for marker expression and associated promoter and terminator, the DNA for origin(s) of replication for bacteria and yeast, and the DNA(s) with homology to the yeast genome for integration. The All-in-one vector contains strategically placed unique restriction sites 5', 3', or within the above components. When any modification to collagen expression or other vector components is desired, the DNA for select components can easily be excised out with restriction enzymes and replaced with the user's chosen cloning method. The simplest version of the All-in-one vector (MMV208, Sequence 17) includes all of the above components except promoter(s) for hydroxylase enzymes. Vector MMV208 was made using the following components: AOX homology from MMV84 (Sequence 18), Ribosomal homology from MMV150 (Sequence 19), Bacterial and yeast origins of replication from MMV 140 (Sequence 20), Zeocin marker from MMV140, and Col3A1 from MMV129. Modified versions of P4HA and B and associated terminators were synthesized from Genscript eliminating the following restriction sites: AvrII, NotI, PvuI, PmeI, BamHI, SacII, SwaI, XbaI, SpeI. The vector was transformed into strain PP1.

The strains were grown out in BMGY medium and tested for collagen and hydroxylation. The results are shown in Table 1 below.

TABLE 1

| Example | Collagen (g/L) | Hydroxylated Collagen (%) |
|---|---|---|
| 1* | 0.05 | 0 |
| 2 | 0.1 | 0 |
| 3 | 0.5 | 0 |
| 4 | 1-1.5 | 0 |
| 5* | 0.1 | 15 |
| 6 | 0.1 | 35 |
| 7 | 1-1.5 | 15 |
| 8 | 1-1.5 | 40-50 |
| 9 | 0.5-1 | 15-20 |

*Comparative Examples; in order to quantify collagen, coomassie stained gels were used. A collagen standard curve was used to determine the collagen concentration in the samples. The amount of hydroxylated collagen was estimated by comparing the sample band to a standard band after 1:25 pepsin treatment.

As discussed above, hydroxylated collagen is stable in high concentration of pepsin, therefore its useful not only to have increased amounts of collagen from a fermentation but to also have hydroxylated collagen.

Interpretation of Description

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

Incorporation by Reference

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The invention claimed is:

1. A strain of yeast genetically engineered to produce non-hydroxylated collagen wherein the strain comprises a vector comprising an optimized DNA sequence encoding bovine collagen, wherein the DNA sequence is at least 90% identical to SEQ ID NO: 2.

2. The strain of yeast of claim 1 wherein the strain of yeast is selected from the group consisting of Arxula, *Candida, Komagataella, Pichia, Hansenula, Ogataea, Saccharomyces, Cryptococcus* and combinations thereof.

3. The strain of yeast of claim 1 wherein the vector further comprises a DNA sequence for a promoter for the bovine collagen, wherein the promoter is selected from the group consisting of the AOX1 methanol induced promoter, the Das1-Das2 methanol induced bi-directional promoter, the PHTX1 constitutive bi-directional promoter, a CHO histone promoter, the PGCW14-PGAP1 constitutive bi-directional promoter and combinations thereof.

4. The strain of yeast of claim 1 wherein the vector further comprises a DNA sequence for a selection marker encoding for antibiotic resistance or an auxotrophic marker.

5. The strain of yeast of claim 4 wherein the selection marker encoding for antibiotic resistance encodes for resistance to at least one antibiotic selected from the group consisting of hygromycin, zeocin, geneticin and combinations thereof.

6. The strain of yeast of claim 1 wherein the vector is inserted into the yeast through a method selected from the group consisting of electroporation, chemical transformation, and mating.

7. The strain of yeast of claim 1 wherein the DNA sequence is at least 92.5% identical to SEQ ID NO: 2.

8. The strain of yeast of claim 1 wherein the DNA sequence is at least 95% identical to SEQ ID NO: 2.

9. A method for producing non-hydroxylated bovine collagen comprising growing the strain of yeast according to claim 1 in media for a period of time sufficient to produce the bovine collagen.

10. The method of claim 9 wherein the strain of yeast is selected from the group consisting of Arxula, *Candida, Komagataella, Pichia, Hansenula, Ogataea, Saccharomyces, Cryptococcus* and combinations thereof.

11. The method of claim 9 wherein the media is selected from the group consisting of buffered glycerol complex media (BMGY), buffered methanol complex media (BMMY), and yeast extract peptone dextrose (YPD).

12. The method of claim 9 wherein the period of time is from 24 hours to 72 hours.

13. The method of claim 12 wherein the yeast is selected from the group consisting of Arxula, *Candida, Komagataella, Pichia, Hansenula, Ogataea, Saccharomyces, Cryptococcus* and combinations thereof.

14. The method of claim 9 wherein the vector further comprises a DNA sequence for a promoter for the bovine collagen, wherein the promoter comprises PHTX1 constitutive bi-directional promoter or PGCW14-PGAP1 constitutive bi-directional promoter.

15. The method of claim 9 wherein the vector further comprises a DNA sequence for a selection marker encoding for antibiotic resistance or an auxotrophic marker.

16. A strain of yeast genetically engineered to produce hydroxylated bovine collagen wherein the strain comprises a first vector comprising an optimized DNA sequence encoding bovine collagen wherein the DNA sequence is at least 90% identical to SEQ ID NO: 2; and a second vector comprising a DNA sequence encoding P4HA1 and a DNA sequence encoding P4HB; and wherein the vectors have been inserted into the strain of yeast.

17. The strain of yeast of claim 16 wherein the yeast is selected from the group consisting of Arxula, *Candida, Komagataella, Pichia, Hansenula, Ogataea, Saccharomyces, Cryptococcus* and combinations thereof.

18. The strain of yeast of claim 16 wherein the first vector comprises a DNA sequence for a promoter for the bovine collagen, wherein the promoter is selected from the group consisting of AOX1 methanol induced promoter, Das1-Das2 methanol induced bi-directional promoter, PHTX1 constitutive bi-directional promoter, CHO histone promoter, PGCW14-PGAP1 constitutive bi-directional promoter and combinations thereof.

19. The strain of yeast of claim 16 wherein the second vector comprises a DNA sequence for a promoter for P4HA1 and P4HB, wherein the promoter is PHTX1 constitutive bi-directional promoter or PGCW14-PGAP1 constitutive bi-directional promoter.

20. The strain of yeast of claim 16 wherein the first vector, the second vector, or a combination thereof further comprises a DNA sequence for a selection marker encoding for antibiotic resistance or an auxotrophic marker.

21. The strain of yeast of claim 20 wherein the selection marker encoding for antibiotic resistance encodes for resistance to at least one antibiotic selected from the group consisting of hygromycin, zeocin, geneticin and combinations thereof.

22. The strain of yeast of claim 16 wherein the vector is inserted into the yeast through a method selected from the group consisting of electroporation, chemical transformation, and mating.

23. A method for producing hydroxylated bovine collagen comprising growing the strain of yeast in claim 16 in a media for a period of time sufficient to produce the bovine collagen.

24. The method of claim 23 wherein the strain of yeast is selected from the group consisting of Arxula, *Candida, Komagataella, Pichia, Hansenula, Ogataea, Saccharomyces, Cryptococcus* and combinations thereof.

25. The method of claim 23 wherein the media is selected from the group consisting of BMGY, BMMY, and YPD.

26. The method of claim 23 wherein the period of time is 24 hours to 72 hours.

27. The method of claim 26 wherein the yeast is selected from the group consisting of Arxula, *Candida, Komagataella, Pichia, Hansenula, Ogataea, Saccharomyces, Cryptococcus* and combinations thereof.

28. The method of claim 23 wherein the second vector further comprises a DNA sequence for a promoter for the P4HA1 and P4HB, wherein the promoter is PHTX1 constitutive bi-directional promoter or PGCW14-PGAP1 constitutive bi-directional promoter.

29. The method of claim 23 wherein the first vector, the second vector, or a combination thereof further comprises a DNA sequence for a selection marker encoding for antibiotic resistance or an auxotrophic marker.

30. An all-in-one vector comprising:

(i) an optimized DNA sequence encoding bovine collage, wherein the DNA sequence is at least 90% identical to SEQ ID NO: 2;

(ii) a DNA sequence encoding hydroxylation enzymes comprising P4HA1, P4HB, and combinations thereof, including promoters and terminators;

(iii) a DNA sequence for a selection marker, including a promoter and a terminator;

(iv) a DNA sequence for origins of replication for yeast and bacteria;

(v) DNA sequences with homology to a yeast genome for integration into the genome; and (vi) restriction sites at a position selected from the group consisting of 5', 3 ', within the above DNA sequences, and combinations thereof allowing for modular cloning.

31. The all-in-one vector of claim 30 wherein the DNA sequence encoding hydroxylation enzymes comprising P4HA1, P4HB, and combinations thereof comprises PHTX1 constitutive bi-directional promoter or PGCW14-PGAP1 constitutive bi-directional promoter.

32. The all-in-one vector of claim 30 wherein the selection marker encodes for antibiotic resistance or an auxotrophic marker.

33. The all-in-one vector of claim 32 wherein the selection marker encoding for antibiotic resistance encodes for resistance to at least one antibiotic selected from the hygromycin, zeocin, geneticin and combinations thereof.

* * * * *

SEQUENCE LISTING

```
<160> NUMBER OF SEQ ID NOS: 25

<210> SEQ ID NO 1
<211> LENGTH: 4401
<212> TYPE: DNA
```

```
<213> ORGANISM: Artificial Sequence
<220> FEATURE:
<223> OTHER INFORMATION: Collagen Sequence 1: cDNA sequence -
      unoptimized natural DNA sequence from cow

<400> SEQUENCE: 1

atgatgagct ttgtgcaaaa ggggacctgg ttacttttcg ctctgcttca tcccactgtt      60

attttggcac aacaggaagc tgttgacgga ggatgctccc atctcggtca gtcttatgca     120

gatagagatg tatggaaacc agaaccgtgc caaatatgcg tctgtgactc aggatccgtt     180

ctctgtgatg acataatatg tgacgaccaa gaattagact gccccaaccc tgaaatcccg     240

tttggagaat gttgtgcagt ttgcccacag cctccaacag ctcccactcg ccctcctaat     300

ggtcaaggac ctcaaggccc caagggagat ccaggtcctc ctggtattcc tgggcgaaat     360

ggcgatcctg gtcctccagg atcaccaggc tccccaggtt ctcccggccc tcctggaatc     420

tgtgaatcat gtcctactgg tggccagaac tattctcccc agtacgaagc atatgatgtc     480

aagtctggag tagcaggagg aggaatcgca ggctatcctg ggccagctgg tcctcctggc     540

ccacccggac cccctggcac atctggccat cctggtgccc ctggcgctcc aggataccaa     600

ggtccccccg gtgaacctgg gcaagctggt ccggcaggtc ctccaggacc tcctggtgct     660

ataggtccat ctggccctgc tggaaaagat ggggaatcag gaagacccgg acgacctgga     720

gagcgaggat ttcctggccc tcctggtatg aaaggcccag ctggtatgcc tggattccct     780

ggtatgaaag gacacagagg ctttgatgga cgaaatggag agaaaggcga aactggtgct     840

cctggattaa aggggggaaaa tggcgttcca ggtgaaaatg gagctcctgg acccatgggt     900

ccaagagggg ctcccggtga gagaggacgg ccaggacttc ctggagccgc aggggctcga     960

ggtaatgatg gagctcgagg aagtgatgga caaccgggcc cccctggtcc tcctggaact    1020

gcaggattcc ctggttcccc tggtgctaag ggtgaagttg gacctgcagg atctcctggt    1080

tcaagtggcg cccctggaca aagaggagaa cctggacctc agggacatgc tggtgctcca    1140

ggtccccctg ggcctcctgg gagtaatggt agtcctggtg gcaaaggtga aatgggtcct    1200

gctggcattc ctggggctcc tgggctgata ggagctcgtg gtcctccagg gccacctggc    1260

accaatggtg ttcccgggca acgaggtgct gcaggtgaac ccggtaagaa tggagccaaa    1320

ggagacccag gaccacgtgg ggaacgcgga gaagctggtt ctccaggtat cgcaggacct    1380

aagggtgaag atggcaaaga tggttctcct ggagaacctg gtgcaaatgg acttcctgga    1440

gctgcaggag aaaggggtgt gcctggattc cgaggacctg ctggagcaaa tggccttcca    1500

ggagaaaagg gtcctcctgg ggaccgtggt ggcccaggcc ctgcagggcc cagaggtgtt    1560

gctggagagc ccggcagaga tggtctccct ggaggtccag gattgagggg tattcctggt    1620

agccccggag gaccaggcag tgatgggaaa ccagggcctc ctggaagcca aggagagacg    1680

ggtcgacccg gtcctccagg ttcacctggt ccgcgaggcc agcctggtgt catgggcttc    1740

cctggtccca aaggaaacga tggtgctcct ggaaaaaatg gagaacgagg tggccctgga    1800

ggtcctggcc ctcagggtcc tgctggaaag aatggtgaga ccggacctca gggtcctcca    1860

ggacctactg gcccttctgg tgacaaagga gacacaggac cccctggtcc acaaggacta    1920

caaggcttgc ctggaacgag tggtccccca ggagaaaacg gaaaacctgg tgaacctggt    1980

ccaaagggtg aggctggtgc acctggaatt ccaggaggca agggtgattc tggtgctccc    2040

ggtgaacgcg gacctcctgg agcaggaggg ccccctggac ctagaggtgg agctggcccc    2100

cctggtcccg aaggaggaaa gggtgctgct ggtccccctg ggccacctgg ttctgctggt    2160
```

```
acacctggtc tgcaaggaat gcctggagaa agagggggtc ctggaggccc tggtccaaag   2220
ggtgataagg gtgagcctgg cagctcaggt gtcgatggtg ctccagggaa agatggtcca   2280
cggggtccca ctggtcccat tggtcctcct ggcccagctg gtcagcctgg agataagggt   2340
gaaagtggtg cccctggagt tccgggtata gctggtcctc gcggtggccc tggtgagaga   2400
ggcgaacagg ggcccccagg acctgctggc ttccctggtg ctcctggcca gaatggtgag   2460
cctggtgcta aaggagaaag aggcgctcct ggtgagaaag gtgaaggagg ccctcccgga   2520
gccgcaggac ccgccggagg ttctgggcct gccggtcccc caggccccca aggtgtcaaa   2580
ggcgaacgtg gcagtcctgg tggtcctggt gctgctggct tccccggtgg tcgtggtcct   2640
cctggccctc ctggcagtaa tggtaaccca ggccccccag gctccagtgg tgctccaggc   2700
aaagatggtc ccccaggtcc acctggcagt aatggtgctc ctggcagccc cgggatctct   2760
ggaccaaagg gtgattctgg tccaccaggt gagaggggag cacctggccc ccagggccct   2820
ccgggagctc caggcccact aggaattgca ggacttactg gagcacgagg tcttgcaggc   2880
ccaccaggca tgccaggtgc taggggcagc cccggcccac agggcatcaa gggtgaaaat   2940
ggtaaaccag gacctagtgg tcagaatgga gaacgtggtc ctcctggccc ccagggtctt   3000
cctggtctgg ctggtacagc tggtgagcct ggaagagatg gaaaccctgg atcagatggt   3060
ctgccaggcc gagatggagc tccaggtgcc aagggtgacc gtggtgaaaa tggctctcct   3120
ggtgcccctg gagctcctgg tcacccaggc cctcctggtc ctgtcggtcc agctggaaag   3180
agcggtgaca gaggagaaac tggccctgct ggtccttctg ggcccccggg tcctgccgga   3240
tcaagaggtc ctcctggtcc ccaaggccca cgcggtgaca aaggggaaac cggtgagcgt   3300
ggtgctatgg gcatcaaagg acatcgcgga ttccctggca acccaggggc cccgggatct   3360
ccgggtcccg ctggtcatca aggtgcagtt ggcagtccag gccctgcagg ccccagagga   3420
cctgttggac ctagcgggcc ccctggaaag gacggagcaa gtggacaccc tggtcccatt   3480
ggaccaccgg ggccccgagg taacagaggt gaaagaggat ctgagggctc cccaggccac   3540
ccaggacaac caggccctcc tggacctcct ggtgcccctg gtccatgttg tggtgctggc   3600
ggggttgctg ccattgctgg tgttggagcc gaaaaagctg gtggttttgc cccatattat   3660
ggagatgaac cgatagattt caaaatcaac accgatgaga ttatgacctc actcaaatca   3720
gtcaatggac aaatagaaag cctcattagt cctgatggtt cccgtaaaaa ccctgcacgg   3780
aactgcaggg acctgaaatt ctgccatcct gaactccaga gtggagaata ttgggttgat   3840
cctaaccaag gttgcaaatt ggatgctatt aaagtctact gtaacatgga aactggggaa   3900
acgtgcataa gtgccagtcc tttgactatc ccacagaaga actggtggac agattctggt   3960
gctgagaaga aacatgtttg gtttggagaa tccatggagg gtggttttca gtttagctat   4020
ggcaatcctg aacttcccga agacgtcctc gatgtccagc tggcattcct ccgacttctc   4080
tccagccggg cctctcagaa catcacatat cactgcaaga atagcattgc atacatggat   4140
catgccagtg ggaatgtaaa gaaagccttg aagctgatgg ggtcaaatga aggtgaattc   4200
aaggctgaag gaaatagcaa attcacatac acagttctgg aggatggttg cacaaaacac   4260
actggggaat ggggcaaaac agtcttccag tatcaaacac gcaaggccgt cagactacct   4320
attgtagata ttgcacccta tgatatcggt ggtcctgatc aagaatttgg tgcggacatt   4380
ggccctgttt gctttttata a                                              4401
```

<210> SEQ ID NO 2
<211> LENGTH: 4404

<212> TYPE: DNA
<213> ORGANISM: Artificial Sequence
<220> FEATURE:
<223> OTHER INFORMATION: Col3A1 cDNA sequence

<400> SEQUENCE: 2

```
atgatgtctt ttgtccaaaa gggtacttgg ttactttttg ctctgttgca cccaactgtt     60

attctcgcac aacaggaagc agtagatggt ggttgctcac atttaggtca atcttacgca    120

gatagagatg tatggaaacc tgaaccatgt caaatttgcg tgtgtgactc aggttcagtg    180

ctctgcgacg atatcatatg tgacgaccag gaattggact gtccaaaccc agagatacca    240

ttcggtgaat gttgtgctgt ttgtccacag ccaccaactg ctcctacaag acctccaaac    300

ggtcaaggtc cacaaggtcc taaaggtgat ccgggtccac ctggtattcc tggtagaaat    360

ggtgaccctg gacctcccgg ttccccaggt agcccaggat cacctgggcc tcctggaata    420

tgtgaatcct gcccaactgg tggtcagaac tatagcccac aatacgaggc ctacgacgtc    480

aaatctggtg ttgctggagg aggtattgca ggctaccctg gtcccgcagg gcccccaggt    540

ccgccgggtc cgcccggaac atcaggtcat cccggagccc ctggtgcacc aggttatcag    600

ggaccgcccg gagagcctgg acaagctggt cccgctggac cccctggtcc accaggtgct    660

attggaccaa gtggtcctgc cggaaaagac ggtgaatccg gtagacctgg tagacccggc    720

gaaaggggtt tcccaggtcc tcccggaatg aagggtccag ccggtatgcc cggttttcct    780

gggatgaagg gtcacagagg atttgatggt agaaacggag agaaaggcga aaccggtgct    840

cccggactga agggtgaaaa cggtgtccct ggtgagaacg gcgctcctgg acctatgggt    900

ccacgtggtg ctccaggaga aagaggcaga ccaggattgc ctggtgcagc tggtgctaga    960

ggtaacgatg gtgcccgtgg ttccgatgga caacccgggc cacccggccc tccaggtacc   1020

gctggatttc ctggaagccc tggtgctaag ggggaggttg gtccggctgg tagtcccgga   1080

agtagcggtg ccccaggtca aagaggcgaa ccaggccctc agggtcacgc aggagcacct   1140

ggaccgcctg gtcctcctgg ttcgaatggt tcgcctggag gaaaaggtga aatggggccc   1200

gcaggaatcc ccggtgcgcc tggtcttatt ggtgccaggg gtcctccagg cccgccaggt   1260

acaaatggtg tacccggaca gcgaggagca gctggtgaac ctggtaaaaa cggtgccaaa   1320

ggagatccag gtcctcgtgg agagcgtggt gaagctggct ctcccggtat cgccggtcca   1380

aaaggtgagg acggtaagga cggttcccct ggtgagccag gtgcgaacgg actgccaggt   1440

gcagccggag agcgaggagt cccaggattc aggggaccag ccggtgctaa cggcttgcct   1500

ggtgaaaaag ggcccccctgg tgatagggga ggacccggtc cagcaggccc tcgtggagtt   1560

gctggtgagc ctggacgtga cggtttacca ggagggccag gtttgagggg tattcccggg   1620

tcccctggcg gtcctggatc ggatggaaaa ccagggccac caggttcgca gggtgaaaca   1680

ggacgtccag gcccacccgg ctcacctggt ccaaggggtc agcctggtgt catgggtttc   1740

cccggtccaa agggtaatga cggagcaccg ggtaaaaatg gtgaacgtgg tggcccaggt   1800

ggtccaggac cccaaggtcc agctggaaaa aacggtgaga caggtcctca aggacctcca   1860

ggacctaccg gtcctagcgg agataaggga gatacgggac cgccaggacc tcaaggattg   1920

caaggtttgc ctggtacatc tggccctccc ggagaaaatg gtaagcctgg agagccagga   1980

ccaaaaggcg aagctggagc cccaggtatc cccggaggta agggagactc aggtgctccg   2040

ggtgagcgtg gtcctccggg tgccggtggt ccacctggac ctagaggtgg tgccgggccg   2100

ccaggtcctg aaggtggtaa aggtgctgct ggtccaccgg gaccgcctgg ctctgctggt   2160
```

actcctggct tgcagggaat gccaggagag agaggtggac ctggaggtcc cggtccgaag 2220
ggtgataaag gggagccagg atcatccggt gttgacggcg cacctggtaa agacggacca 2280
aggggaccaa cgggtccaat cggaccacca ggacccgctg gccagccagg agataaaggc 2340
gagtccggag cacccggtgt tcctggtata gctggaccca ggggtggtcc cggtgaaaga 2400
ggtgaacagg gcccaccggg tcccgccggt ttccctggcg cccctggtca aaatggagaa 2460
ccaggtgcaa agggcgagag aggagcccca ggagaaaagg gtgagggagg accacccggt 2520
gctgccggtc cagctggggg ttcaggtcct gctggaccac caggtccaca gggcgttaaa 2580
ggtgagagag gaagtccagg tggtcctgga gctgctggat tcccaggtgg ccgtggacct 2640
cctggtcccc ctggatcgaa tggtaatcct ggtccgccag gtagttcggg tgctcctggg 2700
aaggacggtc cacctggccc cccaggtagt aacggtgcac ctggtagtcc aggtatatcc 2760
ggacctaaag gagattccgg tccaccaggc gaaagagggg ccccaggccc acagggtcca 2820
ccaggagccc ccggtcctct gggtattgct ggtcttactg gtgcacgtgg actggccggt 2880
ccacccggaa tgcctggagc aagaggttca cctggaccac aaggtattaa aggagagaac 2940
ggtaaacctg gaccttccgg tcaaaacgga gagcggggac ccccaggccc ccaaggtctg 3000
ccaggactag ctggtaccgc aggggaacca ggaagagatg gaaatccagg ttcagacgga 3060
ctacccggta gagatggtgc accgggggcc aagggcgaca ggggtgagaa tggatctcct 3120
ggtgcgccag gggcaccagg ccacccaggt cccccaggtc ctgtgggccc tgctggaaag 3180
tcaggtgaca ggggagagac aggcccggct ggtccatctg gcgcacccgg accagctggt 3240
tccagaggcc cacctggtcc gcaaggccct agaggtgaca agggagagac tggagaacga 3300
ggtgctatgg gtatcaaggg tcatagaggt tttccgggta atcccggcgc cccaggttct 3360
cctggtccag ctggccatca aggtgcagtc ggatcgcccg gcccagccgg tcccaggggc 3420
cctgttggtc catccggtcc tccaggaaag gatggtgctt ctggacaccc aggacctatc 3480
ggacctccgg gtcctagagg taatagagga gaacgtggat ccgagggtag tcctggtcac 3540
cctggtcaac ctggcccacc agggcctcca ggtgcacccg gtccatgttg tggtgcaggc 3600
ggtgtggctg caattgctgg tgtgggtgct gaaaaggccg gcggtttcgc tccatattat 3660
ggtgatgaac cgattgattt taagatcaat actgacgaaa tcatgacttc cttaaagtcc 3720
gttaatggtc aaattgagtc tctaatctcc ccagatggtt cacgtaaaaa tcctgctaga 3780
aattgtagag atttgaagtt ttgtcacccc gagttgcagt ccggtgagta ctgggtggac 3840
cccaatcaag gttgtaagtt agacgctatt aaagtttact gcaatatgga gacaggagaa 3900
acttgcatca gcgcttctcc attgactatc ccacaaaaaa attggtggac tgactctgga 3960
gctgagaaaa agcatgtatg gttcggggaa tcgatggaag gtggtttcca attcagctac 4020
ggtaaccctg aacttcctga agatgttctt gacgttcaat tggcatttct gagattgttg 4080
tccagtcgtg caagccaaaa cattacatac cattgcaaaa attccatcgc atatatggat 4140
catgctagcg gaaatgtgaa aaaggcattg aagctgatgg gatcaaatga aggtgaattt 4200
aaagcagagg gtaattctaa gtttacttac actgtattgg aggatggttg tacgaagcat 4260
acaggtgaat ggggtaaaac agtgtttcaa tatcaaaccc gcaaagcagt tagattgcca 4320
atcgtcgata tcgcaccata cgacattgga ggaccagatc aagagttcgg agctgacatc 4380
ggtccggtgt gtttcctttg ataa 4404

<210> SEQ ID NO 3
<211> LENGTH: 940

-continued

<212> TYPE: DNA
<213> ORGANISM: Artificial Sequence
<220> FEATURE:
<223> OTHER INFORMATION: pAOX1

<400> SEQUENCE: 3
agatctaaca tccaaagacg aaaggttgaa tgaaaccttt ttgccatccg acatccacag 60
gtccattctc acacataagt gccaaacgca acaggagggg atacactagc agcagaccgt 120
tgcaaacgca ggacctccac tcctcttctc ctcaacaccc acttttgcca tcgaaaaacc 180
agcccagtta ttgggcttga ttggagctcg ctcattccaa ttccttctat taggctacta 240
acaccatgac tttattagcc tgtctatcct ggcccccctg gcgaggttca tgtttgttta 300
tttccgaatg caacaagctc cgcattacac ccgaacatca ctccagatga gggctttctg 360
agtgtggggt caaatagttt catgttcccc aaatggccca aaactgacag tttaaacgct 420
gtcttggaac ctaatatgac aaaagcgtga tctcatccaa gatgaactaa gtttggttcg 480
ttgaaatgct aacggccagt tggtcaaaaa gaaacttcca aaagtcggca taccgtttgt 540
cttgtttggt attgattgac gaatgctcaa aaataatctc attaatgctt agcgcagtct 600
ctctatcgct tctgaacccc ggtgcacctg tgccgaaacg caaatgggga aacacccgct 660
ttttggatga ttatgcattg tctccacatt gtatgcttcc aagattctgg tgggaatact 720
gctgatagcc taacgttcat gatcaaaatt taactgttct aacccctact tgacagcaat 780
atataaacag aaggaagctg ccctgtctta aacctttttt tttatcatca ttattagctt 840
actttcataa ttgcgactgg ttccaattga caagcttttg attttaacga cttttaacga 900
caacttgaga agatcaaaaa acaactaatt attcgaaacg 940

<210> SEQ ID NO 4
<211> LENGTH: 1612
<212> TYPE: DNA
<213> ORGANISM: Artificial Sequence
<220> FEATURE:
<223> OTHER INFORMATION: Bovine P4HA cDNA Optimized

<400> SEQUENCE: 4
atgatttggt atatcctagt cgttggtatt ttgttgccac agtcactggc tcacccaggc 60
ttcttcactt ctataggaca gatgactgat ttgattcaca cagaaaaaga cctagttaca 120
agccttaaag actatatcaa agctgaagag gataagttgg agcaaatcaa aaagtgggca 180
gagaaactcg atagattgac tagtactgca acaaaagatc ctgagggttt tgtgggtcac 240
ccagtgaatg ctttcaagct gatgaagaga cttaatacag agtggtcaga attggaaaac 300
ttggtactta aagatatgag tgatggattc atttctaact taacaattca aagacaatac 360
tttccaaacg atgaggacca agtaggagca gcaaaagctt tgttgcgatt gcaggacaca 420
tacaatttgg acaccgacac gatatcgaag ggtgatttac ctggtgtgaa gcataagtcc 480
ttcctcactg tggaagattg ttttgaattg ggaaaagtcg catatacaga agccgactac 540
tatcacacag aattatggat ggagcaagct ctgcgtcagt tggacgaagg tgaagtttct 600
accgttgata aggtttcagt tttggattac ttatcatacg ctgtttacca gcaaggtgat 660
ctggacaaag ctctactttt aactaaaaag ttgttggagc tggacccgga gcatcaaaga 720
gctaacggta atctgaaata ctttgaatac atcatggcta aggaaaagga cgcaaataag 780
tcctcgtccg atgaccaatc cgatcaaaag accactctga aaaaaaaagg tgcagctgtt 840
gactacctcc cagagagaca aaagtatgaa atgctgtgta gaggagaggg tatcaagatg 900

```
actccaagga gacagaaaaa gctgttctgt agatatcatg atgggaaccg taacccaaaa    960

ttcattcttg ctccagcgaa acaggaagat gaatgggaca agcctagaat cattcgtttt   1020

catgacatca tctccgatgc agaaatagag gttgtgaaag acttggccaa accaagattg   1080

agtagggcta ccgtccatga ccctgagact ggaaaattga ctaccgcaca atatcgtgtc   1140

tctaaatcag catggttgtc cggttacgag aatcccgtgg tcagccgtat caatatgcgt   1200

attcaagatt tgactggtct tgacgtaagc actgctgagg aactacaagt tgccaactat   1260

ggtgtgggcg gtcagtatga accccacttt gatttcgcca gaaaggacga gcctgatgct   1320

tttaaggagc taggtactgg aaatagaatc gcaacgtggt tgttctatat gtccgatgtg   1380

cttgctggag gagccacagt tttccctgag gtaggtgctt ctgtttggcc taaaaagggc   1440

acggccgtat tttggtacaa tctgtttgca tctggagaag gtgattacag cactagacat   1500

gctgcttgtc ccgtcttagt cggtaataag tgggtttcca ataagtggct gcatgagaga   1560

ggtcaagagt ttaggaggcc atgcacattg tcagaattag aatgataatt tt           1612
```

<210> SEQ ID NO 5
<211> LENGTH: 1750
<212> TYPE: DNA
<213> ORGANISM: Artificial Sequence
<220> FEATURE:
<223> OTHER INFORMATION: Bovine P4HB (PDI) sequence, with Alpha pre-pro signal sequence

<400> SEQUENCE: 5

```
aaaatgagat tcccatctat tttcaccgct gtcttgttcg ctgcctcctc tgcattggct     60

gcccctgtta acactaccac tgaagacgag actgctcaaa ttccagctga agcagttatc    120

ggttactctg accttgaggg tgatttcgac gtcgctgttt tgcctttctc taactccact    180

aacaacggtt tgttgttcat taacaccact atcgcttcca ttgctgctaa ggaagagggt    240

gtctctctcg agaaaagaga ggccgaagct gcacccgatg aggaagatca tgttttagta    300

ttgcataaag gaaatttcga tgaagctttg gccgctcaca aatatctgct cgtcgagttt    360

tacgctccct ggtgcggtca ttgtaaggcc cttgcaccag agtacgccaa ggcagctggt    420

aagttaaagg ccgaaggttc agagatcaga ttagcaaaag ttgatgctac agaagagtcc    480

gatcttgctc aacaatacgg ggttcgagga tacccaacaa ttaagttttt caaaaatggt    540

gatactgctt ccccaaagga atatactgct ggtagagagg cagacgacat agtcaactgg    600

ctcaaaaaga gaacgggccc agctgcgtct acattaagcg acggagcagc agccgaagct    660

cttgtggaat ctagtgaagt tgctgtaatc ggtttcttta aggacatgga atctgattca    720

gctaaacagt tccttttagc agctgaagca atcgatgaca tccctttcgg aatcacctca    780

aatagtgacg tgttcagcaa gtaccaactt gacaaagatg gagtggtctt gttcaaaaag    840

tttgacgaag gcagaaacaa tttcgagggt gaggttacaa aggagaaact gcttgatttc    900

attaaacata accaactacc cttagttatc gaattcactg aacaaactgc tcctaagatt    960

ttcggtggag aaatcaaaac acatatcttg ttgtttttgc caaagtccgt atcggattat   1020

gaaggtaaac tctccaattt caaaaaggcc gctgagagct ttaagggcaa gattttgttc   1080

atctttattg actcagacca cacagacaat cagaggattt tggagttttt cggtttgaaa   1140

aaggaggaat gtccagcagt ccgtttgatc accttggagg aggagatgac caaatacaaa   1200

ccagagtcgg atgagttgac tgccgagaag ataacagaat tttgtcacag atttctggaa   1260

ggtaagatca agcctcatct tatgtctcaa gagttgcctg atgactggga taagcaacca   1320
```

```
gttaaagtat tggtgggtaa aaactttgag gaagtggcct tcgacgagaa aaaaaatgtc   1380

tttgttgaat tctatgctcc gtggtgtggt cactgtaagc agctggcacc aatttgggat   1440

aaactgggtg aaacttacaa agatcacgaa aacattgtta ttgcaaagat ggacagtact   1500

gctaacgaag tggaggctgt gaaagttcac tccttcccta cgctgaagtt ctttcctgca   1560

tctgctgaca gaactgttat cgactataat ggagagagga cattggatgg ttttaaaaag   1620

tttcttgaat ccggaggtca agacggagct ggtgacgacg atgatttgga agatctggag   1680

gaggctgagg aacctgatct tgaggaggat gacgaccaga aggcagtcaa agatgaactg   1740

tgataagggg                                                          1750
```

```
<210> SEQ ID NO 6
<211> LENGTH: 7479
<212> TYPE: DNA
<213> ORGANISM: Artificial Sequence
<220> FEATURE:
<223> OTHER INFORMATION: Collagen expression vectors - pDF-Col3A1

<400> SEQUENCE: 6

ggatccttca gtaatgtctt gtttcttttg ttgcagtggt gagccatttt gacttcgtga     60

aagtttcttt agaatagttg tttccagagg ccaaacattc cacccgtagt aaagtgcaag    120

cgtaggaaga ccaagactgg cataaatcag gtataagtgt cgagcactgg caggtgatct    180

tctgaaagtt tctactagca gataagatcc agtagtcatg catatggcaa caatgtaccg    240

tgtggatcta agaacgcgtc ctactaacct tcgcattcgt tggtccagtt tgttgttatc    300

gatcaacgtg acaaggttgt cgattccgcg taagcatgca tacccaagga cgcctgttgc    360

aattccaagt gagccagttc caacaatctt tgtaatatta gagcacttca ttgtgttgcg    420

cttgaaagta aaatgcgaac aaattaagag ataatctcga aaccgcgact tcaaacgcca    480

atatgatgtg cggcacacaa taagcgttca tatccgctgg gtgactttct cgctttaaaa    540

aattatccga aaaaatttc tagagtgttg ttactttata cttccggctc gtataatacg     600

acaaggtgta aggaggacta aaccatggct aaactcacct ctgctgttcc agtcctgact    660

gctcgtgatg ttgctggtgc tgttgagttc tggactgata ggctcggttt ctcccgtgac    720

ttcgtagagg acgactttgc cggtgttgta cgtgacgacg ttaccctgtt catctccgca    780

gttcaggacc aggttgtgcc agacaacact ctggcatggg tatgggttcg tggtctggac    840

gaactgtacg ctgagtggtc tgaggtcgtg tctaccaact tccgtgatgc atctggtcca    900

gctatgaccg agatcggtga acagccctgg ggtcgtgagt ttgcactgcg tgatccagct    960

ggtaactgcg tgcatttcgt cgcagaagag caggactaac aattgacacc ttacgattat   1020

ttagagagta tttattagtt ttattgtatg tatacggatg ttttattatc tatttatgcc   1080

cttatattct gtaactatcc aaaagtccta tcttatcaag ccagcaatct atgtccgcga   1140

acgtcaacta aaaataagct ttttatgctc ttctctcttt ttttcccttc ggtataatta   1200

taccttgcat ccacagattc tcctgccaaa ttttgcataa tcctttacaa catggctata   1260

tgggagcact tagcgccctc caaaacccat attgcctacg catgtatagg tgtttttttcc  1320

acaatatttt ctctgtgctc tctttttatt aaagagaagc tctatatcgg agaagcttct   1380

gtggccgtta tattcggcct tatcgtggga ccacattgcc tgaattggtt tgccccggaa   1440

gattggggaa acttggatct gattacctta gctgcagaaa agggtaccac tgagcgtcag   1500

accccgtaga aaagatcaaa ggatcttctt gagatccttt ttttctgcgc gtaatctgct   1560

gcttgcaaac aaaaaaacca ccgctaccag cggtggtttg tttgccggat caagagctac   1620
```

-continued

```
caactctttt tccgaaggta actggcttca gcagagcgca gataccaaat actgttcttc   1680
tagtgtagcc gtagttaggc caccacttca agaactctgt agcaccgcct acatacctcg   1740
ctctgctaat cctgttacca gtggctgctg ccagtggcga taagtcgtgt cttaccgggt   1800
tggacccaag acgatagtta ccggataagg cgcagcggtc gggctgaacg gggggttcgt   1860
gcacacagcc cagcttggag cgaacgacct acaccgaact gagataccta cagcgtgagc   1920
tatgagaaag cgccacgctt cccgaaggga gaaaggcgga caggtatccg gtaagcggca   1980
gggtcggaac aggagagcgc acgagggagc ttccaggggg aaacgcctgg tatctttata   2040
gtcctgtcgg gtttcgccac ctctgacttg agcgtcgatt tttgtgatgc tcgtcagggg   2100
ggcggagcct atggaaaaac gccagcaacg cggccttttt acggttcctg gccttttgct   2160
ggccttttgc tcacatgtat ttaaataatg tatctaaacg caaactccga gctggaaaaa   2220
tgttaccggc gatgcgcgga caatttagag gcggcgatca agaaacacct gctgggcgag   2280
cagtctggag cacagtcttc gatgggcccg agatcccacc gcgttcctgg gtaccgggac   2340
gtgaggcagc gcgacatcca tcaaatatac caggcgccaa ccgagtctct cggaaaacag   2400
cttctggata tcttccgctg gcggcgcaac gacgaataat agtccctgga ggtgacggaa   2460
tatatatgtg tggagggtaa atctgacagg gtgtagcaaa ggtaatattt tcctaaaaca   2520
tgcaatcggc tgccccgcaa cgggaaaaag aatgactttg gcactcttca ccagagtggg   2580
gtgtcccgct cgtgtgtgca aataggctcc cactggtcac cccggatttt gcagaaaaac   2640
agcaagttcc ggggtgtctc actggtgtcc gccaataaga ggagccggca ggcacggagt   2700
ctacatcaag ctgtctccga tacactcgac taccatccgg gtctctcaga gaggggaatg   2760
gcactataaa taccgcctcc ttgcgctctc tgccttcatc aatcaaatca tgatgtcttt   2820
tgtccaaaag ggtacttggt tactttttgc tctgttgcac ccaactgtta ttctcgcaca   2880
acaggaagca gtagatggtg gttgctcaca tttaggtcaa tcttacgcag atagagatgt   2940
atggaaacct gaaccatgtc aaatttgcgt gtgtgactca ggttcagtgc tctgcgacga   3000
tatcatatgt gacgaccagg aattggactg tccaaaccca gagataccat tcggtgaatg   3060
ttgtgctgtt tgtccacagc caccaactgc tcctacaaga cctccaaacg gtcaaggtcc   3120
acaaggtcct aaaggtgatc cgggtccacc tggtattcct ggtagaaatg gtgaccctgg   3180
acctcccggt tccccaggta gcccaggatc acctgggcct cctggaatat gtgaatcctg   3240
cccaactggt ggtcagaact atagcccaca atacgaggcc tacgacgtca aatctggtgt   3300
tgctggagga ggtattgcag gctaccctgg tcccgcaggg cccccaggtc cgccgggtcc   3360
gcccggaaca tcaggtcatc ccggagcccc tggtgcacca ggttatcagg gaccgcccgg   3420
agagcctgga caagctggtc ccgctggacc ccctggtcca ccaggtgcta ttggaccaag   3480
tggtcctgcc ggaaaagacg gtgaatccgg tagacctggt agacccggcg aaaggggttt   3540
cccaggtcct cccggaatga agggtccagc cggtatgccc ggttttcctg ggatgaaggg   3600
tcacagagga tttgatggta gaaacggaga gaaaggcgaa accggtgctc ccggactgaa   3660
gggtgaaaac ggtgtccctg gtgagaacgg cgctcctgga cctatgggtc cacgtggtgc   3720
tccaggagaa agaggcagac caggattgcc tggtgcagct ggtgctagag gtaacgatgg   3780
tgcccgtggt tccgatggac aacccgggcc acccggccct ccaggtaccg ctggatttcc   3840
tggaagccct ggtgctaagg gggaggttgg tccggctggt agtcccggaa gtagcggtgc   3900
cccaggtcaa agaggcgaac caggccctca gggtcacgca ggagcacctg gaccgcctgg   3960
```

-continued

```
tcctcctggt tcgaatggtt cgcctggagg aaaaggtgaa atggggcccg caggaatccc   4020
cggtgcgcct ggtcttattg gtgccagggg tcctccaggc ccgccaggta caaatggtgt   4080
acccggacag cgaggagcag ctggtgaacc tggtaaaaac ggtgccaaag gagatccagg   4140
tcctcgtgga gagcgtggtg aagctggctc tcccggtatc gccggtccaa aaggtgagga   4200
cggtaaggac ggttcccctg gtgagccagg tgcgaacgga ctgccaggtg cagccggaga   4260
gcgaggagtc ccaggattca ggggaccagc cggtgctaac ggcttgcctg gtgaaaaagg   4320
gccccctggt gataggggag gacccggtcc agcaggccct cgtggagttg ctggtgagcc   4380
tggacgtgac ggtttaccag gagggccagg tttgaggggt attcccgggt cccctggcgg   4440
tcctggatcg gatggaaaac cagggccacc aggttcgcag ggtgaaacag gacgtccagg   4500
cccacccggc tcacctggtc caaggggtca gcctggtgtc atgggtttcc ccggtccaaa   4560
gggtaatgac ggagcaccgg gtaaaaatgg tgaacgtggt ggcccaggtg gtccaggacc   4620
ccaaggtcca gctggaaaaa acggtgagac aggtcctcaa ggacctccag gacctaccgg   4680
tcctagcgga gataagggag atacgggacc gccaggacct caaggattgc aaggtttgcc   4740
tggtacatct ggccctcccg gagaaaatgg taagcctgga gagccaggac caaaaggcga   4800
agctggagcc ccaggtatcc ccggaggtaa gggagactca ggtgctccgg gtgagcgtgg   4860
tcctccgggt gccggtggtc cacctggacc tagaggtggt gccgggccgc caggtcctga   4920
aggtggtaaa ggtgctgctg gtccaccggg accgcctggc tctgctggta ctcctggctt   4980
gcagggaatg ccaggagaga gaggtggacc tggaggtccc ggtccgaagg gtgataaagg   5040
ggagccagga tcatccggtg ttgacggcgc acctggtaaa gacggaccaa ggggaccaac   5100
gggtccaatc ggaccaccag gacccgctgg ccagccagga gataaaggcg agtccggagc   5160
acccggtgtt cctggtatag ctggacccag ggtggtccc ggtgaaagag gtgaacaggg   5220
cccaccgggt cccgccggtt tccctggcgc ccctggtcaa aatggagaac caggtgcaaa   5280
gggcgagaga ggagccccag gagaaaaggg tgagggagga ccacccggtg ctgccggtcc   5340
agctgggggt tcaggtcctg ctggaccacc aggtccacag ggcgttaaag gtgagagagg   5400
aagtccaggt ggtcctggag ctgctggatt cccaggtggc cgtggacctc ctggtccccc   5460
tggatcgaat ggtaatcctg gtccgccagg tagttcgggt gctcctggga aggacggtcc   5520
acctggcccc ccaggtagta acggtgcacc tggtagtcca ggtatatccg gacctaaagg   5580
agattccggt ccaccaggcg aaagaggggc cccaggccca cagggtccac caggagcccc   5640
cggtcctctg ggtattgctg gtcttactgg tgcacgtgga ctggccggtc cacccggaat   5700
gcctggagca agaggttcac ctggaccaca aggtattaaa ggagagaacg gtaaacctgg   5760
accttccggt caaaacggag agcggggacc cccaggcccc caaggtctgc caggactagc   5820
tggtaccgca ggggaaccag gaagagatgg aaatccaggt tcagacggac tacccggtag   5880
agatggtgca ccgggggcca agggcgacag gggtgagaat ggatctcctg gtgcgccagg   5940
ggcaccaggc cacccaggtc cccaggtcc tgtgggccct gctggaaagt caggtgacag   6000
gggagagaca ggcccggctg gtccatctgg cgcacccgga ccagctggtt ccagaggccc   6060
acctggtccg caaggcccta gaggtgacaa gggagagact ggagaacgag gtgctatggg   6120
tatcaagggt catagaggtt ttccgggtaa tcccggcgcc ccaggttctc ctggtccagc   6180
tggccatcaa ggtgcagtcg gatcgcccgg cccagccggt cccaggggcc ctgttggtcc   6240
atccggtcct ccaggaaagg atggtgcttc tggacaccca ggacctatcg gacctccggg   6300
tcctagaggt aatagaggag aacgtggatc cgagggtagt cctggtcacc ctggtcaacc   6360
```

-continued tggcccacca gggcctccag gtgcacccgg tccatgttgt ggtgcaggcg gtgtggctgc 6420
aattgctggt gtgggtgctg aaaaggccgg cggtttcgct ccatattatg gtgatgaacc 6480
gattgatttt aagatcaata ctgacgaaat catgacttcc ttaaagtccg ttaatggtca 6540
aattgagtct ctaatctccc cagatggttc acgtaaaaat cctgctagaa attgtagaga 6600
tttgaagttt tgtcaccccg agttgcagtc cggtgagtac tgggtggacc ccaatcaagg 6660
ttgtaagtta gacgctatta aagtttactg caatatggag acaggagaaa cttgcatcag 6720
cgcttctcca ttgactatcc cacaaaaaaa ttggtggact gactctggag ctgagaaaaa 6780
gcatgtatgg ttcggggaat cgatggaagg tggtttccaa ttcagctacg gtaaccctga 6840
acttcctgaa gatgttcttg acgttcaatt ggcatttctg agattgttgt ccagtcgtgc 6900
aagccaaaac attacatacc attgcaaaaa ttccatcgca tatatggatc atgctagcgg 6960
aaatgtgaaa aaggcattga agctgatggg atcaaatgaa ggtgaattta aagcagaggg 7020
taattctaag tttacttaca ctgtattgga ggatggttgt acgaagcata caggtgaatg 7080
gggtaaaaca gtgtttcaat atcaaacccg caaagcagtt agattgccaa tcgtcgatat 7140
cgcaccatac gacattggag gaccagatca agagttcgga gctgacatcg gtccggtgtg 7200
tttcctttga taatcaagag gatgtcagaa tgccatttgc ctgagagatg caggcttcat 7260
ttttgatact tttttatttg taacctatat agtataggat ttttttgtc attttgtttc 7320 ttctcgtacg agcttgctcc tgatcagcct atctcgcagc tgatgaatat cttgtggtag 7380
gggtttggga aaatcattcg agtttgatgt ttttcttggt atttcccact cctcttcaga 7440
gtacagaaga ttaagtgaga cgttcgtttg tgctccgga 7479

<210> SEQ ID NO 7
<211> LENGTH: 7356
<212> TYPE: DNA
<213> ORGANISM: Artificial Sequence
<220> FEATURE:
<223> OTHER INFORMATION: Collagen expression vectors - pCAT1-Col3A1

<400> SEQUENCE: 7
ggatccttca gtaatgtctt gtttcttttg ttgcagtggt gagccatttt gacttcgtga 60
aagtttcttt agaatagttg tttccagagg ccaaacattc cacccgtagt aaagtgcaag 120
cgtaggaaga ccaagactgg cataaatcag gtataagtgt cgagcactgg caggtgatct 180
tctgaaagtt tctactagca gataagatcc agtagtcatg catatggcaa caatgtaccg 240
tgtggatcta agaacgcgtc ctactaacct tcgcattcgt tggtccagtt tgttgttatc 300
gatcaacgtg acaaggttgt cgattccgcg taagcatgca tacccaagga cgcctgttgc 360
aattccaagt gagccagttc caacaatctt tgtaatatta gagcacttca ttgtgttgcg 420
cttgaaagta aaatgcgaac aaattaagag ataatctcga aaccgcgact tcaaacgcca 480
atatgatgtg cggcacacaa taagcgttca tatccgctgg gtgactttct cgctttaaaa 540
aattatccga aaaaatttc tagagtgttg ttactttata cttccggctc gtataatacg 600
acaaggtgta aggaggacta aaccatggct aaactcacct ctgctgttcc agtcctgact 660
gctcgtgatg ttgctggtgc tgttgagttc tggactgata ggctcggttt ctcccgtgac 720
ttcgtagagg acgactttgc cggtgttgta cgtgacgacg ttaccctgtt catctccgca 780
gttcaggacc aggttgtgcc agacaacact ctggcatggg tatgggttcg tggtctggac 840
gaactgtacg ctgagtggtc tgaggtcgtg tctaccaact tccgtgatgc atctggtcca 900

-continued

```
gctatgaccg agatcggtga acagccctgg ggtcgtgagt ttgcactgcg tgatccagct    960
ggtaactgcg tgcatttcgt cgcagaagag caggactaac aattgacacc ttacgattat   1020
ttagagagta tttattagtt ttattgtatg tatacggatg ttttattatc tatttatgcc   1080
cttatattct gtaactatcc aaaagtccta tcttatcaag ccagcaatct atgtccgcga   1140
acgtcaacta aaaataagct ttttatgctc ttctctcttt ttttcccttc ggtataatta   1200
taccttgcat ccacagattc tcctgccaaa ttttgcataa tcctttacaa catggctata   1260
tgggagcact tagcgccctc caaaacccat attgcctacg catgtatagg tgtttttttcc  1320
acaatatttt ctctgtgctc tctttttatt aaagagaagc tctatatcgg agaagcttct   1380
gtggccgtta tattcggcct tatcgtggga ccacattgcc tgaattggtt tgccccggaa   1440
gattggggaa acttggatct gattacctta gctgcagaaa agggtaccac tgagcgtcag   1500
accccgtaga aaagatcaaa ggatcttctt gagatccttt ttttctgcgc gtaatctgct   1560
gcttgcaaac aaaaaaacca ccgctaccag cggtggtttg tttgccggat caagagctac   1620
caactctttt tccgaaggta actggcttca gcagagcgca gataccaaat actgttcttc   1680
tagtgtagcc gtagttaggc caccacttca agaactctgt agcaccgcct acatacctcg   1740
ctctgctaat cctgttacca gtggctgctg ccagtggcga taagtcgtgt cttaccgggt   1800
tggacccaag acgatagtta ccggataagg cgcagcggtc gggctgaacg gggggttcgt   1860
gcacacagcc cagcttggag cgaacgacct acaccgaact gagataccta cagcgtgagc   1920
tatgagaaag cgccacgctt cccgaaggga gaaaggcgga caggtatccg gtaagcggca   1980
gggtcggaac aggagagcgc acgagggagc ttccaggggg aaacgcctgg tatctttata   2040
gtcctgtcgg gtttcgccac ctctgacttg agcgtcgatt tttgtgatgc tcgtcagggg   2100
ggcggagcct atggaaaaac gccagcaacg cggccttttt acggttcctg gccttttgct   2160
ggccttttgc tcacatgtat ttaaattaat cgaactccga atgcggttct cctgtaacct   2220
taattgtagc atagatcact taaataaact catggcctga catctgtaca cgttcttatt   2280
ggtcttttag caatcttgaa gtctttctat tgttccggtc ggcattacct aataaattcg   2340
aatcgagatt gctagtacct gatatcatat gaagtaatca tcacatgcaa gttccatgat   2400
accctctact aatggaattg aacaaagttt aagcttctcg cacgagaccg aatccatact   2460
atgcacccct caaagttggg attagtcagg aaagctgagc aattaacttc cctcgattgg   2520
cctggacttt tcgcttagcc tgccgcaatc ggtaagtttc attatcccag cggggtgata   2580
gcctctgttg ctcatcaggc caaaatcata tataagctgt agacccagca cttcaattac   2640
ttgaaattca ccataacact tgctctagtc aagacttaca attaaaatga tgtcttttgt   2700
ccaaaagggt acttggttac tttttgctct gttgcaccca actgttattc tcgcacaaca   2760
ggaagcagta gatggtggtt gctcacattt aggtcaatct tacgcagata gagatgtatg   2820
gaaacctgaa ccatgtcaaa tttgcgtgtg tgactcaggt tcagtgctct gcgacgatat   2880
catatgtgac gaccaggaat tggactgtcc aaacccagag ataccattcg gtgaatgttg   2940
tgctgtttgt ccacagccac caactgctcc tacaagacct ccaaacggtc aaggtccaca   3000
aggtcctaaa ggtgatccgg gtccacctgg tattcctggt agaaatggtg accctggacc   3060
tcccggttcc ccaggtagcc caggatcacc tgggcctcct ggaatatgtg aatcctgccc   3120
aactggtggt cagaactata gcccacaata cgaggcctac gacgtcaaat ctggtgttgc   3180
tggaggaggt attgcaggct accctggtcc cgcagggccc ccaggtccgc cgggtccgcc   3240
cggaacatca ggtcatcccg gagcccctgg tgcaccaggt tatcagggac cgcccggaga   3300
```

-continued gcctggacaa gctggtcccg ctggaccccc tggtccacca ggtgctattg gaccaagtgg 3360
tcctgccgga aaagacggtg aatccggtag acctggtaga cccggcgaaa ggggtttccc 3420
aggtcctccc ggaatgaagg gtccagccgg tatgcccggt tttcctggga tgaagggtca 3480
cagaggattt gatggtagaa acggagagaa aggcgaaacc ggtgctcccg gactgaaggg 3540
tgaaaacggt gtccctggtg agaacggcgc tcctggacct atgggtccac gtggtgctcc 3600
aggagaaaga ggcagaccag gattgcctgg tgcagctggt gctagaggta acgatggtgc 3660
ccgtggttcc gatggacaac ccgggccacc cggccctcca ggtaccgctg gatttcctgg 3720
aagccctggt gctaaggggg aggttggtcc ggctggtagt cccggaagta gcggtgcccc 3780
aggtcaaaga ggcgaaccag gccctcaggg tcacgcagga gcacctggac cgcctggtcc 3840
tcctggttcg aatggttcgc ctggaggaaa aggtgaaatg ggcccgcag gaatccccgg 3900 tgcgcctggt cttattggtg ccaggggtcc tccaggcccg ccaggtacaa atggtgtacc 3960
cggacagcga ggagcagctg gtgaacctgg taaaaacggt gccaaaggag atccaggtcc 4020
tcgtggagag cgtggtgaag ctggctctcc cggtatcgcc ggtccaaaag gtgaggacgg 4080
taaggacggt tcccctggtg agccaggtgc gaacggactg ccaggtgcag ccggagagcg 4140
aggagtccca ggattcaggg gaccagccgg tgctaacggc ttgcctggtg aaaaagggcc 4200
ccctggtgat aggggaggac ccggtccagc aggccctcgt ggagttgctg gtgagcctgg 4260
acgtgacggt ttaccaggag ggccaggttt gaggggtatt cccgggtccc ctggcggtcc 4320
tggatcggat ggaaaaccag ggccaccagg ttcgcagggt gaaacaggac gtccaggccc 4380
acccggctca cctggtccaa ggggtcagcc tggtgtcatg ggtttccccg gtccaaaggg 4440
taatgacgga gcaccgggta aaaatggtga acgtggtggc ccaggtggtc caggacccca 4500
aggtccagct ggaaaaaacg gtgagacagg tcctcaagga cctccaggac ctaccggtcc 4560
tagcggagat aagggagata cgggaccgcc aggacctcaa ggattgcaag gtttgcctgg 4620
tacatctggc cctcccggag aaaatggtaa gcctggagag ccaggaccaa aaggcgaagc 4680
tggagcccca ggtatccccg gaggtaaggg agactcaggt gctccgggtg agcgtggtcc 4740
tccgggtgcc ggtggtccac ctggacctag aggtggtgcc gggccgccag gtcctgaagg 4800
tggtaaaggt gctgctggtc caccgggacc gcctggctct gctggtactc ctggcttgca 4860
gggaatgcca ggagagagag gtggacctgg aggtcccggt ccgaagggtg ataaagggga 4920
gccaggatca tccggtgttg acggcgcacc tggtaaagac ggaccaaggg gaccaacggg 4980
tccaatcgga ccaccaggac ccgctggcca gccaggagat aaaggcgagt ccggagcacc 5040
cggtgttcct ggtatagctg gacccagggg tggtcccggt gaaagaggtg aacagggccc 5100
accgggtccc gccggtttcc ctggcgcccc tggtcaaaat ggagaaccag gtgcaaaggg 5160
cgagagagga gccccaggag aaaagggtga gggaggacca cccggtgctg ccggtccagc 5220
tgggggttca ggtcctgctg gaccaccagg tccacagggc gttaaaggtg agagaggaag 5280
tccaggtggt cctggagctg ctggattccc aggtggccgt ggacctcctg gtccccctgg 5340
atcgaatggt aatcctggtc cgccaggtag ttcgggtgct cctgggaagg acggtccacc 5400
tggcccccca ggtagtaacg gtgcacctgg tagtccaggt atatccggac ctaaaggaga 5460
ttccggtcca ccaggcgaaa gaggggcccc aggcccacag ggtccaccag gagccccegg 5520 tcctctgggt attgctggtc ttactggtgc acgtggactg gccggtccac ccggaatgcc 5580
tggagcaaga ggttcacctg gaccacaagg tattaaagga gagaacggta aacctggacc 5640

-continued ttccggtcaa aacggagagc ggggaccccc aggcccccaa ggtctgccag gactagctgg 5700
taccgcaggg gaaccaggaa gagatggaaa tccaggttca gacggactac ccggtagaga 5760
tggtgcaccg ggggccaagg gcgacagggg tgagaatgga tctcctggtg cgccaggggc 5820
accaggccac ccaggtcccc caggtcctgt gggccctgct ggaaagtcag gtgacagggg 5880
agagacaggc ccggctggtc catctggcgc acccggacca gctggttcca gaggcccacc 5940
tggtccgcaa ggccctagag gtgacaaggg agagactgga gaacgaggtg ctatgggtat 6000
caagggtcat agaggttttc cgggtaatcc cggcgcccca ggttctcctg gtccagctgg 6060
ccatcaaggt gcagtcggat cgcccggccc agccggtccc aggggccctg ttggtccatc 6120
cggtcctcca ggaaaggatg gtgcttctgg acacccagga cctatcggac ctccgggtcc 6180
tagaggtaat agaggagaac gtggatccga gggtagtcct ggtcaccctg gtcaacctgg 6240
cccaccaggg cctccaggtg cacccggtcc atgttgtggt gcaggcggtg tggctgcaat 6300
tgctggtgtg ggtgctgaaa aggccggcgg tttcgctcca tattatggtg atgaaccgat 6360
tgattttaag atcaatactg acgaaatcat gacttcctta aagtccgtta atggtcaaat 6420
tgagtctcta atctccccag atggttcacg taaaaatcct gctagaaatt gtagagattt 6480
gaagttttgt caccccgagt tgcagtccgg tgagtactgg gtggacccca atcaaggttg 6540
taagttagac gctattaaag tttactgcaa tatggagaca ggagaaactt gcatcagcgc 6600
ttctccattg actatcccac aaaaaaattg gtggactgac tctggagctg agaaaaagca 6660
tgtatggttc ggggaatcga tggaaggtgg tttccaattc agctacggta accctgaact 6720
tcctgaagat gttcttgacg ttcaattggc atttctgaga ttgttgtcca gtcgtgcaag 6780
ccaaaacatt acataccatt gcaaaaattc catcgcatat atggatcatg ctagcggaaa 6840
tgtgaaaaag gcattgaagc tgatgggatc aaatgaaggt gaatttaaag cagagggtaa 6900
ttctaagttt acttacactg tattggagga tggttgtacg aagcatacag gtgaatgggg 6960
taaaacagtg tttcaatatc aaacccgcaa agcagttaga ttgccaatcg tcgatatcgc 7020
accatacgac attggaggac cagatcaaga gttcggagct gacatcggtc cggtgtgttt 7080
cctttgataa tcaagaggat gtcagaatgc catttgcctg agagatgcag gcttcatttt 7140
tgatactttt ttatttgtaa cctatatagt ataggatttt ttttgtcatt ttgtttcttc 7200
tcgtacgagc ttgctcctga tcagcctatc tcgcagctga tgaatatctt gtggtagggg 7260
tttgggaaaa tcattcgagt ttgatgtttt tcttggtatt tcccactcct cttcagagta 7320
cagaagatta agtgagacgt tcgtttgtgc tccgga 7356

<210> SEQ ID NO 8
<211> LENGTH: 404
<212> TYPE: DNA
<213> ORGANISM: Artificial Sequence
<220> FEATURE:
<223> OTHER INFORMATION: AOX1 landing pad

<400> SEQUENCE: 8
agaagcgata gagagactgc gctaagcatt aatgagatta tttttgagca ttcgtcaatc 60
aataccaaac aagacaaacg gtatgccgac ttttggaagt ttctttttga ccaactggcc 120
gttagcattt caacgaacca aacttagttc atcttggatg agatcacgct tttgtcatat 180
taggttccaa gacagcgttt aaactgtcag ttttgggcca tttggggaac atgaaactat 240
ttgaccccac actcagaaag ccctcatctg gagtgatgtt cgggtgtaat gcggagcttg 300
ttgcattcgg aaataaacaa acatgaacct cgccaggggg gccaggatag acaggctaat 360
aaagtcatgg tgttagtagc ctaatagaag gaattggaat gagc 404

<210> SEQ ID NO 9
<211> LENGTH: 7942
<212> TYPE: DNA
<213> ORGANISM: Artificial Sequence
<220> FEATURE:
<223> OTHER INFORMATION: MMV63

<400> SEQUENCE: 9
ttctttcctg cggtacccag atccaattcc cgctttgact gcctgaaatc tccatcgcct 60
acaatgatga catttggatt tggttgactc atgttggtat tgtgaaatag acgcagatcg 120
ggaacactga aaaatacaca gttattattc atttaaataa catccaaaga cgaaaggttg 180
aatgaaacct ttttgccatc cgacatccac aggtccattc tcacacataa gtgccaaacg 240
caacaggagg ggatacacta gcagcagacc gttgcaaacg caggacctcc actcctcttc 300
tcctcaacac ccacttttgc catcgaaaaa ccagcccagt tattgggctt gattggagct 360
cgctcattcc aattccttct attaggctac taacaccatg actttattag cctgtctatc 420
ctggcccccc tggcgaggtt catgtttgtt tatttccgaa tgcaacaagc tccgcattac 480
acccgaacat cactccagat gagggctttc tgagtgtggg gtcaaatagt ttcatgttcc 540
ccaaatggcc caaaactgac agtttaaacg ctgtcttgga acctaatatg acaaaagcgt 600
gatctcatcc aagatgaact aagtttggtt cgttgaaatg ctaacggcca gttggtcaaa 660
aagaaacttc caaaagtcgg cataccgttt gtcttgtttg gtattgattg acgaatgctc 720
aaaaataatc tcattaatgc ttagcgcagt ctctctatcg cttctgaacc ccggtgcacc 780
tgtgccgaaa cgcaaatggg gaaacacccg ctttttggat gattatgcat tgtctccaca 840
ttgtatgctt ccaagattct ggtgggaata ctgctgatag cctaacgttc atgatcaaaa 900
tttaactgtt ctaaccccta cttgacagca atatataaac agaaggaagc tgccctgtct 960
taaacctttt tttttatcat cattattagc ttactttcat aattgcgact ggttccaatt 1020
gacaagcttt tgattttaac gacttttaac gacaacttga gaagatcaaa aaacaactaa 1080
ttattgaaag aattcaaaac gatgagcttt gtgcaaaagg ggacctggtt acttttcgct 1140
ctgcttcatc ccactgttat tttggcacaa caggaagctg ttgacggagg atgctcccat 1200
ctcggtcagt cttatgcaga tagagatgta tggaaaccag aaccgtgcca aatatgcgtc 1260
tgtgactcag gatccgttct ctgtgatgac ataatatgtg acgaccaaga attagactgc 1320
cccaaccctg aaatcccgtt tggagaatgt tgtgcagttt gcccacagcc tccaacagct 1380
cccactcgcc ctcctaatgg tcaaggacct caaggcccca agggagatcc aggtcctcct 1440
ggtattcctg ggcgaaatgg cgatcctggt cctccaggat caccaggctc cccaggttct 1500
cccggccctc ctggaatctg tgaatcatgt cctactggtg gccagaacta ttctccccag 1560
tacgaagcat atgatgtcaa gtctggagta gcaggaggag gaatcgcagg ctatcctggg 1620
ccagctggtc ctcctggccc acccggaccc cctggcacat ctggccatcc tggtgcccct 1680
ggcgctccag gataccaagg tccccccggt gaacctgggc aagctggtcc ggcaggtcct 1740
ccaggacctc ctggtgctat aggtccatct ggccctgctg gaaaagatgg ggaatcagga 1800
agacccggac gacctggaga gcgaggattt cctggccctc ctggtatgaa aggcccagct 1860
ggtatgcctg gattccctgg tatgaaagga cacagaggct ttgatggacg aaatggagag 1920
aaaggcgaaa ctggtgctcc tggattaaag ggggaaaatg gcgttccagg tgaaaatgga 1980

-continued

```
gctcctggac ccatgggtcc aagaggggct cccggtgaga gaggacggcc aggacttcct   2040
ggagccgcag gggctcgagg taatgatgga gctcgaggaa gtgatggaca accgggcccc   2100
cctggtcctc ctggaactgc aggattccct ggttcccctg gtgctaaggg tgaagttgga   2160
cctgcaggat ctcctggttc aagtggcgcc cctggacaaa gaggagaacc tggacctcag   2220
ggacatgctg gtgctccagg tccccctggg cctcctggga gtaatggtag tcctggtggc   2280
aaaggtgaaa tgggtcctgc tggcattcct ggggctcctg ggctgatagg agctcgtggt   2340
cctccagggc cacctggcac caatggtgtt cccgggcaac gaggtgctgc aggtgaaccc   2400
ggtaagaatg gagccaaagg agacccagga ccacgtgggg aacgcggaga agctggttct   2460
ccaggtatcg caggacctaa gggtgaagat ggcaaagatg gttctcctgg agaacctggt   2520
gcaaatggac ttcctggagc tgcaggagaa aggggtgtgc ctggattccg aggacctgct   2580
ggagcaaatg gccttccagg agaaaagggt cctcctgggg accgtggtgg cccaggccct   2640
gcagggccca gaggtgttgc tggagagccc ggcagagatg gtctccctgg aggtccagga   2700
ttgaggggta ttcctggtag ccccggagga ccaggcagtg atgggaaacc agggcctcct   2760
ggaagccaag gagagacggg tcgacccggt cctccaggtt cacctggtcc gcgaggccag   2820
cctggtgtca tgggcttccc tggtcccaaa ggaaacgatg gtgctcctgg aaaaaatgga   2880
gaacgaggtg gccctggagg tcctggccct cagggtcctg ctggaaagaa tggtgagacc   2940
ggacctcagg gtcctccagg acctactggc ccttctggtg acaaaggaga cacaggaccc   3000
cctggtccac aaggactaca aggcttgcct ggaacgagtg gtcccccagg agaaaacgga   3060
aaacctggtg aacctggtcc aaagggtgag gctggtgcac ctggaattcc aggaggcaag   3120
ggtgattctg gtgctcccgg tgaacgcgga cctcctggag caggagggcc ccctggacct   3180
agaggtggag ctggcccccc tggtcccgaa ggaggaaagg gtgctgctgg tccccctggg   3240
ccacctggtt ctgctggtac acctggtctg caaggaatgc ctggagaaag agggggtcct   3300
ggaggccctg gtccaaaggg tgataagggt gagcctggca gctcaggtgt cgatggtgct   3360
ccagggaaag atggtccacg gggtcccact ggtcccattg gtcctcctgg cccagctggt   3420
cagcctggag ataagggtga aagtggtgcc cctggagttc cgggtatagc tggtcctcgc   3480
ggtggccctg gtgagagagg cgaacagggg cccccaggac ctgctggctt ccctggtgct   3540
cctggccaga atggtgagcc tggtgctaaa ggagaaagag gcgctcctgg tgagaaaggt   3600
gaaggaggcc ctcccggagc cgcaggaccc gccggaggtt ctgggcctgc cggtccccca   3660
ggcccccaag gtgtcaaagg cgaacgtggc agtcctggtg gtcctggtgc tgctggcttc   3720
cccggtggtc gtggtcctcc tggccctcct ggcagtaatg gtaacccagg cccccccaggc   3780
tccagtggtg ctccaggcaa agatggtccc ccaggtccac ctggcagtaa tggtgctcct   3840
ggcagccccg ggatctctgg accaaagggt gattctggtc caccaggtga gaggggagca   3900
cctggccccc agggccctcc gggagctcca ggcccactag gaattgcagg acttactgga   3960
gcacgaggtc ttgcaggccc accaggcatg ccaggtgcta ggggcagccc cggcccacag   4020
ggcatcaagg gtgaaaatgg taaaccagga cctagtggtc agaatggaga acgtggtcct   4080
cctggccccc agggtcttcc tggtctggct ggtacagctg gtgagcctgg aagagatgga   4140
aaccctggat cagatggtct gccaggccga gatggagctc caggtgccaa gggtgaccgt   4200
ggtgaaaatg gctctcctgg tgcccctgga gctcctggtc acccaggccc tcctggtcct   4260
gtcggtccag ctggaaagag cggtgacaga ggagaaactg gccctgctgg tccttctggg   4320
gcccccggtc ctgccggatc aagaggtcct cctggtcccc aaggcccacg cggtgacaaa   4380
```

-continued

```
ggggaaaccg gtgagcgtgg tgctatgggc atcaaaggac atcgcggatt ccctggcaac   4440
ccaggggccc ccggatctcc gggtcccgct ggtcatcaag gtgcagttgg cagtccaggc   4500
cctgcaggcc ccagaggacc tgttggacct agcgggcccc ctggaaagga cggagcaagt   4560
ggacaccctg gtcccattgg accaccgggg ccccgaggta acagaggtga aagaggatct   4620
gagggctccc caggccaccc aggacaacca ggccctcctg gacctcctgg tgcccctggt   4680
ccatgttgtg gtgctggcgg ggttgctgcc attgctggtg ttggagccga aaaagctggt   4740
ggttttgccc catattatgg agatgaaccg atagatttca aatcaacac cgatgagatt   4800
atgacctcac tcaaatcagt caatggacaa atagaaagcc tcattagtcc tgatggttcc   4860
cgtaaaaacc ctgcacggaa ctgcagggac ctgaaattct gccatcctga actccagagt   4920
ggagaatatt gggttgatcc taaccaaggt tgcaaattgg atgctattaa agtctactgt   4980
aacatggaaa ctggggaaac gtgcataagt gccagtcctt tgactatccc acagaagaac   5040
tggtggacag attctggtgc tgagaagaaa catgtttggt ttggagaatc catggagggt   5100
ggttttcagt ttagctatgg caatcctgaa cttcccgaag acgtcctcga tgtccagctg   5160
gcattcctcc gacttctctc cagccgggcc tctcagaaca tcacatatca ctgcaagaat   5220
agcattgcat acatggatca tgccagtggg aatgtaaaga aagccttgaa gctgatgggg   5280
tcaaatgaag gtgaattcaa ggctgaagga aatagcaaat tcacatacac agttctggag   5340
gatggttgca caaaacacac tggggaatgg ggcaaaacag tcttccagta tcaaacacgc   5400
aaggccgtca gactacctat tgtagatatt gcaccctatg atatcggtgg tcctgatcaa   5460
gaatttggtg cggacattgg ccctgtttgc tttttataaa ggggcggccg ctcaagagga   5520
tgtcagaatg ccatttgcct gagagatgca ggcttcattt ttgatacttt tttatttgta   5580
acctatatag tataggattt tttttgtcat tttgtttctt ctcgtacgag cttgctcctg   5640
atcagcctat ctcgcagcag atgaatatct tgtggtaggg gtttgggaaa atcattcgag   5700
tttgatgttt ttcttggtat ttcccactcc tcttcagagt acagaagatt aagtgaaacc   5760
ttcgtttgtg cggatccttc agtaatgtct tgtttctttt gttgcagtgg tgagccattt   5820
tgacttcgtg aaagtttctt tagaatagtt gtttccagag gccaaacatt ccacccgtag   5880
taaagtgcaa gcgtaggaag accaagactg gcataaatca ggtataagtg tcgagcactg   5940
gcaggtgatc ttctgaaagt ttctactagc agataagatc cagtagtcat gcatatggca   6000
acaatgtacc gtgtggatct aagaacgcgt cctactaacc ttcgcattcg ttggtccagt   6060
ttgttgttat cgatcaacgt gacaaggttg tcgattccgc gtaagcatgc atacccaagg   6120
acgcctgttg caattccaag tgagccagtt ccaacaatct ttgtaatatt agagcacttc   6180
attgtgttgc gcttgaaagt aaaatgcgaa caaattaaga gataatctcg aaaccgcgac   6240
ttcaaacgcc aatatgatgt gcggcacaca ataagcgttc atatccgctg ggtgactttc   6300
tcgctttaaa aaattatccg aaaaaatttt ctagagtgtt gttactttat acttccggct   6360
cgtataatac gacaaggtgt aaggaggact aaaccatggc taaactcacc tctgctgttc   6420
cagtcctgac tgctcgtgat gttgctggtg ctgttgagtt ctggactgat agactcggtt   6480
tctcccgtga cttcgtagag gacgactttg ccggtgttgt acgtgacgac gttaccctgt   6540
tcatctccgc agttcaggac caggttgtgc cagacaacac tctggcatgg gtatgggttc   6600
gtggtctgga cgaactgtac gctgagtggt ctgaggtcgt gtctaccaac ttccgtgatg   6660
catctggtcc agctatgacc gagatcggtg aacagccctg ggggtcgtgag tttgcactgc   6720
```

```
gtgatccagc tggtaactgc gtgcatttcg tcgcagaaga gcaggactaa caattgacac   6780
cttacgatta tttagagagt atttattagt tttattgtat gtatacggat gttttattat   6840
ctatttatgc ccttatattc tgtaactatc caaaagtcct atcttatcaa gccagcaatc   6900
tatgtccgcg aacgtcaact aaaaataagc tttttatgct cttctctctt tttttccctt   6960
cggtataatt ataccttgca tccacagatt ctcctgccaa attttgcata atcctttaca   7020
acatggctat atgggagcac ttagcgccct ccaaaaccca tattgcctac gcatgtatag   7080
gtgtttttc cacaatattt tctctgtgct ctctttttat taaagagaag ctctatatcg   7140
gagaagcttc tgtggccgtt atattcggcc ttatcgtggg accacattgc ctgaattggt   7200
ttgccccgga agattgggga aacttggatc tgattacctt agctgcaggt accactgagc   7260
gtcagacccc gtagaaaaga tcaaaggatc ttcttgagat cctttttttc tgcgcgtaat   7320
ctgctgcttg caaacaaaaa aaccaccgct accagcggtg gtttgtttgc cggatcaaga   7380
gctaccaact ctttttccga aggtaactgg cttcagcaga gcgcagatac caaatactgt   7440
tcttctagtg tagccgtagt taggccacca cttcaagaac tctgtagcac cgcctacata   7500
cctcgctctg ctaatcctgt taccagtggc tgctgccagt ggcgataagt cgtgtcttac   7560
cgggttggac tcaagacgat agttaccgga taaggcgcag cggtcgggct gaacgggggg   7620
ttcgtgcaca cagcccagct tggagcgaac gacctacacc gaactgagat acctacagcg   7680
tgagctatga gaaagcgcca cgcttcccga agggagaaag gcggacaggt atccggtaag   7740
cggcagggtc ggaacaggag agcgcacgag ggagcttcca gggggaaacg cctggtatct   7800
ttatagtcct gtcgggtttc gccacctctg acttgagcgt cgatttttgt gatgctcgtc   7860
aggggggcgg agcctatgga aaaacgccag caacgcggcc tttttacggt tcctggcctt   7920
ttgctggcct tttgctcaca tg                                              7942
```

```
<210> SEQ ID NO 10
<211> LENGTH: 7954
<212> TYPE: DNA
<213> ORGANISM: Artificial Sequence
<220> FEATURE:
<223> OTHER INFORMATION: MMV77

<400> SEQUENCE: 10
```

```
ccgtagaaaa gatcaaagga tcttcttgag atcctttttt tctgcgcgta atctgctgct     60
tgcaaacaaa aaaaccaccg ctaccagcgg tggtttgttt gccggatcaa gagctaccaa    120
ctctttttcc gaaggtaact ggcttcagca gagcgcagat accaaatact gttcttctag    180
tgtagccgta gttaggccac cacttcaaga actctgtagc accgcctaca tacctcgctc    240
tgctaatcct gttaccagtg gctgctgcca gtggcgataa gtcgtgtctt accgggttgg    300
actcaagacg atagttaccg gataaggcgc agcggtcggg ctgaacgggg ggttcgtgca    360
cacagcccag cttggagcga acgacctaca ccgaactgag atacctacag cgtgagctat    420
gagaaagcgc cacgcttccc gaagggagaa aggcggacag gtatccggta agcggcaggg    480
tcggaacagg agagcgcacg agggagcttc cagggggaaa cgcctggtat ctttatagtc    540
ctgtcgggtt tcgccacctc tgacttgagc gtcgattttt gtgatgctcg tcaggggggc    600
ggagcctatg gaaaaacgcc agcaacgcgg cctttttacg gttcctggcc ttttgctggc    660
cttttgctca catgttcttt cctgcggtac ccagatccaa ttcccgcttt gactgcctga    720
aatctccatc gcctacaatg atgacatttg gatttggttg actcatgttg gtattgtgaa    780
atagacgcag atcgggaaca ctgaaaaata cacagttatt attcatttaa ataacatcca    840
```

-continued

```
aagacgaaag gttgaatgaa accttttttgc catccgacat ccacaggtcc attctcacac    900

ataagtgcca aacgcaacag gaggggatac actagcagca gaccgttgca aacgcaggac    960

ctccactcct cttctcctca acacccactt ttgccatcga aaaaccagcc cagttattgg   1020

gcttgattgg agctcgctca ttccaattcc ttctattagg ctactaacac catgacttta   1080

ttagcctgtc tatcctggcc cccctggcga ggttcatgtt tgtttatttc cgaatgcaac   1140

aagctccgca ttacacccga acatcactcc agatgagggc tttctgagtg tggggtcaaa   1200

tagtttcatg ttccccaaat ggcccaaaac tgacagttta aacgctgtct tggaacctaa   1260

tatgacaaaa gcgtgatctc atccaagatg aactaagttt ggttcgttga aatgctaacg   1320

gccagttggt caaaaagaaa cttccaaaag tcggcatacc gtttgtcttg tttggtattg   1380

attgacgaat gctcaaaaat aatctcatta atgcttagcg cagtctctct atcgcttctg   1440

aaccccggtg cacctgtgcc gaaacgcaaa tggggaaaca cccgcttttt ggatgattat   1500

gcattgtctc cacattgtat gcttccaaga ttctggtggg aatactgctg atagcctaac   1560

gttcatgatc aaaatttaac tgttctaacc cctacttgac agcaatatat aaacagaagg   1620

aagctgccct gtcttaaacc ttttttttta tcatcattat tagcttactt tcataattgc   1680

gactggttcc aattgacaag cttttgattt taacgacttt taacgacaac ttgagaagat   1740

caaaaaacaa ctaattattg aaagaattca aaacgatgat gtcttttgtc caaaagggta   1800

cttggttact ttttgctctg ttgcacccaa ctgttattct cgcacaacag gaagcagtag   1860

atggtggttg ctcacattta ggtcaatctt acgcagatag agatgtatgg aaacctgaac   1920

catgtcaaat ttgcgtgtgt gactcaggtt cagtgctctg cgacgatatc atatgtgacg   1980

accaggaatt ggactgtcca aacccagaga taccattcgg tgaatgttgt gctgtttgtc   2040

cacagccacc aactgctcct acaagacctc caaacggtca aggtccacaa ggtcctaaag   2100

gtgatccggg tccacctggt attcctggta gaaatggtga ccctggacct cccggttccc   2160

caggtagccc aggatcacct gggcctcctg gaatatgtga atcctgccca actggtggtc   2220

agaactatag cccacaatac gaggcctacg acgtcaaatc tggtgttgct ggaggaggta   2280

ttgcaggcta ccctggtccc gcagggcccc caggtccgcc gggtccgccc ggaacatcag   2340

gtcatcccgg agcccctggt gcaccaggtt atcagggacc gcccggagag cctggacaag   2400

ctggtcccgc tggacccccct ggtccaccag gtgctattgg accaagtggt cctgccggaa   2460

aagacggtga atccggtaga cctggtagac ccggcgaaag gggtttccca ggtcctcccg   2520

gaatgaaggg tccagccggt atgcccggtt ttcctgggat gaagggtcac agaggatttg   2580

atggtagaaa cggagagaaa ggcgaaaccg gtgctcccgg actgaagggt gaaaacggtg   2640

tccctggtga gaacggcgct cctggaccta tgggtccacg tggtgctcca ggagaaagag   2700

gcagaccagg attgcctggt gcagctggtg ctagaggtaa cgatggtgcc cgtggttccg   2760

atggacaacc cgggccaccc ggccctccag gtaccgctgg atttcctgga agccctggtg   2820

ctaaggggga ggttggtccg gctggtagtc ccggaagtag cggtgcccca ggtcaaagag   2880

gcgaaccagg ccctcagggt cacgcaggag cacctggacc gcctggtcct cctggttcga   2940

atggttcgcc tggaggaaaa ggtgaaatgg ggcccgcagg aatccccggt gcgcctggtc   3000

ttattggtgc caggggtcct ccaggcccgc caggtacaaa tggtgtaccc ggacagcgag   3060

gagcagctgg tgaacctggt aaaaacggtg ccaaaggaga tccaggtcct cgtggagagc   3120

gtggtgaagc tggctctccc ggtatcgccg gtccaaaagg tgaggacggt aaggacggtt   3180
```

-continued cccctggtga gccaggtgcg aacggactgc caggtgcagc cggagagcga ggagtcccag 3240
gattcagggg accagccggt gctaacggct tgcctggtga aaaagggccc cctggtgata 3300
ggggaggacc cggtccagca ggccctcgtg gagttgctgg tgagcctgga cgtgacggtt 3360
taccaggagg gccaggtttg aggggtattc ccgggtcccc tggcggtcct ggatcggatg 3420
gaaaaccagg gccaccaggt tcgcagggtg aaacaggacg tccaggccca cccggctcac 3480
ctggtccaag gggtcagcct ggtgtcatgg gtttccccgg tccaaagggt aatgacggag 3540
caccgggtaa aaatggtgaa cgtggtggcc caggtggtcc aggaccccaa ggtccagctg 3600
gaaaaaacgg tgagacaggt cctcaaggac ctccaggacc taccggtcct agcggagata 3660
agggagatac gggaccgcca ggacctcaag gattgcaagg tttgcctggt acatctggcc 3720
ctcccggaga aaatggtaag cctggagagc caggaccaaa aggcgaagct ggagccccag 3780
gtatccccgg aggtaaggga gactcaggtg ctccgggtga gcgtggtcct ccgggtgccg 3840
gtggtccacc tggacctaga ggtggtgccg ggccgccagg tcctgaaggt ggtaaaggtg 3900
ctgctggtcc accgggaccg cctggctctg ctggtactcc tggcttgcag ggaatgccag 3960
gagagagagg tggacctgga ggtcccggtc cgaagggtga taaaggggag ccaggatcat 4020
ccggtgttga cggcgcacct ggtaaagacg gaccaagggg accaacgggt ccaatcggac 4080
caccaggacc cgctggccag ccaggagata aaggcgagtc cggagcaccc ggtgttcctg 4140
gtatagctgg acccaggggt ggtcccggtg aaagaggtga acagggccca ccgggtcccg 4200
ccggtttccc tggcgcccct ggtcaaaatg gagaaccagg tgcaaagggc gagagaggag 4260
ccccaggaga aaagggtgag ggaggaccac ccggtgctgc cggtccagct ggggggttcag 4320 gtcctgctgg accaccaggt ccacagggcg ttaaaggtga gagaggaagt ccaggtggtc 4380
ctggagctgc tggattccca ggtggccgtg gacctcctgg tccccctgga tcgaatggta 4440
atcctggtcc gccaggtagt tcgggtgctc ctgggaagga cggtccacct ggcccccag 4500 gtagtaacgg tgcacctggt agtccaggta tatccggacc taaaggagat tccggtccac 4560
caggcgaaag aggggcccca ggcccacagg gtccaccagg agcccccggt cctctgggta 4620
ttgctggtct tactggtgca cgtggactgg ccggtccacc cggaatgcct ggagcaagag 4680
gttcacctgg accacaaggt attaaaggag agaacggtaa acctggacct tccggtcaaa 4740
acggagagcg gggaccccca ggcccccaag gtctgccagg actagctggt accgcagggg 4800
aaccaggaag agatggaaat ccaggttcag acggactacc cggtagagat ggtgcaccgg 4860
gggccaaggg cgacaggggt gagaatggat ctcctggtgc gccaggggca ccaggccacc 4920
caggtccccc aggtcctgtg ggccctgctg gaaagtcagg tgacagggga gagacaggcc 4980
cggctggtcc atctggcgca cccggaccag ctggttccag aggcccacct ggtccgcaag 5040
gccctagagg tgacaaggga gagactggag aacgaggtgc tatgggtatc aagggtcata 5100
gaggttttcc gggtaatccc ggcgccccag gttctcctgg tccagctggc catcaaggtg 5160
cagtcggatc gcccggccca gccggtccca ggggccctgt tggtccatcc ggtcctccag 5220
gaaaggatgg tgcttctgga cacccaggac ctatcggacc tccgggtcct agaggtaata 5280
gaggagaacg tggatccgag ggtagtcctg gtcaccctgg tcaacctggc ccaccagggc 5340
ctccaggtgc acccggtcca tgttgtggtg caggcggtgt ggctgcaatt gctggtgtgg 5400
gtgctgaaaa ggccggcggt ttcgctccat attatggtga tgaaccgatt gattttaaga 5460
tcaatactga cgaaatcatg acttccttaa agtccgttaa tggtcaaatt gagtctctaa 5520
tctccccaga tggttcacgt aaaaatcctg ctagaaattg tagagatttg aagttttgtc 5580

-continued

```
accccgagtt gcagtccggt gagtactggg tggaccccaa tcaaggttgt aagttagacg   5640
ctattaaagt ttactgcaat atggagacag gagaaacttg catcagcgct tctccattga   5700
ctatcccaca aaaaaattgg tggactgact ctggagctga gaaaaagcat gtatggttcg   5760
gggaatcgat ggaaggtggt ttccaattca gctacggtaa ccctgaactt cctgaagatg   5820
ttcttgacgt tcaattggca tttctgagat tgttgtccag tcgtgcaagc caaaacatta   5880
cataccattg caaaaattcc atcgcatata tggatcatgc tagcggaaat gtgaaaaagg   5940
cattgaagct gatgggatca aatgaaggtg aatttaaagc agagggtaat tctaagttta   6000
cttacactgt attggaggat ggttgtacga agcatacagg tgaatggggt aaaacagtgt   6060
ttcaatatca aacccgcaaa gcagttagat tgccaatcgt cgatatcgca ccatacgaca   6120
ttggaggacc agatcaagag ttcggagctg acatcggtcc ggtgtgtttc ctttgataag   6180
gttaaagggg cggccgctca agaggatgtc agaatgccat ttgcctgaga gatgcaggct   6240
tcatttttga tactttttta tttgtaacct atatagtata ggattttttt tgtcattttg   6300
tttcttctcg tacgagcttg ctcctgatca gcctatctcg cagcagatga atatcttgtg   6360
gtaggggttt gggaaaatca ttcgagtttg atgtttttct tggtatttcc cactcctctt   6420
cagagtacag aagattaagt gaaaccttcg tttgtgcgga tccttcagta atgtcttgtt   6480
tcttttgttg cagtggtgag ccattttgac ttcgtgaaag tttctttaga atagttgttt   6540
ccagaggcca aacattccac ccgtagtaaa gtgcaagcgt aggaagacca agactggcat   6600
aaatcaggta taagtgtcga gcactggcag gtgatcttct gaaagtttct actagcagat   6660
aagatccagt agtcatgcat atggcaacaa tgtaccgtgt ggatctaaga acgcgtccta   6720
ctaaccttcg cattcgttgg tccagtttgt tgttatcgat caacgtgaca aggttgtcga   6780
ttccgcgtaa gcatgcatac ccaaggacgc ctgttgcaat tccaagtgag ccagttccaa   6840
caatctttgt aatattagag cacttcattg tgttgcgctt gaaagtaaaa tgcgaacaaa   6900
ttaagagata atctcgaaac cgcgacttca aacgccaata tgatgtgcgg cacacaataa   6960
gcgttcatat ccgctgggtg actttctcgc tttaaaaaat tatccgaaaa aatttttctag  7020
agtgttgtta ctttatactt ccggctcgta taatacgaca aggtgtaagg aggactaaac   7080
catggctaaa ctcacctctg ctgttccagt cctgactgct cgtgatgttg ctggtgctgt   7140
tgagttctgg actgatagac tcggtttctc ccgtgacttc gtagaggacg actttgccgg   7200
tgttgtacgt gacgacgtta ccctgttcat ctccgcagtt caggaccagg ttgtgccaga   7260
caacactctg gcatgggtat gggttcgtgg tctggacgaa ctgtacgctg agtggtctga   7320
ggtcgtgtct accaacttcc gtgatgcatc tggtccagct atgaccgaga tcggtgaaca   7380
gccctggggt cgtgagtttg cactgcgtga tccagctggt aactgcgtgc atttcgtcgc   7440
agaagaacag gactaacaat tgacacctta cgattattta gagagtattt attagtttta   7500
ttgtatgtat acggatgttt tattatctat ttatgccctt atattctgta actatccaaa   7560
agtcctatct tatcaagcca gcaatctatg tccgcgaacg tcaactaaaa ataagctttt   7620
tatgctgttc tctctttttt tcccttcggt ataattatac cttgcatcca cagattctcc   7680
tgccaaattt tgcataatcc tttacaacat ggctatatgg gagcacttag cgccctccaa   7740
aacccatatt gcctacgcat gtataggtgt tttttccaca atattttctc tgtgctctct   7800
ttttattaaa gagaagctct atatcggaga agcttctgtg gccgttatat tcggccttat   7860
cgtgggacca cattgcctga attggtttgc cccggaagat tggggaaact tggatctgat   7920
```

-continued taccttagct gcaggtacca ctgagcgtca gacc 7954

<210> SEQ ID NO 11
<211> LENGTH: 7356
<212> TYPE: DNA
<213> ORGANISM: Artificial Sequence
<220> FEATURE:
<223> OTHER INFORMATION: MMV129

<400> SEQUENCE: 11
ggatccttca gtaatgtctt gtttcttttg ttgcagtggt gagccatttt gacttcgtga 60
aagtttcttt agaatagttg tttccagagg ccaaacattc cacccgtagt aaagtgcaag 120
cgtaggaaga ccaagactgg cataaatcag gtataagtgt cgagcactgg caggtgatct 180
tctgaaagtt tctactagca gataagatcc agtagtcatg catatggcaa caatgtaccg 240
tgtggatcta agaacgcgtc ctactaacct tcgcattcgt tggtccagtt tgttgttatc 300
gatcaacgtg acaaggttgt cgattccgcg taagcatgca tacccaagga cgcctgttgc 360
aattccaagt gagccagttc caacaatctt tgtaatatta gagcacttca ttgtgttgcg 420
cttgaaagta aaatgcgaac aaattaagag ataatctcga aaccgcgact tcaaacgcca 480
atatgatgtg cggcacacaa taagcgttca tatccgctgg gtgactttct cgctttaaaa 540
aattatccga aaaaatttc tagagtgttg ttactttata cttccggctc gtataatacg 600
acaaggtgta aggaggacta aaccatggct aaactcacct ctgctgttcc agtcctgact 660
gctcgtgatg ttgctggtgc tgttgagttc tggactgata ggctcggttt ctcccgtgac 720
ttcgtagagg acgactttgc cggtgttgta cgtgacgacg ttaccctgtt catctccgca 780
gttcaggacc aggttgtgcc agacaacact ctggcatggg tatgggttcg tggtctggac 840
gaactgtacg ctgagtggtc tgaggtcgtg tctaccaact tccgtgatgc atctggtcca 900
gctatgaccg agatcggtga acagccctgg ggtcgtgagt ttgcactgcg tgatccagct 960
ggtaactgcg tgcatttcgt cgcagaagag caggactaac aattgacacc ttacgattat 1020
ttagagagta tttattagtt ttattgtatg tatacggatg ttttattatc tatttatgcc 1080
cttatattct gtaactatcc aaaagtccta tcttatcaag ccagcaatct atgtccgcga 1140
acgtcaacta aaaataagct ttttatgctc ttctctcttt ttttcccttc ggtataatta 1200
taccttgcat ccacagattc tcctgccaaa ttttgcataa tcctttacaa catggctata 1260
tgggagcact tagcgccctc caaaacccat attgcctacg catgtatagg tgtttttttcc 1320 acaatatttt ctctgtgctc tctttttatt aaagagaagc tctatatcgg agaagcttct 1380
gtggccgtta tattcggcct tatcgtggga ccacattgcc tgaattggtt tgccccggaa 1440
gattggggaa acttggatct gattacctta gctgcagaaa agggtaccac tgagcgtcag 1500
accccgtaga aaagatcaaa ggatcttctt gagatccttt ttttctgcgc gtaatctgct 1560
gcttgcaaac aaaaaaacca ccgctaccag cggtggtttg tttgccggat caagagctac 1620
caactctttt tccgaaggta actggcttca gcagagcgca gataccaaat actgttcttc 1680
tagtgtagcc gtagttaggc caccacttca agaactctgt agcaccgcct acatacctcg 1740
ctctgctaat cctgttacca gtggctgctg ccagtggcga taagtcgtgt cttaccgggt 1800
tggacccaag acgatagtta ccggataagg cgcagcggtc gggctgaacg gggggttcgt 1860
gcacacagcc cagcttggag cgaacgacct acaccgaact gagataccta cagcgtgagc 1920
tatgagaaag cgccacgctt cccgaaggga gaaaggcgga caggtatccg gtaagcggca 1980
gggtcggaac aggagagcgc acgagggagc ttccaggggg aaacgcctgg tatctttata 2040

```
gtcctgtcgg gtttcgccac ctctgacttg agcgtcgatt tttgtgatgc tcgtcagggg   2100
ggcggagcct atggaaaaac gccagcaacg cggccttttt acggttcctg gccttttgct   2160
ggccttttgc tcacatgtat ttaaattaat cgaactccga atgcggttct cctgtaacct   2220
taattgtagc atagatcact taaataaact catggcctga catctgtaca cgttcttatt   2280
ggtcttttag caatcttgaa gtctttctat tgttccggtc ggcattacct aataaattcg   2340
aatcgagatt gctagtacct gatatcatat gaagtaatca tcacatgcaa gttccatgat   2400
accctctact aatggaattg aacaaagttt aagcttctcg cacgagaccg aatccatact   2460
atgcacccct caaagttggg attagtcagg aaagctgagc aattaacttc cctcgattgg   2520
cctggacttt tcgcttagcc tgccgcaatc ggtaagtttc attatcccag cggggtgata   2580
gcctctgttg ctcatcaggc caaaatcata tataagctgt agacccagca cttcaattac   2640
ttgaaattca ccataacact tgctctagtc aagacttaca attaaaatga tgtcttttgt   2700
ccaaaagggt acttggttac tttttgctct gttgcaccca actgttattc tcgcacaaca   2760
ggaagcagta gatggtggtt gctcacattt aggtcaatct tacgcagata gagatgtatg   2820
gaaacctgaa ccatgtcaaa tttgcgtgtg tgactcaggt tcagtgctct gcgacgatat   2880
catatgtgac gaccaggaat tggactgtcc aaacccagag ataccattcg gtgaatgttg   2940
tgctgtttgt ccacagccac caactgctcc tacaagacct ccaaacggtc aaggtccaca   3000
aggtcctaaa ggtgatccgg gtccacctgg tattcctggt agaaatggtg accctggacc   3060
tcccggttcc ccaggtagcc caggatcacc tgggcctcct ggaatatgtg aatcctgccc   3120
aactggtggt cagaactata gcccacaata cgaggcctac gacgtcaaat ctggtgttgc   3180
tggaggaggt attgcaggct accctggtcc cgcagggccc ccaggtccgc cgggtccgcc   3240
cggaacatca ggtcatcccg gagcccctgg tgcaccaggt tatcagggac cgcccggaga   3300
gcctggacaa gctggtcccg ctggaccccc tggtccacca ggtgctattg gaccaagtgg   3360
tcctgccgga aaagacggtg aatccggtag acctggtaga cccggcgaaa ggggtttccc   3420
aggtcctccc ggaatgaagg gtccagccgg tatgcccggt tttcctggga tgaagggtca   3480
cagaggattt gatggtagaa acggagagaa aggcgaaacc ggtgctcccg gactgaaggg   3540
tgaaaacggt gtccctggtg agaacggcgc tcctggacct atgggtccac gtggtgctcc   3600
aggagaaaga ggcagaccag gattgcctgg tgcagctggt gctagaggta acgatggtgc   3660
ccgtggttcc gatggacaac ccgggccacc cggccctcca ggtaccgctg gatttcctgg   3720
aagccctggt gctaaggggg aggttggtcc ggctggtagt cccggaagta gcggtgcccc   3780
aggtcaaaga ggcgaaccag gccctcaggg tcacgcagga gcacctggac cgcctggtcc   3840
tcctggttcg aatggttcgc ctggaggaaa aggtgaaatg ggcccgcag gaatccccgg   3900
tgcgcctggt cttattggtg ccaggggtcc tccaggcccg ccaggtacaa atggtgtacc   3960
cggacagcga ggagcagctg gtgaacctgg taaaaacggt gccaaaggag atccaggtcc   4020
tcgtggagag cgtggtgaag ctggctctcc cggtatcgcc ggtccaaaag gtgaggacgg   4080
taaggacggt tcccctggtg agccaggtgc gaacggactg ccaggtgcag ccggagagcg   4140
aggagtccca ggattcaggg gaccagccgg tgctaacggc ttgcctggtg aaaaagggcc   4200
ccctggtgat aggggaggac ccggtccagc aggccctcgt ggagttgctg gtgagcctgg   4260
acgtgacggt ttaccaggag ggccaggttt gaggggtatt cccgggtccc ctggcggtcc   4320
tggatcggat ggaaaaccag ggccaccagg ttcgcagggt gaaacaggac gtccaggccc   4380
```

-continued

```
acccggctca cctggtccaa ggggtcagcc tggtgtcatg ggtttccccg gtccaaaggg   4440
taatgacgga gcaccgggta aaaatggtga acgtggtggc ccaggtggtc caggacccca   4500
aggtccagct ggaaaaaacg gtgagacagg tcctcaagga cctccaggac ctaccggtcc   4560
tagcggagat aagggagata cgggaccgcc aggacctcaa ggattgcaag gtttgcctgg   4620
tacatctggc cctcccggag aaaatggtaa gcctggagag ccaggaccaa aaggcgaagc   4680
tggagcccca ggtatccccg gaggtaaggg agactcaggt gctccgggtg agcgtggtcc   4740
tccgggtgcc ggtggtccac ctggacctag aggtggtgcc gggccgccag gtcctgaagg   4800
tggtaaaggt gctgctggtc caccgggacc gcctggctct gctggtactc ctggcttgca   4860
gggaatgcca ggagagagag gtggacctgg aggtcccggt ccgaagggtg ataaagggga   4920
gccaggatca tccggtgttg acggcgcacc tggtaaagac ggaccaaggg gaccaacggg   4980
tccaatcgga ccaccaggac ccgctggcca gccaggagat aaaggcgagt ccggagcacc   5040
cggtgttcct ggtatagctg gacccagggg tggtcccggt gaaagaggtg aacagggccc   5100
accgggtccc gccggtttcc ctggcgcccc tggtcaaaat ggagaaccag gtgcaaaggg   5160
cgagagagga gccccaggag aaaagggtga gggaggacca cccggtgctg ccggtccagc   5220
tgggggttca ggtcctgctg gaccaccagg tccacagggc gttaaaggtg agagaggaag   5280
tccaggtggt cctggagctg ctggattccc aggtggccgt ggacctcctg gtccccctgg   5340
atcgaatggt aatcctggtc cgccaggtag ttcgggtgct cctgggaagg acggtccacc   5400
tggcccccca ggtagtaacg gtgcacctgg tagtccaggt atatccggac ctaaaggaga   5460
ttccggtcca ccaggcgaaa gaggggcccc aggcccacag ggtccaccag gagcccccgg   5520
tcctctgggt attgctggtc ttactggtgc acgtggactg gccggtccac ccggaatgcc   5580
tggagcaaga ggttcacctg gaccacaagg tattaaagga gagaacggta aacctggacc   5640
ttccggtcaa aacggagagc ggggaccccc aggcccccaa ggtctgccag gactagctgg   5700
taccgcaggg gaaccaggaa gagatggaaa tccaggttca gacggactac ccggtagaga   5760
tggtgcaccg ggggccaagg gcgacagggg tgagaatgga tctcctggtg cgccaggggc   5820
accaggccac ccaggtcccc caggtcctgt gggccctgct ggaaagtcag gtgacagggg   5880
agagacaggc ccggctggtc catctggcgc acccggacca gctggttcca gaggcccacc   5940
tggtccgcaa ggccctagag gtgacaaggg agagactgga gaacgaggtg ctatgggtat   6000
caagggtcat agaggttttc cgggtaatcc cggcgcccca ggttctcctg gtccagctgg   6060
ccatcaaggt gcagtcggat cgcccggccc agccggtccc aggggccctg ttggtccatc   6120
cggtcctcca ggaaaggatg gtgcttctgg acacccagga cctatcggac ctccgggtcc   6180
tagaggtaat agaggagaac gtggatccga gggtagtcct ggtcaccctg gtcaacctgg   6240
cccaccaggg cctccaggtg cacccggtcc atgttgtggt gcaggcggtg tggctgcaat   6300
tgctggtgtg ggtgctgaaa aggccggcgg tttcgctcca tattatggtg atgaaccgat   6360
tgattttaag atcaatactg acgaaatcat gacttcctta aagtccgtta atggtcaaat   6420
tgagtctcta atctccccag atggttcacg taaaaatcct gctagaaatt gtagagattt   6480
gaagttttgt caccccgagt tgcagtccgg tgagtactgg gtggacccca atcaaggttg   6540
taagttagac gctattaaag tttactgcaa tatggagaca ggagaaactt gcatcagcgc   6600
ttctccattg actatcccac aaaaaaattg gtggactgac tctggagctg agaaaaagca   6660
tgtatggttc ggggaatcga tggaaggtgg tttccaattc agctacggta accctgaact   6720
tcctgaagat gttcttgacg ttcaattggc atttctgaga ttgttgtcca gtcgtgcaag   6780
```

```
ccaaaacatt acataccatt gcaaaaattc catcgcatat atggatcatg ctagcggaaa   6840

tgtgaaaaag gcattgaagc tgatgggatc aaatgaaggt gaatttaaag cagagggtaa   6900

ttctaagttt acttacactg tattggagga tggttgtacg aagcatacag gtgaatgggg   6960

taaaacagtg tttcaatatc aaacccgcaa agcagttaga ttgccaatcg tcgatatcgc   7020

accatacgac attggaggac cagatcaaga gttcggagct gacatcggtc cggtgtgttt   7080

cctttgataa tcaagaggat gtcagaatgc catttgcctg agagatgcag gcttcatttt   7140

tgatactttt ttatttgtaa cctatatagt ataggatttt ttttgtcatt ttgtttcttc   7200

tcgtacgagc ttgctcctga tcagcctatc tcgcagctga tgaatatctt gtggtagggg   7260

tttgggaaaa tcattcgagt ttgatgtttt tcttggtatt tcccactcct cttcagagta   7320

cagaagatta agtgagacgt tcgtttgtgc tccgga                             7356
```

<210> SEQ ID NO 12
<211> LENGTH: 7879
<212> TYPE: DNA
<213> ORGANISM: Artificial Sequence
<220> FEATURE:
<223> OTHER INFORMATION: MMV130

<400> SEQUENCE: 12

```
ggatccttca gtaatgtctt gtttcttttg ttgcagtggt gagccatttt gacttcgtga     60

aagtttcttt agaatagttg tttccagagg ccaaacattc cacccgtagt aaagtgcaag    120

cgtaggaaga ccaagactgg cataaatcag gtataagtgt cgagcactgg caggtgatct    180

tctgaaagtt tctactagca gataagatcc agtagtcatg catatggcaa caatgtaccg    240

tgtggatcta agaacgcgtc ctactaacct tcgcattcgt tggtccagtt tgttgttatc    300

gatcaacgtg acaaggttgt cgattccgcg taagcatgca tacccaagga cgcctgttgc    360

aattccaagt gagccagttc caacaatctt tgtaatatta gagcacttca ttgtgttgcg    420

cttgaaagta aaatgcgaac aaattaagag ataatctcga aaccgcgact tcaaacgcca    480

atatgatgtg cggcacacaa taagcgttca tatccgctgg gtgactttct cgctttaaaa    540

aattatccga aaaaatttc tagagtgttg ttactttata cttccggctc gtataatacg    600

acaaggtgta aggaggacta aaccatggct aaactcacct ctgctgttcc agtcctgact    660

gctcgtgatg ttgctggtgc tgttgagttc tggactgata ggctcggttt ctcccgtgac    720

ttcgtagagg acgactttgc cggtgttgta cgtgacgacg ttaccctgtt catctccgca    780

gttcaggacc aggttgtgcc agacaacact ctggcatggg tatgggttcg tggtctggac    840

gaactgtacg ctgagtggtc tgaggtcgtg tctaccaact tccgtgatgc atctggtcca    900

gctatgaccg agatcggtga acagccctgg ggtcgtgagt ttgcactgcg tgatccagct    960

ggtaactgcg tgcatttcgt cgcagaagag caggactaac aattgacacc ttacgattat   1020

ttagagagta tttattagtt ttattgtatg tatacggatg ttttattatc tatttatgcc   1080

cttatattct gtaactatcc aaaagtccta tcttatcaag ccagcaatct atgtccgcga   1140

acgtcaacta aaaataagct ttttatgctc ttctctcttt ttttcccttc ggtataatta   1200

taccttgcat ccacagattc tcctgccaaa ttttgcataa tcctttacaa catggctata   1260

tgggagcact tagcgccctc caaaacccat attgcctacg catgtatagg tgttttttcc   1320

acaatatttt ctctgtgctc tctttttatt aaagagaagc tctatatcgg agaagcttct   1380

gtggccgtta tattcggcct tatcgtggga ccacattgcc tgaattggtt tgccccggaa   1440
```

```
gattggggaa acttggatct gattacctta gctgcagaaa agggtaccac tgagcgtcag   1500
accccgtaga aaagatcaaa ggatcttctt gagatccttt ttttctgcgc gtaatctgct   1560
gcttgcaaac aaaaaaacca ccgctaccag cggtggtttg tttgccggat caagagctac   1620
caactctttt tccgaaggta actggcttca gcagagcgca gataccaaat actgttcttc   1680
tagtgtagcc gtagttaggc caccacttca agaactctgt agcaccgcct acatacctcg   1740
ctctgctaat cctgttacca gtggctgctg ccagtggcga taagtcgtgt cttaccgggt   1800
tggacccaag acgatagtta ccggataagg cgcagcggtc gggctgaacg gggggttcgt   1860
gcacacagcc cagcttggag cgaacgacct acaccgaact gagataccta cagcgtgagc   1920
tatgagaaag cgccacgctt cccgaaggga gaaaggcgga caggtatccg gtaagcggca   1980
gggtcggaac aggagagcgc acgagggagc ttccaggggg aaacgcctgg tatctttata   2040
gtcctgtcgg gtttcgccac ctctgacttg agcgtcgatt tttgtgatgc tcgtcagggg   2100
ggcggagcct atggaaaaac gccagcaacg cggccttttt acggttcctg gccttttgct   2160
ggccttttgc tcacatgtat ttcagaagcg atagagagac tgcgctaagc attaatgaga   2220
ttatttttga gcattcgtca atcaatacca aacaagacaa acggtatgcc gacttttgga   2280
agtttctttt tgaccaactg gccgttagca tttcaacgaa ccaaacttag ttcatcttgg   2340
atgagatcac gcttttgtca tattaggttc caagacagcg tttaaactgt cagttttggg   2400
ccatttgggg aacatgaaac tatttgaccc cacactcaga aagccctcat ctgagtgatg   2460
ttcgggtgta atgcggagct tgttgcattc ggaaataaac aaacatgaac ctcgccaggg   2520
gggccaggat agacaggcta ataaagtcat ggtgttagta gcctaataga aggaattgga   2580
ataaataatg tatctaaacg caaactccga gctggaaaaa tgttaccggc gatgcgcgga   2640
caatttagag gcggcgatca agaaacacct gctgggcgag cagtctggag cacagtcttc   2700
gatgggcccg agatcccacc gcgttcctgg gtaccgggac gtgaggcagc gcgacatcca   2760
tcaaatatac caggcgccaa ccgagtctct cggaaaacag cttctggata tcttccgctg   2820
gcggcgcaac gacgaataat agtccctgga ggtgacggaa tatatatgtg tggagggtaa   2880
atctgacagg gtgtagcaaa ggtaatattt tcctaaaaca tgcaatcggc tgccccgcaa   2940
cgggaaaaag aatgactttg gcactcttca ccagagtggg gtgtcccgct cgtgtgtgca   3000
aataggctcc cactggtcac cccggatttt gcagaaaaac agcaagttcc ggggtgtctc   3060
actggtgtcc gccaataaga ggagccggca ggcacggagt ctacatcaag ctgtctccga   3120
tacactcgac taccatccgg gtctctcaga gaggggaatg gcactataaa taccgcctcc   3180
ttgcgctctc tgccttcatc aatcaaatca tgatgtcttt tgtccaaaag ggtacttggt   3240
tactttttgc tctgttgcac ccaactgtta ttctcgcaca acaggaagca gtagatggtg   3300
gttgctcaca tttaggtcaa tcttacgcag atagagatgt atggaaacct gaaccatgtc   3360
aaatttgcgt gtgtgactca ggttcagtgc tctgcgacga tatcatatgt gacgaccagg   3420
aattggactg tccaaaccca gagataccat tcggtgaatg ttgtgctgtt tgtccacagc   3480
caccaactgc tcctacaaga cctccaaacg gtcaaggtcc acaaggtcct aaaggtgatc   3540
cgggtccacc tggtattcct ggtagaaatg gtgaccctgg acctcccggt tccccaggta   3600
gcccaggatc acctgggcct cctggaatat gtgaatcctg cccaactggt ggtcagaact   3660
atagcccaca atacgaggcc tacgacgtca aatctggtgt tgctggagga ggtattgcag   3720
gctaccctgg tcccgcaggg cccccaggtc cgccgggtcc gcccggaaca tcaggtcatc   3780
ccggagcccc tggtgcacca ggttatcagg gaccgcccgg agagcctgga caagctggtc   3840
```

```
ccgctggacc ccctggtcca ccaggtgcta ttggaccaag tggtcctgcc ggaaaagacg   3900
gtgaatccgg tagacctggt agacccggcg aaaggggttt cccaggtcct cccggaatga   3960
agggtccagc cggtatgccc ggttttcctg ggatgaaggg tcacagagga tttgatggta   4020
gaaacggaga gaaaggcgaa accggtgctc ccggactgaa gggtgaaaac ggtgtccctg   4080
gtgagaacgg cgctcctgga cctatgggtc cacgtggtgc tccaggagaa agaggcagac   4140
caggattgcc tggtgcagct ggtgctagag gtaacgatgg tgcccgtggt tccgatggac   4200
aacccgggcc acccggccct ccaggtaccg ctggatttcc tggaagccct ggtgctaagg   4260
gggaggttgg tccggctggt agtcccggaa gtagcggtgc cccaggtcaa agaggcgaac   4320
caggccctca gggtcacgca ggagcacctg gaccgcctgg tcctcctggt tcgaatggtt   4380
cgcctggagg aaaaggtgaa atggggcccg caggaatccc cggtgcgcct ggtcttattg   4440
gtgccagggg tcctccaggc ccgccaggta caaatggtgt acccggacag cgaggagcag   4500
ctggtgaacc tggtaaaaac ggtgccaaag gagatccagg tcctcgtgga gagcgtggtg   4560
aagctggctc tcccggtatc gccggtccaa aaggtgagga cggtaaggac ggttcccctg   4620
gtgagccagg tgcgaacgga ctgccaggtg cagccggaga gcgaggagtc ccaggattca   4680
ggggaccagc cggtgctaac ggcttgcctg gtgaaaaagg gccccctggt gataggggag   4740
gacccggtcc agcaggccct cgtggagttg ctggtgagcc tggacgtgac ggtttaccag   4800
gagggccagg tttgaggggt attcccgggt cccctggcgg tcctggatcg gatggaaaac   4860
cagggccacc aggttcgcag ggtgaaacag gacgtccagg cccacccggc tcacctggtc   4920
caaggggtca gcctggtgtc atgggtttcc ccggtccaaa gggtaatgac ggagcaccgg   4980
gtaaaaatgg tgaacgtggt ggcccaggtg gtccaggacc ccaaggtcca gctggaaaaa   5040
acggtgagac aggtcctcaa ggacctccag gacctaccgg tcctagcgga gataagggag   5100
atacgggacc gccaggacct caaggattgc aaggtttgcc tggtacatct ggccctcccg   5160
gagaaaatgg taagcctgga gagccaggac caaaaggcga agctggagcc ccaggtatcc   5220
ccggaggtaa gggagactca ggtgctccgg gtgagcgtgg tcctccgggt gccggtggtc   5280
cacctggacc tagaggtggt gccgggccgc caggtcctga aggtggtaaa ggtgctgctg   5340
gtccaccggg accgcctggc tctgctggta ctcctggctt gcagggaatg ccaggagaga   5400
gaggtggacc tggaggtccc ggtccgaagg gtgataaagg ggagccagga tcatccggtg   5460
ttgacggcgc acctggtaaa gacggaccaa ggggaccaac gggtccaatc ggaccaccag   5520
gacccgctgg ccagccagga gataaaggcg agtccggagc acccggtgtt cctggtatag   5580
ctggacccag ggtggtccc ggtgaaagag gtgaacaggg cccaccgggt cccgccggtt   5640
tccctggcgc ccctggtcaa aatggagaac caggtgcaaa gggcgagaga ggagccccag   5700
gagaaaaggg tgagggagga ccacccggtg ctgccggtcc agctgggggt tcaggtcctg   5760
ctggaccacc aggtccacag ggcgttaaag gtgagagagg aagtccaggt ggtcctggag   5820
ctgctggatt cccaggtggc cgtggacctc ctggtccccc tggatcgaat ggtaatcctg   5880
gtccgccagg tagttcgggt gctcctggga aggacggtcc acctggcccc ccaggtagta   5940
acggtgcacc tggtagtcca ggtatatccg gacctaaagg agattccggt ccaccaggcg   6000
aaagaggggc cccaggccca cagggtccac caggagcccc cggtcctctg ggtattgctg   6060
gtcttactgg tgcacgtgga ctggccggtc cacccggaat gcctggagca agaggttcac   6120
ctggaccaca aggtattaaa ggagagaacg gtaaacctgg accttccggt caaaacggag   6180
```

```
agcggggacc cccaggcccc caaggtctgc caggactagc tggtaccgca ggggaaccag   6240
gaagagatgg aaatccaggt tcagacggac tacccggtag agatggtgca ccgggggcca   6300
agggcgacag gggtgagaat ggatctcctg gtgcgccagg ggcaccaggc cacccaggtc   6360
ccccaggtcc tgtgggccct gctggaaagt caggtgacag gggagagaca ggcccggctg   6420
gtccatctgg cgcacccgga ccagctggtt ccagaggccc acctggtccg caaggcccta   6480
gaggtgacaa gggagagact ggagaacgag gtgctatggg tatcaagggt catagaggtt   6540
ttccgggtaa tcccggcgcc ccaggttctc ctggtccagc tggccatcaa ggtgcagtcg   6600
gatcgcccgg cccagccggt cccaggggcc ctgttggtcc atccggtcct ccaggaaagg   6660
atggtgcttc tggacaccca ggacctatcg gacctccggg tcctagaggt aatagaggag   6720
aacgtggatc cgagggtagt cctggtcacc ctggtcaacc tggcccacca gggcctccag   6780
gtgcacccgg tccatgttgt ggtgcaggcg gtgtggctgc aattgctggt gtgggtgctg   6840
aaaaggccgg cggtttcgct ccatattatg gtgatgaacc gattgatttt aagatcaata   6900
ctgacgaaat catgacttcc ttaaagtccg ttaatggtca aattgagtct ctaatctccc   6960
cagatggttc acgtaaaaat cctgctagaa attgtagaga tttgaagttt tgtcaccccg   7020
agttgcagtc cggtgagtac tgggtggacc ccaatcaagg ttgtaagtta gacgctatta   7080
aagtttactg caatatggag acaggagaaa cttgcatcag cgcttctcca ttgactatcc   7140
cacaaaaaaa ttggtggact gactctggag ctgagaaaaa gcatgtatgg ttcggggaat   7200
cgatggaagg tggtttccaa ttcagctacg gtaaccctga acttcctgaa gatgttcttg   7260
acgttcaatt ggcatttctg agattgttgt ccagtcgtgc aagccaaaac attacatacc   7320
attgcaaaaa ttccatcgca tatatggatc atgctagcgg aaatgtgaaa aaggcattga   7380
agctgatggg atcaaatgaa ggtgaattta aagcagaggg taattctaag tttacttaca   7440
ctgtattgga ggatggttgt acgaagcata caggtgaatg ggtaaaaaca gtgtttcaat   7500
atcaaacccg caaagcagtt agattgccaa tcgtcgatat cgcaccatac gacattggag   7560
gaccagatca agagttcgga gctgacatcg gtccggtgtg tttcctttga taatcaagag   7620
gatgtcagaa tgccatttgc ctgagagatg caggcttcat tttgatact tttttatttg   7680
taacctatat agtataggat tttttttgtc attttgtttc ttctcgtacg agcttgctcc   7740
tgatcagcct atctcgcagc tgatgaatat cttgtggtag ggtttggga aaatcattcg   7800
agtttgatgt ttttcttggt atttcccact cctcttcaga gtacagaaga ttaagtgaga   7860
cgttcgtttg tgctccgga                                                7879
```

```
<210> SEQ ID NO 13
<211> LENGTH: 7963
<212> TYPE: DNA
<213> ORGANISM: Artificial Sequence
<220> FEATURE:
<223> OTHER INFORMATION: MMV78

<400> SEQUENCE: 13

aattgacacc ttacgattat ttagagagta tttattagtt ttattgtatg tatacggatg     60
ttttattatc tatttatgcc cttatattct gtaactatcc aaaagtccta tcttatcaag    120
ccagcaatct atgtccgcga acgtcaacta aaaataagct ttttatgctg ttctctcttt    180
ttttcccttc ggtataatta taccttgcat ccacagattc tcctgccaaa ttttgcataa    240
tcctttacaa catggctata tgggagcact tagcgccctc caaaacccat attgcctacg    300
catgtatagg tgttttttcc acaatatttt ctctgtgctc tctttttatt aaagagaagc    360
```

```
tctatatcgg agaagcttct gtggccgtta tattcggcct tatcgtggga ccacattgcc    420
tgaattggtt tgccccggaa gattggggaa acttggatct gattacctta gctgcaggta    480
ccactgagcg tcagaccccg tagaaaagat caaaggatct tcttgagatc cttttttttct   540
gcgcgtaatc tgctgcttgc aaacaaaaaa accaccgcta ccagcggtgg tttgtttgcc    600
ggatcaagag ctaccaactc tttttccgaa ggtaactggc ttcagcagag cgcagatacc    660
aaatactgtt cttctagtgt agccgtagtt aggccaccac ttcaagaact ctgtagcacc    720
gcctacatac ctcgctctgc taatcctgtt accagtggct gctgccagtg gcgataagtc    780
gtgtcttacc gggttggact caagacgata gttaccggat aaggcgcagc ggtcgggctg    840
aacggggggt tcgtgcacac agcccagctt ggagcgaacg acctacaccg aactgagata    900
cctacagcgt gagctatgag aaagcgccac gcttcccgaa gggagaaagg cggacaggta    960
tccggtaagc ggcagggtcg gaacaggaga gcgcacgagg gagcttccag ggggaaacgc   1020
ctggtatctt tatagtcctg tcgggtttcg ccacctctga cttgagcgtc gatttttgtg   1080
atgctcgtca ggggggcgga gcctatggaa aaacgccagc aacgcggcct ttttacggtt   1140
cctggccttt tgctggcctt ttgctcacat gtcgcacaaa cgaaggtttc acttaatctt   1200
ctgtactctg aagaggagtg ggaaatacca agaaaaacat caaactcgaa tgattttccc   1260
aaacccctac cacaagatat tcatctgctg cgagataggc tgatcaggag caagctcgta   1320
cgagaagaaa caaaatgaca aaaaaaatcc tatactatat aggttacaaa taaaaaagta   1380
tcaaaaatga agcctgcatc tctcaggcaa atggcattct gacatcctct tgaaaattat   1440
cattctaatt ctgacaatgt gcatggcctc ctaaactctt gacctctctc atgcagccac   1500
ttattggaaa cccacttatt accgactaag acgggacaag cagcatgtct agtgctgtaa   1560
tcaccttctc cagatgcaaa cagattgtac caaaatacgg ccgtgccctt tttaggccaa   1620
acagaagcac ctacctcagg gaaaactgtg gctcctccag caagcacatc ggacatatag   1680
aacaaccacg ttgcgattct atttccagta cctagctcct taaaagcatc aggctcgtcc   1740
tttctggcga aatcaaagtg ggttcatac tgaccgccca caccatagtt ggcaacttgt    1800
agttcctcag cagtgcttac gtcaagacca gtcaaatctt gaatacgcat attgatacgg   1860
ctgaccacgg gattctcgta accggacaac catgctgatt tagagacacg atattgtgcg   1920
gtagtcaatt ttccagtctc agggtcatgg acggtagccc tactcaatct tggtttggcc   1980
aagtctttca caacctctat ttctgcatcg gagatgatgt catgaaaacg aatgattcta   2040
ggcttgtccc attcatcttc ctgtttcgct ggagcaagaa tgaattttgg gttacggttc   2100
ccatcatgat atctacagaa cagctttttc tgtctccttg gagtcatctt gataccctct   2160
cctctacaca gcatttcata cttttgtctc tctgggaggt agtcaacagc tgcacctttt   2220
tttttcagag tggtcttttg atcggattgg tcatcggacg aggacttatt tgcgtccttt   2280
tccttagcca tgatgtattc aaagtatttc agattaccgt tagctctttg atgctccggg   2340
tccagctcca acaacttttt agttaaaagt agagctttgt ccagatcacc ttgctggtaa   2400
acagcgtatg ataagtaatc caaaactgaa accttatcaa cggtagaaac ttcaccttcg   2460
tccaactgac gcagagcttg ctccatccat aattctgtgt gatagtagtc ggcttctgta   2520
tatgcgactt ttcccaattc aaaacaatct tccacagtga ggaaggactt atgcttcaca   2580
ccaggtaaat cacccttcga tatcgtgtcg gtgtccaaat tgtatgtgtc ctgcaatcgc   2640
aacaaagctt ttgctgctcc tacttggtcc tcatcgtttg gaaagtattg tctttgaatt   2700
```

-continued gttaagttag aaatgaatcc atcactcata tctttaagta ccaagttttc caattctgac 2760
cactctgtat taagtctctt catcagcttg aaagcattca ctgggtgacc cacaaaaccc 2820
tcaggatctt ttgttgcagt actagtcaat ctatcgagtt tctctgccca ctttttgatt 2880
tgctccaact tatcctcttc agctttgata tagtctttaa ggcttgtaac taggtctttt 2940
tctgtgtgaa tcaaatcagt catctgtcct atagaagtga agaagcctgg gtgagccagt 3000
gactgtggca acaaaatacc aacgactagg atataccaaa tcatttttga tgtttgatag 3060
tttgataaga gtgaacttta gtgtttagag gggttataat ttgttgtaac tggttttggt 3120
cttaagttaa aacgaacttg ttatattaaa cacaacggtc actcaggata caagaatagg 3180
aaagaaaaac tttaaactgg ggacatgttg tctttatata atttggcggt taacccttaa 3240
tgcccgtttc cgtctcttca tgataacaaa gctgcccatc tatgactgaa tgtggagaag 3300
tatcggaaca acccttcact aaggatatct aggctaaact cattcgcgcc ttagatttct 3360
ccaaggtatc ggttaagttt cctctttcgt actggctaac gatggtgttg ctcaacaaag 3420
ggatggaacg gcagctaaag ggagtgcatg gaatgacttt aattggctga gaaagtgttc 3480
tatttgtccg aatttctttt ttctattatc tgttcgtttg ggcggatctc tccagtgggg 3540
ggtaaatgga agatttctgt tcatggggta aggaagctga aatccttcgt ttcttatagg 3600
ggcaagtata ctaaatctcg gaacattgaa tggggtttac tttcattggc tacagaaatt 3660
attaagtttg ttatggggtg aagttaccag taattttcat tttttcactt caacttttgg 3720
ggtatttctg tggggtagca tagagcaatg atataaacaa caattgagtg acaggtctac 3780
tttgttctca aaaggccata accatctgtt tgcatctctt atcaccacac catcctcctc 3840
atctggcctt caattgtggg gaacaactag catcccaaca ccagactaac tccacccaga 3900
tgaaaccagt tgtcgcttac cagtcaatga atgttgagct aacgttcctt gaaactcgaa 3960
tgatcccagc cttgctgcgt atcatccctc cgctattccg ccgcttgctc caaccatgtt 4020
tccgcctttt tcgaacaagt tcaaatacct atctttggca ggacttttcc tcctgccttt 4080
tttagcctca gctctcggtt agcctctagg caaattctgg tcttcatacc tatatcaact 4140
tttcatcaga tagcctttgg gttcaaaaaa gaactaaagc aggatgcctg atatataaat 4200
cccagatgat ctgcttttga aactattttc agtatcttga ttcgtttact tacaaacaac 4260
tattgttgat tttatctgga gaataatcga acaaaatgag attcccatct attttcaccg 4320
ctgtcttgtt cgctgcctcc tctgcattgg ctgcccctgt taacactacc actgaagacg 4380
agactgctca aattccagct gaagcagtta tcggttactc tgaccttgag ggtgatttcg 4440
acgtcgctgt tttgcctttc tctaactcca ctaacaacgg tttgttgttc attaacacca 4500
ctatcgcttc cattgctgct aaggaagagg gtgtctctct cgagaaaaga gaggccgaag 4560
ctgcacccga tgaggaagat catgttttag tattgcataa aggaaatttc gatgaagctt 4620
tggccgctca caaatatctg ctcgtcgagt tttacgctcc ctggtgcggt cattgtaagg 4680
cccttgcacc agagtacgcc aaggcagctg gtaagttaaa ggccgaaggt tcagagatca 4740
gattagcaaa agttgatgct acagaagagt ccgatcttgc tcaacaatac ggggttcgag 4800
gatacccaac aattaagttt ttcaaaaatg gtgatactgc ttccccaaag gaatatactg 4860
ctggtagaga ggcagacgac atagtcaact ggctcaaaaa gagaacgggc ccagctgcgt 4920
ctacattaag cgacggagca gcagccgaag ctcttgtgga atctagtgaa gttgctgtaa 4980
tcggtttctt taaggacatg gaatctgatt cagctaaaca gttcctttta gcagctgaag 5040
caatcgatga catccctttc ggaatcacct caaatagtga cgtgttcagc aagtaccaac 5100

-continued

```
ttgacaaaga tggagtggtc ttgttcaaaa agtttgacga aggcagaaac aatttcgagg   5160
gtgaggttac aaaggagaaa ctgcttgatt tcattaaaca taaccaacta cccttagtta   5220
tcgaattcac tgaacaaact gctcctaaga ttttcggtgg agaaatcaaa acacatatct   5280
tgttgttttt gccaaagtcc gtatcggatt atgaaggtaa actctccaat ttcaaaaagg   5340
ccgctgagag ctttaagggc aagattttgt tcatctttat tgactcagac cacacagaca   5400
atcagaggat tttggagttt ttcggtttga aaaaggagga atgtccagca gtccgtttga   5460
tcaccttgga ggaggagatg accaaataca aaccagagtc ggatgagttg actgccgaga   5520
agataacaga attttgtcac agatttctgg aaggtaagat caagcctcat cttatgtctc   5580
aagagttgcc tgatgactgg gataagcaac cagttaaagt attggtgggt aaaaactttg   5640
aggaagtggc cttcgacgag aaaaaaaatg tctttgttga attctatgct ccgtggtgtg   5700
gtcactgtaa gcagctggca ccaatttggg ataaactggg tgaaacttac aaagatcacg   5760
aaaacattgt tattgcaaag atggacagta ctgctaacga agtggaggct gtgaaagttc   5820
actccttccc tacgctgaag ttctttcctg catctgctga cagaactgtt atcgactata   5880
atggagagag gacattggat ggttttaaaa agtttcttga atccggaggt caagacggag   5940
ctggtgacga cgatgatttg gaagatctgg aggaggctga ggaacctgat cttgaggagg   6000
atgacgacca gaaggcagtc aaagatgaac tgtgataagg ggcggccgct caagaggatg   6060
tcagaatgcc atttgcctga gagatgcagg cttcattttt gatacttttt tatttgtaac   6120
ctatatagta taggattttt tttgtcattt tgtttcttct cgtacgagct tgctcctgat   6180
cagcctatct cgcagcagat gaatatcttg tggtaggggt ttgggaaaat cattcgagtt   6240
tgatgttttt cttggtattt cccactcctc ttcagagtac agaagattaa gtgaaacctt   6300
cgtttgtgcg gatccttcag taatgtcttg tttcttttgt tgcagtggtg agccattttg   6360
acttcgtgaa agtttcttta gaatagttgt ttccagaggc caaacattcc acccgtagta   6420
aagtgcaagc gtaggaagac caagactggc ataaatcagg tataagtgtc gagcactggc   6480
aggtgatctt ctgaaagttt ctactagcag ataagatcca gtagtcatgc atatggcaac   6540
aatgtaccgt gtggatctaa gaacgcgtcc tactaacctt cgcattcgtt ggtccagttt   6600
gttgttatcg atcaacgtga caaggttgtc gattccgcgt aagcatgcat acccaaggac   6660
gcctgttgca attccaagtg agccagttcc aacaatcttt gtaatattag agcacttcat   6720
tgtgttgcgc ttgaaagtaa aatgcgaaca aattaagaga taatctcgaa accgcgactt   6780
caaacgccaa tatgatgtgc ggcacacaat aagcgttcat atccgctggg tgactttctc   6840
gctttaaaaa attatccgaa aaaattttct agagtgttga cactttatac ttccggctcg   6900
tataatacga caaggtgtaa ggaggactaa accatgaaaa agccagagct tacagcaacg   6960
agcgttgaga aattcttgat tgaaaagttt gattcagttt ccgacctgat gcagttgtct   7020
gagggtgaag agtcaagagc cttttcgttc gatgtgggtg gtagaggtta cgtccttagg   7080
gtgaactctt gtgccgatgg tttttacaaa gatagatatg tttacagaca tttcgcatcc   7140
gcagcactcc ccatcccaga agtattggac attggagagt tttccgaatc cttgacctat   7200
tgcatctctc gacgtgccca aggtgtcact ttacaagact tgccggagac tgaacttcca   7260
gcagttttac aacctgtagc agaggctatg gacgctattg ctgctgctga tttgtctcaa   7320
acaagtggat tcggcccttt tggtcctcag ggtatcgggc aatacacaac ttggagagac   7380
tttatctgtg ctatcgcaga cccacatgtg tatcactggc aaaccgtcat ggatgacact   7440
```

```
gtatcggcta gtgtggccca agctcttgat gagctaatgc tgtgggctga ggactgtcca   7500
gaagtgaggc acttggttca cgcagacttt ggatccaata atgttctgac agataacgga   7560
cgtataacag ctgtcattga ctggtccgaa gctatgttcg gtgattcaca atatgaagtc   7620
gctaacatat tcttttggcg tccctggtta gcatgtatgg agcaacaaac tagatatttc   7680
gaacgtagac atcctgaact agctggatct ccaagattga gagcttacat gctgaggatc   7740
ggtttggatc agctgtacca gagcttggta gacggaaatt tcgacgacgc cgcatgggcg   7800
caaggtagat gcgatgccat tgtgagaagt ggtgctggca ctgttggtag aacccagatt   7860
gcaagacgtt cagctgctgt ttggacggat ggttgtgttg aggttttggc agattccgga   7920
aatcgtagac ctagcactag gccaagagct aaggaataat agc                     7963
```

<210> SEQ ID NO 14
<211> LENGTH: 5508
<212> TYPE: DNA
<213> ORGANISM: Artificial Sequence
<220> FEATURE:
<223> OTHER INFORMATION: MMV94

<400> SEQUENCE: 14

```
aacatccaaa gacgaaaggt tgaatgaaac ctttttgcca tccgacatcc acaggtccat     60
tctcacacat aagtgccaaa cgcaacagga ggggatacac tagcagcaga ccgttgcaaa    120
cgcaggacct ccactcctct tctcctcaac acccactttt gccatcgaaa aaccagccca    180
gttattgggc ttgattggag ctcgctcatt ccaattcctt ctattaggct actaacacca    240
tgactttatt agcctgtcta tcctggcccc cctggcgagg ttcatgtttg tttatttccg    300
aatgcaacaa gctccgcatt acacccgaac atcactccag atgagggctt tctgagtgtg    360
gggtcaaata gtttcatgtt ccccaaatgg cccaaaactg acagtttaaa cgctgtcttg    420
gaacctaata tgacaaaagc gtgatctcat ccaagatgaa ctaagtttgg ttcgttgaaa    480
tgctaacggc cagttggtca aaaagaaact tccaaaagtc ggcataccgt ttgtcttgtt    540
tggtattgat tgacgaatgc tcaaaaataa tctcattaat gcttagcgca gtctctctat    600
cgcttctgaa ccccggtgca cctgtgccga aacgcaaatg gggaaacacc cgctttttgg    660
atgattatgc attgtctcca cattgtatgc ttccaagatt ctggtgggaa tactgctgat    720
agcctaacgt tcatgatcaa aatttaactg ttctaacccc tacttgacag caatatataa    780
acagaaggaa gctgccctgt cttaaacctt tttttttatc atcattatta gcttactttc    840
ataattgcga ctggttccaa ttgacaagct tttgatttta acgactttta acgacaactt    900
gagaagatca aaaaacaact aattattgaa agaattcatg ttctctccaa ttttgtcctt    960
ggaaattatt ttagctttgg ctactttgca atctgtcttc gctgcccccg acgaggagga   1020
ccacgtcctg gtgctccata agggcaactt cgacgaggcg ctggcggccc acaagtacct   1080
gctggtggag ttctacgccc catggtgcgg ccactgcaag gctctggccc cggagtatgc   1140
caaagcagct gggaagctga aggcagaagg ttctgagatc agactggcca aggtggatgc   1200
cactgaagag tctgacctgg cccagcagta tggtgtccga ggctacccca ccatcaagtt   1260
cttcaagaat ggagacacag cttcccccaa agagtacaca gctggccgag aagcggatga   1320
tatcgtgaac tggctgaaga agcgcacggg ccccgctgcc agcacgctgt ccgacggggc   1380
tgctgcagag gccttggtgg agtccagtga ggtggccgtc attggcttct tcaaggacat   1440
ggagtcggac tccgcaaagc agttcttgtt ggcagcagag gccattgatg acatcccctt   1500
cgggatcaca tctaacagcg atgtgttctc caaataccag ctggacaagg atggggttgt   1560
```

```
cctctttaag aagtttgacg aaggccggaa caactttgag ggggaggtca ccaaagaaaa   1620
gcttctggac ttcatcaagc acaaccagtt gcccctggtc attgagttca ccgagcagac   1680
agccccgaag atcttcggag gggaaatcaa gactcacatc ctgctgttcc tgccgaaaag   1740
cgtgtctgac tatgagggca agctgagcaa cttcaaaaaa gcggctgaga gcttcaaggg   1800
caagatcctg tttatcttca tcgacagcga ccacactgac aaccagcgca tcctggaatt   1860
cttcggccta aagaaagagg agtgcccggc cgtgcgcctc atcacgctgg aggaggagat   1920
gaccaaatat aagccagagt cagatgagct gacggcagag aagatcaccg agttctgcca   1980
ccgcttcctg gagggcaaga ttaagcccca cctgatgagc caggagctgc ctgacgactg   2040
ggacaagcag cctgtcaaag tgctggttgg gaagaacttt gaagaggttg cttttgatga   2100
gaaaaagaac gtctttgtag agttctatgc cccgtggtgc ggtcactgca agcagctggc   2160
ccccatctgg gataagctgg gagagacgta caaggaccac gagaacatag tcatcgccaa   2220
gatggactcc acggccaacg aggtggaggc ggtgaaagtg cacagcttcc ccacgctcaa   2280
gttcttcccc gccagcgccg acaggacggt catcgactac aatggggagc ggacactgga   2340
tggttttaag aagttcctgg agagtggtgg ccaggatggg gccggagatg atgacgatct   2400
agaagatctt gaagaagcag aagagcctga tctggaggaa gatgatgatc aaaaagctgt   2460
gaaagatgaa ctgtaagcgg ccgctcaaga ggatgtcaga atgccatttg cctgagagat   2520
gcaggcttca tttttgatac ttttttattt gtaacctata tagtatagga tttttttgt    2580
cattttgttt cttctcgtac gagcttgctc ctgatcagcc tatctcgcag cagatgaata   2640
tcttgtggta ggggtttggg aaaatcattc gagtttgatg tttttcttgg tatttcccac   2700
tcctcttcag agtacagaag attaagtgaa accttcgttt gtgcggatcc ttcagtaatg   2760
tcttgtttct tttgttgcag tggtgagcca ttttgacttc gtgaaagttt ctttagaata   2820
gttgtttcca gaggccaaac attccacccg tagtaaagtg caagcgtagg aagaccaaga   2880
ctggcataaa tcaggtataa gtgtcgagca ctggcaggtg atcttctgaa agtttctact   2940
agcagataag atccagtagt catgcatatg gcaacaatgt accgtgtgga tctaagaacg   3000
cgtcctacta accttcgcat tcgttggtcc agtttgttgt tatcgatcaa cgtgacaagg   3060
ttgtcgattc cgcgtaagca tgcataccca aggacgcctg ttgcaattcc aagtgagcca   3120
gttccaacaa tctttgtaat attagagcac ttcattgtgt tgcgcttgaa agtaaaatgc   3180
gaacaaatta agagataatc tcgaaaccgc gacttcaaac gccaatatga tgtgcggcac   3240
acaataagcg ttcatatccg ctgggtgact ttctcgcttt aaaaaattat ccgaaaaaat   3300
tttctagagt gttgacactt tatacttccg gctcgtataa tacgacaagg tgtaaggagg   3360
actaaaccat gggtaaggaa aagactcacg tttcgaggcc gcgattaaat tccaacatgg   3420
atgctgattt atatgggtat aaatgggctc gcgataatgt cgggcaatca ggtgcgacaa   3480
tctatcgatt gtatgggaag cccgatgcgc cagagttgtt tctgaaacat ggcaaaggta   3540
gcgttgccaa tgatgttaca gatgagatgg tcagactaaa ctggctgacg gaatttatgc   3600
ctcttccgac catcaagcat tttatccgta ctcctgatga tgcatggtta ctcaccactg   3660
cgatccccgg caaaacagca ttccaggtat tagaagaata tcctgattca ggtgaaaata   3720
ttgttgatgc gctggcagtg ttcctgcgcc ggttgcattc gattcctgtt tgtaattgtc   3780
cttttaacag cgatcgcgta tttcgtctcg ctcaggcgca atcacgaatg aataacggtt   3840
tggttgatgc gagtgatttt gatgacgagc gtaatggctg gcctgttgaa caagtctgga   3900
```

aagaaatgca taagcttttg ccattctcac cggattcagt cgtcactcat ggtgatttct 3960
cacttgataa ccttattttt gacgagggga aattaatagg ttgtattgat gttggacgag 4020
tcggaatcgc agaccgatac caggatcttg ccatcctatg gaactgcctc ggtgagtttt 4080
ctccttcatt acagaaacgg ctttttcaaa aatatggtat tgataatcct gatatgaata 4140
aattgcagtt tcatttgatg ctcgatgagt ttttctaaca attgacacct tacgattatt 4200
tagagagtat ttattagttt tattgtatgt atacggatgt tttattatct atttatgccc 4260
ttatattctg taactatcca aaagtcctat cttatcaagc cagcaatcta tgtccgcgaa 4320
cgtcaactaa aaataagctt tttatgctgt tctctctttt tttcccttcg gtataattat 4380
accttgcatc cacagattct cctgccaaat tttgcataat cctttacaac atggctatat 4440
gggagcactt agcgccctcc aaaacccata ttgcctacgc atgtataggt gtttttttcca 4500 caatattttc tctgtgctct ctttttatta aagagaagct ctatatcgga gaagcttctg 4560
tggccgttat attcggcctt atcgtgggac cacattgcct gaattggttt gccccggaag 4620
attggggaaa cttggatctg attaccttag ctgcaggtac cactgagcgt cagaccccgt 4680
agaaaagatc aaaggatctt cttgagatcc tttttttctg cgcgtaatct gctgcttgca 4740
aacaaaaaaa ccaccgctac cagcggtggt ttgtttgccg gatcaagagc taccaactct 4800
ttttccgaag gtaactggct tcagcagagc gcagatacca aatactgttc ttctagtgta 4860
gccgtagtta ggccaccact tcaagaactc tgtagcaccg cctacatacc tcgctctgct 4920
aatcctgtta ccagtggctg ctgccagtgg cgataagtcg tgtcttaccg ggttggactc 4980
aagacgatag ttaccggata aggcgcagcg gtcgggctga acggggggtt cgtgcacaca 5040
gcccagcttg gagcgaacga cctacaccga actgagatac ctacagcgtg agctatgaga 5100
aagcgccacg cttcccgaag ggagaaaggc ggacaggtat ccggtaagcg gcagggtcgg 5160
aacaggagag cgcacgaggg agcttccagg gggaaacgcc tggtatcttt atagtcctgt 5220
cgggtttcgc cacctctgac ttgagcgtcg atttttgtga tgctcgtcag gggggcggag 5280
cctatggaaa aacgccagca acgcggcctt tttacggttc ctggcctttt gctggccttt 5340
tgctcacatg ttctttcctg cggtacccag atccaattcc cgctttgact gcctgaaatc 5400
tccatcgcct acaatgatga catttggatt tggttgactc atgttggtat tgtgaaatag 5460
acgcagatcg ggaacactga aaaatacaca gttattattc atttaaat 5508

<210> SEQ ID NO 15
<211> LENGTH: 7605
<212> TYPE: DNA
<213> ORGANISM: Artificial Sequence
<220> FEATURE:
<223> OTHER INFORMATION: MMV156

<400> SEQUENCE: 15
tgcaggtacc actgagcgtc agaccccgta gaaaagatca aaggatcttc ttgagatcct 60 tttttctgc gcgtaatctg ctgcttgcaa acaaaaaaac caccgctacc agcggtggtt 120
tgtttgccgg atcaagagct accaactctt tttccgaagg taactggctt cagcagagcg 180
cagataccaa atactgttct tctagtgtag ccgtagttag gccaccactt caagaactct 240
gtagcaccgc ctacatacct cgctctgcta atcctgttac cagtggctgc tgccagtggc 300
gataagtcgt gtcttaccgg gttggactca agacgatagt taccggataa ggcgcagcgg 360
tcgggctgaa cggggggttc gtgcacacag cccagcttgg agcgaacgac ctacaccgaa 420
ctgagatacc tacagcgtga gctatgagaa agcgccacgc ttcccgaagg gagaaaggcg 480

```
gacaggtatc cggtaagcgg cagggtcgga acaggagagc gcacgaggga gcttccaggg    540
ggaaacgcct ggtatcttta tagtcctgtc gggtttcgcc acctctgact tgagcgtcga    600
tttttgtgat gctcgtcagg ggggcggagc ctatggaaaa acgccagcaa cgcggccttt    660
ttacggttcc tggccttttg ctggcctttt gctcacatgt tctttcctgc ggtacccaga    720
tccaattccc gctttgactg cctgaaatct ccatcgccta caatgatgac atttggattt    780
ggttgactca tgttggtatt gtgaaataga cgcagatcgg gaacactgaa aaatacacag    840
ttattattca tttcagaagc gatagagaga ctgcgctaag cattaatgag attatttttg    900
agcattcgtc aatcaatacc aaacaagaca aacggtatgc cgacttttgg aagtttcttt    960
ttgaccaact ggccgttagc atttcaacga accaaactta gttcatcttg gatgagatca   1020
cgcttttgtc atattaggtt ccaagacagc gtttaaactg tcagttttgg gccatttggg   1080
gaacatgaaa ctatttgacc ccacactcag aaagccctca tctggagtga tgttcgggtg   1140
taatgcggag cttgttgcat tcggaaataa acaaacatga acctcgccag gggggccagg   1200
atagacaggc taataaagtc atggtgttag tagcctaata gaaggaattg gaataaatga   1260
cccttgtgac tgacactttg ggagtcccta ttctacttag tctcatatcg catgaaactt   1320
ttgataaatt attttctgat aggaattttt catcagatat tatcatcgcg gcttacgtaa   1380
taacaaaaaa aattgatgga gtctatacta ggctaacata aactaagtta ttaattaaac   1440
aaaacaaaac gtactagcat tactgtcata tataagggct cctaactaaa actgtaaaga   1500
cttcccgtaa aattatcatt ctaattctga caatgtgcat ggcctcctaa actcttgacc   1560
tctctcatgc agccacttat tggaaaccca cttattaccg actaagacgg gacaagcagc   1620
atgtctagtg ctgtaatcac cttctccaga tgcaaacaga ttgtaccaaa atacggccgt   1680
gcccttttta ggccaaacag aagcacctac ctcagggaaa actgtggctc ctccagcaag   1740
cacatcggac atatagaaca accacgttgc gattctattt ccagtaccta gctccttaaa   1800
agcatcaggc tcgtcctttc tggcgaaatc aaagtggggt tcatactgac cgcccacacc   1860
atagttggca acttgtagtt cctcagcagt gcttacgtca agaccagtca aatcttgaat   1920
acgcatattg atacggctga ccacgggatt ctcgtaaccg gacaaccatg ctgatttaga   1980
gacacgatat tgtgcggtag tcaattttcc agtctcaggg tcatggacgg tagccctact   2040
caatcttggt ttggccaagt ctttcacaac ctctatttct gcatcggaga tgatgtcatg   2100
aaaacgaatg attctaggct tgtcccattc atcttcctgt ttcgctggag caagaatgaa   2160
ttttgggtta cggttcccat catgatatct acagaacagc tttttctgtc tccttggagt   2220
catcttgata ccctctcctc tacacagcat ttcatacttt tgtctctctg ggaggtagtc   2280
aacagctgca cctttttttt tcagagtggt cttttgatcg gattggtcat cggacgagga   2340
cttatttgcg tccttttcct tagccatgat gtattcaaag tatttcagat taccgttagc   2400
tctttgatgc tccgggtcca gctccaacaa ctttttagtt aaaagtagag ctttgtccag   2460
atcaccttgc tggtaaacag cgtatgataa gtaatccaaa actgaaacct tatcaacggt   2520
agaaacttca ccttcgtcca actgacgcag agcttgctcc atccataatt ctgtgtgata   2580
gtagtcggct tctgtatatg cgacttttcc caattcaaaa caatcttcca cagtgaggaa   2640
ggacttatgc ttcacaccag gtaaatcacc cttcgatatc gtgtcggtgt ccaaattgta   2700
tgtgtcctgc aatcgcaaca aagcttttgc tgctcctact tggtcctcat cgtttggaaa   2760
gtattgtctt tgaattgtta agttagaaat gaatccatca ctcatatctt taagtaccaa   2820
```

```
gttttccaat tctgaccact ctgtattaag tctcttcatc agcttgaaag cattcactgg   2880
gtgacccaca aaaccctcag gatcttttgt tgcagtacta gtcaatctat cgagtttctc   2940
tgcccacttt ttgatttgct ccaacttatc ctcttcagct ttgatatagt ctttaaggct   3000
tgtaactagg tctttttctg tgtgaatcaa atcagtcatc tgtcctatag aagtgaagaa   3060
gcctgggtga gccagtgact gtggcaacaa aataccaacg actaggatat accaaatcat   3120
gcggcctgtt gtagttttaa tatagtttga gtatgagatg gaactcagaa cgaaggaatt   3180
atcaccagtt tatatattct gaggaaaggg tgtgtcctaa attggacagt cacgatggca   3240
ataaacgctc agccaatcag aatgcaggag ccataaattg ttgtattatt gctgcaagat   3300
ttatgtgggt tcacattcca ctgaatggtt ttcactgtag aattggtgtc ctagttgtta   3360
tgtttcgaga tgttttcaag aaaaactaaa atgcacaaac tgaccaataa tgtgccgtcg   3420
cgcttggtac aaacgtcagg attgccacca ctttttttcgc actctggtac aaaagttcgc   3480
acttcccact cgtatgtaac gaaaaacaga gcagtctatc cagaacgaga caaattagcg   3540
cgtactgtcc cattccataa ggtatcatag gaaacgagag tcctcccccc atcacgtata   3600
tataaacaca ctgatatccc acatccgctt gtcaccaaac taatacatcc agttcaagtt   3660
acctaaacaa atcaaagcat gagattccca tctattttca ccgctgtctt gttcgctgcc   3720
tcctctgcat tggctgcacc cgatgaggaa gatcatgttt tagtattgca taaaggaaat   3780
ttcgatgaag ctttggccgc tcacaaatat ctgctcgtcg agttttacgc tccctggtgc   3840
ggtcattgta aggcccttgc accagagtac gccaaggcag ctggtaagtt aaaggccgaa   3900
ggttcagaga tcagattagc aaaagttgat gctacagaag agtccgatct tgctcaacaa   3960
tacggggttc gaggataccc aacaattaag tttttcaaaa atggtgatac tgcttcccca   4020
aaggaatata ctgctggtag agaggcagac gacatagtca actggctcaa aaagagaacg   4080
ggcccagctg cgtctacatt aagcgacgga gcagcagccg aagctcttgt ggaatctagt   4140
gaagttgctg taatcggttt ctttaaggac atggaatctg attcagctaa acagttcctt   4200
ttagcagctg aagcaatcga tgacatccct ttcggaatca cctcaaatag tgacgtgttc   4260
agcaagtacc aacttgacaa agatggagtg gtcttgttca aaaagtttga cgaaggcaga   4320
aacaatttcg agggtgaggt tacaaaggag aaactgcttg atttcattaa acataaccaa   4380
ctacccttag ttatcgaatt cactgaacaa actgctccta agattttcgg tggagaaatc   4440
aaaacacata tcttgttgtt tttgccaaag tccgtatcgg attatgaagg taaactctcc   4500
aatttcaaaa aggccgctga gagctttaag ggcaagattt tgttcatctt tattgactca   4560
gaccacacag acaatcagag gattttggag tttttcggtt tgaaaaagga ggaatgtcca   4620
gcagtccgtt tgatcacctt ggaggaggag atgaccaaat acaaaccaga gtcggatgag   4680
ttgactgccg agaagataac agaattttgt cacagatttc tggaaggtaa gatcaagcct   4740
catcttatgt ctcaagagtt gcctgatgac tgggataagc aaccagttaa agtattggtg   4800
ggtaaaaact ttgaggaagt ggccttcgac gagaaaaaaa atgtctttgt tgaattctat   4860
gctccgtggt gtggtcactg taagcagctg gcaccaattt gggataaact gggtgaaact   4920
tacaaagatc acgaaaacat tgttattgca aagatggaca gtactgctaa cgaagtggag   4980
gctgtgaaag ttcactcctt ccctacgctg aagttctttc ctgcatctgc tgacagaact   5040
gttatcgact ataatggaga gaggacattg gatggtttta aaaagtttct tgaatccgga   5100
ggtcaagacg gagctggtga cgacgatgat ttggaagatc tggaggaggc tgaggaacct   5160
gatcttgagg aggatgacga ccagaaggca gtcaaagatg aactgtgata aggggtcaag   5220
```

```
aggatgtcag aatgccattt gcctgagaga tgcaggcttc atttttgata ctttttttatt   5280
tgtaacctat atagtatagg attttttttg tcattttgtt tcttctcgta cgagcttgct   5340
cctgatcagc ctatctcgca gcagatgaat atcttgtggt aggggtttgg gaaaatcatt   5400
cgagtttgat gtttttcttg gtatttccca ctcctcttca gagtacagaa gattaagtga   5460
gaccttcgtt tgtgcggatc cttcagtaat gtcttgtttc ttttgttgca gtggtgagcc   5520
attttgactt cgtgaaagtt tctttagaat agttgtttcc agaggccaaa cattccaccc   5580
gtagtaaagt gcaagcgtag gaagaccaag actggcataa atcaggtata agtgtcgagc   5640
actggcaggt gatcttctga aagtttctac tagcagataa gatccagtag tcatgcatat   5700
ggcaacaatg taccgtgtgg atctaagaac gcgtcctact aaccttcgca ttcgttggtc   5760
cagtttgttg ttatcgatca acgtgacaag gttgtcgatt ccgcgtaagc atgcataccc   5820
aaggacgcct gttgcaattc caagtgagcc agttccaaca atctttgtaa tattagagca   5880
cttcattgtg ttgcgcttga aagtaaaatg cgaacaaatt aagagataat ctcgaaaccg   5940
cgacttcaaa cgccaatatg atgtgcggca cacaataagc gttcatatcc gctgggtgac   6000
tttctcgctt taaaaaatta tccgaaaaaa ttttctagag tgttgacact ttatacttcc   6060
ggctcgtata atacgacaag gtgtaaggag gactaaacca tgggtaaaaa gcctgaactc   6120
accgcgacgt ctgtcgagaa gtttctgatc gaaaagttcg acagcgtctc cgacctgatg   6180
cagctctcgg agggcgaaga atctcgtgct ttcagcttcg atgtaggagg gcgtggatat   6240
gtcctgcggg taaatagctg cgccgatggt ttctacaaag atcgttatgt ttatcggcac   6300
tttgcatcgg ccgcgctccc gattccggaa gtgcttgaca ttggggaatt cagcgagagc   6360
ctgacctatt gcatctcccg ccgtgcacag ggtgtcacgt tgcaagacct gcctgaaacc   6420
gaactgcccg ctgttctgca gccggtcgcg gaggccatgg atgcgatcgc tgcggccgat   6480
cttagccaga cgagcgggtt cggcccattc ggaccgcaag gaatcggtca atacactaca   6540
tggcgtgatt tcatatgcgc gattgctgat ccccatgtgt atcactggca aactgtgatg   6600
gacgacaccg tcagtgcgtc cgtcgcgcag gctctcgatg agctgatgct ttgggccgag   6660
gactgccccg aagtccggca cctcgtgcac gcggatttcg gctccaacaa tgtcctgacg   6720
gacaatggcc gcataacagc ggtcattgac tggagcgagg cgatgttcgg ggattcccaa   6780
tacgaggtcg ccaacatctt cttctggagg ccgtggttgg cttgtatgga gcagcagacg   6840
cgctacttcg agcggaggca tccggagctt gcaggatcgc cgcggctccg ggcgtatatg   6900
ctccgcattg gtcttgacca actctatcag agcttggttg acggcaattt cgatgatgca   6960
gcttgggcgc agggtcgatg cgacgcaatc gtccgatccg gagccgggac tgtcgggcgt   7020
acacaaatcg cccgcagaag cgcggccgtc tggaccgatg gctgtgtaga agtactcgcc   7080
gatagtggaa accgacgccc cagcactcgt ccgagggcaa aggaataaca attgacacct   7140
tacgattatt tagagagtat ttattagttt tattgtatgt atacggatgt tttattatct   7200
atttatgccc ttatattctg taactatcca aaagtcctat cttatcaagc cagcaatcta   7260
tgtccgcgaa cgtcaactaa aaataagctt tttatgctct tctctctttt tttcccttcg   7320
gtataattat accttgcatc cacagattct cctgccaaat tttgcataat cctttacaac   7380
atggctatat gggagcactt agcgccctcc aaaacccata ttgcctacgc atgtataggt   7440
gtttttttcca caatattttc tctgtgctct ctttttatta aagagaagct ctatatcgga   7500
gaagcttctg tggccgttat attcggcctt atcgtgggac cacattgcct gaattggttt   7560
```

gccccggaag attggggaaa cttggatctg attaccttag ctgca 7605

<210> SEQ ID NO 16
<211> LENGTH: 8743
<212> TYPE: DNA
<213> ORGANISM: Artificial Sequence
<220> FEATURE:
<223> OTHER INFORMATION: MMV191

<400> SEQUENCE: 16
ggatccttca gtaatgtctt gtttcttttg ttgcagtggt gagccatttt gacttcgtga 60
aagtttcttt agaatagttg tttccagagg ccaaacattc cacccgtagt aaagtgcaag 120
cgtaggaaga ccaagactgg cataaatcag gtataagtgt cgagcactgg caggtgatct 180
tctgaaagtt tctactagca gataagatcc agtagtcatg catatggcaa caatgtaccg 240
tgtggatcta agaacgcgtc ctactaacct tcgcattcgt tggtccagtt tgttgttatc 300
gatcaacgtg acaaggttgt cgattccgcg taagcatgca tacccaagga cgcctgttgc 360
aattccaagt gagccagttc caacaatctt tgtaatatta gagcacttca ttgtgttgcg 420
cttgaaagta aaatgcgaac aaattaagag ataatctcga aaccgcgact tcaaacgcca 480
atatgatgtg cggcacacaa taagcgttca tatccgctgg gtgactttct cgctttaaaa 540
aattatccga aaaaatttc tagacttctc ttccaaatat cgtctccaca aaatgggtaa 600
ggaaaagact cacgtttcga ggccgcgatt aaattccaac atggatgctg atttatatgg 660
gtataaatgg gctcgcgata atgtcgggca atcaggtgcg acaatctatc gattgtatgg 720
gaagcccgat gcgccagagt tgtttctgaa acatggcaaa ggtagcgttg ccaatgatgt 780
tacagatgag atggtcagac taaactggct gacggaattt atgcctcttc cgaccatcaa 840
gcattttatc cgtactcctg atgatgcatg gttactcacc actgcgatcc ccggcaaaac 900
agcattccag gtattagaag aatatcctga ttcaggtgaa aatattgttg atgcgctggc 960
agtgttcctg cgccggttgc attcgattcc tgtttgtaat tgtcctttta acagcgatcg 1020
cgtatttcgt ctcgctcagg cgcaatcacg aatgaataac ggtttggttg atgcgagtga 1080
ttttgatgac gagcgtaatg gctggcctgt tgaacaagtc tggaaagaaa tgcataagct 1140
tttgccattc tcaccggatt cagtcgtcac tcatggtgat ttctcacttg ataaccttat 1200
ttttgacgag gggaaattaa taggttgtat tgatgttgga cgagtcggaa tcgcagaccg 1260
ataccaggat cttgccatcc tatggaactg cctcggtgag ttttctcctt cattacagaa 1320
acggcttttt caaaaatatg gtattgataa tcctgatatg aataaattgc agtttcattt 1380
gatgctcgat gagtttttct aaaattgaca ccttacgatt atttagagag tatttattag 1440
ttttattgta tgtatacgga tgttttatta tctatttatg cccttatatt ctgtaactat 1500
ccaaaagtcc tatcttatca agccagcaat ctatgtccgc gaacgtcaac taaaaataag 1560
ctttttatgc tgttctctct ttttttccct tcggtataat tataccttgc atccacagat 1620
tctcctgcca aattttgcat aatcctttac aacatggcta tatgggagca cttagcgccc 1680
tccaaaaccc atattgccta cgcatgtata ggtgtttttt ccacaatatt ttctctgtgc 1740
tctcttttta ttaaagagaa gctctatatc ggagaagctt ctgtggccgt tatattcggc 1800
cttatcgtgg gaccacattg cctgaattgg tttgccccgg aagattgggg aaacttggat 1860
ctgattacct tagctgcatc agaattggtt aattggttgt aacactgacc cctatttgtt 1920
tatttttcta aatacattca aatatgtatc cgctcatgag acaataaccc tgataaatgc 1980
ttcaataata ttgaaaaagg aagaatatga gtattcaaca tttccgtgtc gcccttattc 2040

-continued cctttttgc ggcattttgc cttcctgttt ttgctcaccc agaaacgctg gtgaaagtaa 2100
aagatgctga agatcagttg ggtgcacgag tgggttacat cgaactggat ctcaacagcg 2160
gtaagatcct tgagagtttt cgccccgaag aacgttttcc aatgatgagc acttttaaag 2220
ttctgctatg tggcgcggta ttatcccgta ttgacgccgg gcaagagcaa ctcggtcgcc 2280
gcatacacta ttctcagaat gacttggttg agtactcacc agtcacagaa aagcatctta 2340
cggatggcat gacagtaaga gaattatgca gtgctgccat aaccatgagt gataacactg 2400
cggccaactt acttctgaca acgatcggag gaccgaagga gctaaccgct tttttgcaca 2460
acatggggga tcatgtaact cgccttgatc gttgggaacc ggagctgaat gaagccatac 2520
caaacgacga gcgtgacacc acgatgcctg tagcgatggc aacaacgttg cgcaaactat 2580
taactggcga actacttact ctagcttccc ggcaacaatt aatagactgg atggaggcgg 2640
ataaagttgc aggaccactt ctgcgctcgg cccttccggc tggctggttt attgctgata 2700
aatccggagc cggtgagcgt ggttctcgcg gtatcatcgc agcgctgggg ccagatggta 2760
agccctcccg tatcgtagtt atctacacga cggggagtca ggcaactatg gatgaacgaa 2820
atagacagat cgctgagata ggtgcctcac tgattaagca ttggtaaggt accactgagc 2880
gtcagacccc gtagaaaaga tcaaaggatc ttcttgagat cctttttttc tgcgcgtaat 2940
ctgctgcttg caaacaaaaa aaccaccgct accagcggtg gtttgtttgc cggatcaaga 3000
gctaccaact ctttttccga aggtaactgg cttcagcaga gcgcagatac caaatactgt 3060
tcttctagtg tagccgtagt taggccacca cttcaagaac tctgtagcac cgcctacata 3120
cctcgctctg ctaatcctgt taccagtggc tgctgccagt ggcgataagt cgtgtcttac 3180
cgggttggac tcaagacgat agttaccgga taaggcgcag cggtcgggct gaacgggggg 3240
ttcgtgcaca cagcccagct tggagcgaac gacctacacc gaactgagat acctacagcg 3300
tgagctatga gaaagcgcca cgcttcccga agggagaaag gcggacaggt atccggtaag 3360
cggcagggtc ggaacaggag agcgcacgag ggagcttcca gggggaaacg cctggtatct 3420
ttatagtcct gtcgggtttc gccacctctg acttgagcgt cgatttttgt gatgctcgtc 3480
aggggggcgg agcctatgga aaaacgccag caacgcggcc tttttacggt tcctggcctt 3540
ttgctggcct tttgctcaca atttaaatga cccttgtgac tgacactttg ggagtcccta 3600
ttctacttag tctcatatcg catgaaactt ttgataaatt attttctgat aggaattttt 3660
catcagatat tatcatcgcg gcttacgtaa taacaaaaaa aattgatgga gtctatacta 3720
ggctaacata aactaagtta ttaattaaac aaaacaaaac gtactagcat tactgtcata 3780
tataagggct cctaactaaa actgtaaaga cttcccgtaa aattatcatt ctaattctga 3840
caatgtgcat ggcctcctaa actcttgacc tctctcatgc agccacttat tggaaaccca 3900
cttattaccg actaagacgg gacaagcagc atgtctagtg ctgtaatcac cttctccaga 3960
tgcaaacaga ttgtaccaaa atacggccgt gccctttttta ggccaaacag aagcacctac 4020
ctcagggaaa actgtggctc ctccagcaag cacatcggac atatagaaca accacgttgc 4080
gattctattt ccagtaccta gctccttaaa agcatcaggc tcgtcctttc tggcgaaatc 4140
aaagtggggt tcatactgac cgcccacacc atagttggca acttgtagtt cctcagcagt 4200
gcttacgtca agaccagtca aatcttgaat acgcatattg atacggctga ccacgggatt 4260
ctcgtaaccg gacaaccatg ctgatttaga gacacgatat tgtgcggtag tcaattttcc 4320
agtctcaggg tcatggacgg tagccctact caatcttggt ttggccaagt ctttcacaac 4380

```
ctctatttct gcatcggaga tgatgtcatg aaaacgaatg attctaggct tgtcccattc   4440
atcttcctgt ttcgctggag caagaatgaa ttttgggtta cggttcccat catgatatct   4500
acagaacagc tttttctgtc tccttggagt catcttgata ccctctcctc tacacagcat   4560
ttcatacttt tgtctctctg ggaggtagtc aacagctgca cctttttttt tcagagtggt   4620
cttttgatcg gattggtcat cggacgagga cttatttgcg tccttttcct tagccatgat   4680
gtattcaaag tatttcagat taccgttagc tctttgatgc tccgggtcca gctccaacaa   4740
ctttttagtt aaaagtagag ctttgtccag atcaccttgc tggtaaacag cgtatgataa   4800
gtaatccaaa actgaaacct tatcaacggt agaaacttca ccttcgtcca actgacgcag   4860
agcttgctcc atccataatt ctgtgtgata gtagtcggct tctgtatatg cgacttttcc   4920
caattcaaaa caatcttcca cagtgaggaa ggacttatgc ttcacaccag gtaaatcacc   4980
cttcgatatc gtgtcggtgt ccaaattgta tgtgtcctgc aatcgcaaca aagcttttgc   5040
tgctcctact tggtcctcat cgtttggaaa gtattgtctt tgaattgtta agttagaaat   5100
gaatccatca ctcatatctt taagtaccaa gttttccaat tctgaccact ctgtattaag   5160
tctcttcatc agcttgaaag cattcactgg gtgacccaca aaaccctcag gatcttttgt   5220
tgcagtacta gtcaatctat cgagtttctc tgcccacttt ttgatttgct ccaacttatc   5280
ctcttcagct ttgatatagt ctttaaggct tgtaactagg tctttttctg tgtgaatcaa   5340
atcagtcatc tgtcctatag aagtgaagaa gcctgggtga gccagtgact gtggcaacaa   5400
aataccaacg actaggatat accaaatcat gcttttgttg ttgagtgaag cgagtgacgg   5460
aacggtaaaa tgtaagtaac aaaagaaaaa gagaaccagg ggggggagga gagtatgtat   5520
ttataccgta cggcaccagg cgaaaagcta taaacaaacc tttttcgcgg tatatttgtt   5580
tatatttcct attttaaact caaaatctgc cctaatctgg acttttcatg caaagttatg   5640
cacctgaggc aggaatgaag caggctcgac gacgaaaagg ctggaatggg taactatgga   5700
tcgattgatt tgtctgttga aatcttgatt tggcactcgt ttaaattaac attctgcatc   5760
atggtgaatt gcggtcacag gtactggttt ttcctgaagc tctaggcggt gttactgttc   5820
ccacaactta aaacctaaaa gaggtgggtg cttctttgcg tgggtgacca aaaataaaac   5880
cgactgccta gtggcattga taccttttt tgggtgttgt cctggaaacc actgaacgta   5940
tctgcgagat acaaaagtat ttttagataa gtggcaaatg caaaaaaatct gattggtcag   6000
ttaatgattg atgaacgact ttaaggttaa aaagcaaaat agtgactgct gccatgtgcc   6060
tgtatagcac atgaactgat tattctgttc ccacgctacg atgaaaacgc cttctctgcc   6120
gaaagattaa agctgcgcgg gaaaaaaaaa ttaactttac ggggcgagca cggttccccg   6180
aaacaaaaga tggttggctt tcacccagcg agctcactgg atgccagtta aaaatagtta   6240
ggtgggttca cctgtttttg tagaaatgtc ttggtgtcct cgaccaatca ggtagccatc   6300
cctgaaatac ctggctccgt ggcaacaccg aacgacctgc tggcaacgtt aaattctccg   6360
gggtaaaact taaatgtgga gtaatagaac cagaaacgtc tcttcccttc tctctccttc   6420
caccgcccgt taccgtccct aggaaatttt actctgctgg agagcttctt ctacggcccc   6480
cttgcagcaa tgctcttccc agcattacgt tgcgggtaaa acggaggtcg tgtacccgac   6540
ctagcagccc agggatggaa agtcccggcc gtcgctggca ataactgcgg gcggacgcat   6600
gtcttgagat tattggaaac caccagaatc gaatataaaa ggcgaacacc tttcccaatt   6660
ttggtttctc ctgacccaaa gactttaaat ttaatttatt tgtccctatt tcaatcaatt   6720
gaacaactat ggccgcatga gattcccatc tattttcacc gctgtcttgt tcgctgcctc   6780
```

ctctgcattg gctgcccctg ttaacactac cactgaagac gagactgctc aaattccagc 6840
tgaagcagtt atcggttact ctgaccttga gggtgatttc gacgtcgctg ttttgccttt 6900
ctctaactcc actaacaacg gtttgttgtt cattaacacc actatcgctt ccattgctgc 6960
taaggaagag ggtgtctctc tcgagaaaag agaggccgaa gctgcacccg atgaggaaga 7020
tcatgtttta gtattgcata aaggaaattt cgatgaagct ttggccgctc acaaatatct 7080
gctcgtcgag ttttacgctc cctggtgcgg tcattgtaag gcccttgcac cagagtacgc 7140
caaggcagct ggtaagttaa aggccgaagg ttcagagatc agattagcaa aagttgatgc 7200
tacagaagag tccgatcttg ctcaacaata cggggttcga ggatacccaa caattaagtt 7260
tttcaaaaat ggtgatactg cttccccaaa ggaatatact gctggtagag aggcagacga 7320
catagtcaac tggctcaaaa agagaacggg cccagctgcg tctacattaa gcgacggagc 7380
agcagccgaa gctcttgtgg aatctagtga agttgctgta atcggtttct ttaaggacat 7440
ggaatctgat tcagctaaac agttcctttt agcagctgaa gcaatcgatg acatcccttt 7500
cggaatcacc tcaaatagtg acgtgttcag caagtaccaa cttgacaaag atggagtggt 7560
cttgttcaaa aagtttgacg aaggcagaaa caatttcgag ggtgaggtta caaaggagaa 7620
actgcttgat ttcattaaac ataaccaact acccttagtt atcgaattca ctgaacaaac 7680
tgctcctaag attttcggtg gagaaatcaa aacacatatc ttgttgtttt tgccaaagtc 7740
cgtatcggat tatgaaggta aactctccaa tttcaaaaag gccgctgaga gctttaaggg 7800
caagattttg ttcatcttta ttgactcaga ccacacagac aatcagagga ttttggagtt 7860
tttcggtttg aaaaaggagg aatgtccagc agtccgtttg atcaccttgg aggaggagat 7920
gaccaaatac aaaccagagt cggatgagtt gactgccgag aagataacag aattttgtca 7980
cagatttctg gaaggtaaga tcaagcctca tcttatgtct caagagttgc ctgatgactg 8040
ggataagcaa ccagttaaag tattggtggg taaaaacttt gaggaagtgg ccttcgacga 8100
gaaaaaaaat gtctttgttg aattctatgc tccgtggtgt ggtcactgta agcagctggc 8160
accaatttgg gataaactgg gtgaaactta caaagatcac gaaaacattg ttattgcaaa 8220
gatggacagt actgctaacg aagtggaggc tgtgaaagtt cactccttcc ctacgctgaa 8280
gttctttcct gcatctgctg acagaactgt tatcgactat aatggagaga ggacattgga 8340
tggttttaaa aagtttcttg aatccggagg tcaagacgga gctggtgacg acgatgattt 8400
ggaagatctg gaggaggctg aggaacctga tcttgaggag gatgacgacc agaaggcagt 8460
caaagatgaa ctgtgataag gggtcaagag gatgtcagaa tgccatttgc ctgagagatg 8520
caggcttcat tttgatactt tttttatttg taacctatat agtataggat tttttttgtc 8580
attttgtttc ttctcgtacg agcttgctcc tgatcagcct atctcgcagc agatgaatat 8640
cttgtggtag ggtttggga aaatcattcg agtttgatgt ttttcttggt atttcccact 8700
cctcttcaga gtacagaaga ttaagtgaga ccttcgtttg tgc 8743

<210> SEQ ID NO 17
<211> LENGTH: 12068
<212> TYPE: DNA
<213> ORGANISM: Artificial Sequence
<220> FEATURE:
<223> OTHER INFORMATION: MMV208

<400> SEQUENCE: 17
cggatgtttt attatctatt tatgccctta tattctgtaa ctatccaaaa gtcctatctt 60

```
atcaagccag caatctatgt ccgcgaacgt caactaaaaa taagcttttt atgctcttct    120
ctcttttttt cccttcggta taattatacc ttgcatccac agattctcct gccaaatttt    180
gcataatcct ttacaacatg gctatatggg agcacttagc gccctccaaa acccatattg    240
cctacgcatg tataggtgtt ttttccacaa tattttctct gtgctctctt tttattaaag    300
agaagctcta tatcggagaa gcttctgtgg ccgttatatt cggccttatc gtgggaccac    360
attgcctgaa ttggtttgcc ccggaagatt ggggaaactt ggatctgatt accttagctg    420
cagaaaaggg taccactgag cgtcagaccc cgtagaaaag atcaaaggat cttcttgaga    480
tccttttttt ctgcgcgtaa tctgctgctt gcaaacaaaa aaaccaccgc taccagcggt    540
ggtttgtttg ccggatcaag agctaccaac tctttttccg aaggtaactg gcttcagcag    600
agcgcagata ccaaatactg ttcttctagt gtagccgtag ttaggccacc acttcaagaa    660
ctctgtagca ccgcctacat acctcgctct gctaatcctg ttaccagtgg ctgctgccag    720
tggcgataag tcgtgtctta ccgggttgga cccaagacga tagttaccgg ataaggcgca    780
gcggtcgggc tgaacggggg gttcgtgcac acagcccagc ttggagcgaa cgacctacac    840
cgaactgaga tacctacagc gtgagctatg agaaagcgcc acgcttcccg aagggagaaa    900
ggcggacagg tatccggtaa gcggcagggt cggaacagga gagcgcacga gggagcttcc    960
agggggaaac gcctggtatc tttatagtcc tgtcgggttt cgccacctct gacttgagcg   1020
tcgatttttg tgatgctcgt caggggggcg gagcctatgg aaaaacgcca gcaacgcggc   1080
ctttttacgg ttcctggcct tttgctggcc ttttgctcat atgtaagctt tgaacactta   1140
tgtaagctcg aaaccagtta ggtaagcagc tttgtaagca atctggacaa tatgtaagcg   1200
ggttacgtaa acagttatgt aagcagaaaa atttcaaacg acaaaacttg ggtctacag    1260
acacagtagc cagaagattg cactaccatt cgactcctca tgacccactc tttcgatcca   1320
tgtagttagg ttaccgtttt tcctaatatt taaggatgtt gaaaattcat tttcattttt   1380
tttcgttttt aagattttct cacaactctt ccaaagatta ctagttgact tttcaaaata   1440
tttagggtat ttttctcact ttttcctagc aaactccaat tggtgggttc agtgcaatgg   1500
agtaccacct tgcaaccaca acgtaatagc taacttgtgg ccaccatgtc tggttgtaga   1560
gataattgga ttctaatgtg gatcacatga ctactcacgt gtcaaaaacc caacctgact   1620
tggcccagct tagcaagaat atttcgaatc cactcttgtg gcctagtgga caactgggac   1680
ctagggaccc ttgtgactga cactttggga gtccctattc tacttagtct catatcgcat   1740
gaaacttttg ataaattatt ttctgatagg aatttttcat cagatattat catcgcggct   1800
tacgtaataa caaaaaaaat tgatggagtc tatactaggc taacataaac taagttatta   1860
attaaacaaa acaaaacgta ctagcattac tgtcatatat aagggctcct aactaaaact   1920
gtaaagactt cccgtaaaat tatcattcta attctgacaa tgtgcatggc ctcctaaact   1980
cttgacctct ctcatgcagc cacttattgg aaacccactt attaccgact aagacgggac   2040
aagcagcatg tctagtgctg taatcacctt ctccagatgc aaacagattg taccaaaata   2100
cggccgtgcc ctttttaggc caaacagaag caccaacctc agggaaaact gtggctcctc   2160
cagcaagcac atcggacata tagaacaacc acgttgcgat tctatttcca gtacctagct   2220
ccttaaaagc atcaggctcg tcctttctgg cgaaatcaaa gtggggttca tactgaccgc   2280
ccacaccata gttggcaact tgtagttctt cagcagtgct tacgtcaaga ccagtcaaat   2340
cttgaatacg catattgata cggctgacca cgggattctc gtaaccggac aaccatgctg   2400
atttagagac acgatattgt gcggtagtca attttccagt ctcagggtca tggacggtag   2460
```

ccctactcaa tcttggtttg gccaagtctt tcacaacctc tatttctgca tcggagatga 2520
tgtcatgaaa acgaatgatt ctaggcttgt cccattcatc ttcctgtttc gctggagcaa 2580
gaatgaattt tgggttacgg ttcccatcat gatatctaca gaacagcttt ttctgtctcc 2640
ttggagtcat cttgataccc tctcctctac acagcatttc atacttttgt ctctctggga 2700
ggtagtcaac agccgcacct tttttttca gagtggtctt ttgatcggat tggtcatcgg 2760
acgaggactt atttgcgtcc ttttccttag ccatgatgta ttcaaagtat ttcagattac 2820
cgttagctct ttgatgctcc gggtccagct ccaacaactt tttagttaaa agtagagctt 2880
tgtccagatc accttgctgg taaacagcgt atgataagta atccaaaact gaaaccttat 2940
caacggtaga aacttcacct tcgtccaact gacgtagagc ttgctccatc cataattctg 3000
tgtgatagta gtcggcttct gtatatgcga cttttcccaa ttcaaaacaa tcttccacag 3060
tgaggaagga cttatgcttc acaccaggta aatcaccctt cgatatcgtg tcggtgtcca 3120
aattgtatgt gtcctgcaat cgcaacaaag cttttgctgc tcctacttgg tcctcatcgt 3180
ttggaaagta ttgtctttga attgttaagt tagaaatgaa tccatcactc atatctttaa 3240
gtaccaagtt ttccaattct gaccactctg tattaagtct cttcatcagc ttgaaagcat 3300
tcactgggtg acccacaaaa ccctcaggat cttttgttgc agtacttgtc aatctatcga 3360
gtttctctgc ccactttttg atttgctcca acttatcctc ttcagctttg atatagtctt 3420
taaggcttgt aactaggtct ttttctgtgt gaatcaaatc agtcatctgt cctatagaag 3480
tgaagaagcc tgggtgagcc agtgactgtg gcaacaaaat accaacgact aggatatacc 3540
aaatcatgcg gccgcatggc ccccgacgag gaggaccacg tcctggtgct ccataagggc 3600
aacttcgacg aggcgctggc ggcccacaag tacctgctgg tggagttcta cgccccatgg 3660
tgcggccact gcaaggctct ggccccggag tatgccaaag cagctgggaa gctgaaggca 3720
gaaggttctg agatcagact ggccaaggtg gatgccactg aagagtctga cctggcccag 3780
cagtatggtg tccgaggcta ccccaccatc aagttcttca agaatggaga cacagcttcc 3840
cccaaagagt acacagctgg ccgggaagcg gatgatatcg tgaactggct gaagaagcgc 3900
acgggccccg ctgccagcac gctgtccgac ggggctgctg cagaggcttt ggtggagtcc 3960
agtgaggtgg ccgtcattgg cttcttcaag gatatggagt cggactccgc aaagcagttc 4020
ttcttggcag cagaggtcat tgatgacatc cccttcggga tcacatctaa cagcgatgtg 4080
ttctccaaat accagctgga caaggatggg gttgtcctct ttaagaagtt tgacgaaggc 4140
cggaacaact ttgaggggga ggtcaccaaa gaaaagcttc tggacttcat caagcacaac 4200
cagttgcccc tggtcattga gttcaccgag cagacagccc cgaagatctt cggaggggaa 4260
atcaagactc acatcctgct gttcctgccg aaaagcgtgt ctgactatga gggcaagctg 4320
agtaacttca aaaaagcggc tgagagcttc aagggcaaga tcctgtttat cttcatcgac 4380
agcgaccaca ctgacaacca gcgcatcctg gagttcttcg gcctaaagaa agaggagtgc 4440
ccggccgtgc gcctcatcac gctggaggag gagatgacca aatataagcc agagtcagat 4500
gagctgacgg cagagaagat caccgagttc tgccaccgct tcctggaggg caagattaag 4560
ccccacctga tgagccagga gctgcctgac gactgggaca agcagcctgt caaagtgctg 4620
gttgggaaga actttgaaga ggttgctttt gatgagaaaa agaacgtctt tgtagagttc 4680
tatgccccgt ggtgcggtca ctgcaagcag ctggccccca tctgggataa gctgggagag 4740
acgtacaagg accacgagaa catagtcatc gccaagatgg actccacggc caacgaggtg 4800

-continued gaggcggtga aagtgcacag cttccccacg ctcaagttct tccccgccag cgccgacagg 4860
acggtcatcg actacaatgg ggaacggaca ctggatggtt ttaagaagtt cctggagagt 4920
ggtggccagg atggggccgg agatgatgac gatcttgaag atcttgaaga agcagaagag 4980
cctgatctgg aggaagatga tgatcaaaaa gctgtgaaag atgaactgta atcaagagga 5040
tgtcagaatg ccatttgcct gagagatgca ggcttcattt ttgatacttt tttatttgta 5100
acctatatag tataggattt tttttgtcat tttgtttctt ctcgtacgag cttgctcctg 5160
atcagcctat ctcgcagcag atgaatatct tgtggtaggg gtttgggaaa atcattcgag 5220
tttgatgttt ttcttggtat ttcccactcc tcttcagagt acagaagatt aagtgagacc 5280
ttcgtttgtg ccgatcggtt cagaagcgat agagagactg cgctaagcat taatgagatt 5340
atttttgagc attcgtcaat caataccaaa caagacaaac ggtatgccga cttttggaag 5400
tttctttttg accaactggc cgttagcatt tcaacgaacc aaacttagtt catcttggat 5460
gagatcacgc ttttgtcata ttaggttcca agacagcgtt taaactgtca gttttgggcc 5520
atttggggaa catgaaacta tttgacccca cactcagaaa gccctcatct ggagtgatgt 5580
tcgggtgtaa tgcggagctt gttgcattcg gaaataaaca aacatgaacc tcgccagggg 5640
ggccaggata gacaggctaa taaagtcatg gtgttagtag cctaatagaa ggaattggaa 5700
tgagcggatc caatgtatct aaacgcaaac tccgagctgg aaaaatgtta ccggcgatgc 5760
gcggacaatt tagaggcggc gatcaagaaa cacctgctgg gcgagcagtc tggagcacag 5820
tcttcgatgg gcccgagatc ccaccgcgtt cctgggtacc gggacgtgag gcagcgcgac 5880
atccatcaaa tataccaggc gccaaccgag tctctcggaa aacagcttct ggatatcttc 5940
cgctggcggc gcaacgacga ataatagtcc ctggaggtga cggaatatat atgtgtggag 6000
ggtaaatctg acagggtgta gcaaaggtaa tattttccta aaacatgcaa tcggctgccc 6060
cgcaacggga aaaagaatga ctttggcact cttcaccaga gtggggtgtc ccgctcgtgt 6120
gtgcaaatag gctcccactg gtcaccccgg attttgcaga aaaacagcaa gttccggggt 6180
gtctcactgg tgtccgccaa taagaggagc cggcaggcac ggagtctaca tcaagctgtc 6240
tccgatacac tcgactacca tccgggtctc tcagagaggg gaatggcact ataaataccg 6300
cctccttgcg ctctctgcct tcatcaatca aatcggatcc atgtcttttg tccaaaaggg 6360
tacttggtta ctttttgctc tgttgcaccc aactgttatt ctcgcacaac aggaagcagt 6420
agatggtggt tgctcacatt taggtcaatc ttacgcagat agagatgtat ggaaacctga 6480
accatgtcaa atttgcgtgt gtgactcagg ttcagtgctc tgcgacgata tcatatgtga 6540
cgaccaggaa ttggactgtc caaacccaga gataccattc ggtgaatgtt gtgctgtttg 6600
tccacagcca ccaactgctc ctacaagacc tccaaacggt caaggtccac aaggtcctaa 6660
aggtgatccg ggtccacctg gtattcctgg tagaaatggt gaccctggac ctcccggttc 6720
cccaggtagc ccaggatcac ctgggcctcc tggaatatgt gaatcctgcc caactggtgg 6780
tcagaactat agcccacaat acgaggccta cgacgtcaaa tctggtgttg ctggaggagg 6840
tattgcaggc taccctggtc ccgcagggcc cccaggtccg ccgggtccgc ccggaacatc 6900
aggtcatccc ggagcccctg gtgcaccagg ttatcaggga ccgcccggag agcctggaca 6960
agctggtccc gctggacccc ctggtccacc aggtgctatt ggaccaagtg gtcctgccgg 7020
aaaagacggt gaatccggta gacctggtag acccggcgaa aggggtttcc caggtcctcc 7080
cggaatgaag ggtccagccg gtatgcccgg ttttcctggg atgaagggtc acagaggatt 7140
tgatggtaga aacggagaga aaggcgaaac cggtgctccc ggactgaagg gtgaaaacgg 7200
tgtccctggt gagaacggcg ctcctggacc tatgggtcca cgtggtgctc caggagaaag 7260
aggcagacca ggattgcctg gtgcagctgg tgctagaggt aacgatggtg cccgtggttc 7320
cgatggacaa cccgggccac ccggccctcc aggtaccgct ggatttcctg gaagccctgg 7380
tgctaagggg gaggttggtc cggctggtag tcccggaagt agcggtgccc caggtcaaag 7440
aggcgaacca ggccctcagg gtcacgcagg agcacctgga ccgcctggtc ctcctggttc 7500
gaatggttcg cctggaggaa aaggtgaaat ggggcccgca ggaatccccg gtgcgcctgg 7560
tcttattggt gccaggggtc ctccaggccc gccaggtaca aatggtgtac ccggacagcg 7620
aggagcagct ggtgaacctg gtaaaaacgg tgccaaagga gatccaggtc ctcgtggaga 7680
gcgtggtgaa gctggctctc ccggtatcgc cggtccaaaa ggtgaggacg gtaaggacgg 7740
ttcccctggt gagccaggtg cgaacggact gccaggtgca gccggagagc gaggagtccc 7800
aggattcagg ggaccagccg gtgctaacgg cttgcctggt gaaaaagggc cccctggtga 7860
taggggagga cccggtccag caggccctcg tggagttgct ggtgagcctg gacgtgacgg 7920
tttaccagga gggccaggtt tgaggggtat tcccgggtcc cctggcggtc ctggatcgga 7980
tggaaaacca gggccaccag gttcgcaggg tgaaacagga cgtccaggcc cacccggctc 8040
acctggtcca aggggtcagc ctggtgtcat gggtttcccc ggtccaaagg gtaatgacgg 8100
agcaccgggt aaaaatggtg aacgtggtgg cccaggtggt ccaggacccc aaggtccagc 8160
tggaaaaaac ggtgagacag gtcctcaagg acctccagga cctaccggtc ctagcggaga 8220
taagggagat acgggaccgc caggacctca aggattgcaa ggtttgcctg gtacatctgg 8280
ccctcccgga gaaaatggta agcctggaga gccaggacca aaaggcgaag ctggagcccc 8340
aggtatcccc ggaggtaagg gagactcagg tgctccgggt gagcgtggtc ctccgggtgc 8400
cggtggtcca cctggaccta gaggtggtgc cgggccgcca ggtcctgaag gtggtaaagg 8460
tgctgctggt ccaccgggac cgcctggctc tgctggtact cctggcttgc agggaatgcc 8520
aggagagaga ggtggacctg gaggtcccgg tccgaagggt gataaagggg agccaggatc 8580
atccggtgtt gacggcgcac ctggtaaaga cggaccaagg ggaccaacgg gtccaatcgg 8640
accaccagga cccgctggcc agccaggaga taaaggcgag tccggagcac ccggtgttcc 8700
tggtatagct ggacccaggg gtggtcccgg tgaaagaggt gaacagggcc caccgggtcc 8760
cgccggtttc cctggcgccc ctggtcaaaa tggagaacca ggtgcaaagg gcgagagagg 8820
agccccagga gaaaagggtg agggaggacc acccggtgct gccggtccag ctgggggttc 8880
aggtcctgct ggaccaccag gtccacaggg cgttaaaggt gagagaggaa gtccaggtgg 8940
tcctggagct gctggattcc caggtggccg tggacctcct ggtccccctg gatcgaatgg 9000
taatcctggt ccgccaggta gttcgggtgc tcctgggaag gacggtccac ctggcccccc 9060
aggtagtaac ggtgcacctg gtagtccagg tatatccgga cctaaaggag attccggtcc 9120
accaggcgaa agaggggccc caggcccaca gggtccacca ggagcccccg gtcctctggg 9180
tattgctggt cttactggtg cacgtggact ggccggtcca cccggaatgc ctggagcaag 9240
aggttcacct ggaccacaag gtattaaagg agagaacggt aaacctggac cttccggtca 9300
aaacggagag cggggacccc caggccccca aggtctgcca ggactagctg gtaccgcagg 9360
ggaaccagga agagatggaa atccaggttc agacggacta cccggtagag atggtgcacc 9420
gggggccaag ggcgacaggg gtgagaatgg atctcctggt gcgccagggg caccaggcca 9480
cccaggtccc ccaggtcctg tgggccctgc tggaaagtca ggtgacaggg gagagacagg 9540

```
cccggctggt ccatctggcg cacccggacc agctggttcc agaggcccac ctggtccgca   9600
aggccctaga ggtgacaagg gagagactgg agaacgaggt gctatgggta tcaagggtca   9660
tagaggtttt ccgggtaatc ccggcgcccc aggttctcct ggtccagctg gccatcaagg   9720
tgcagtcgga tcgcccggcc cagccggtcc caggggccct gttggtccat ccggtcctcc   9780
aggaaaggat ggtgcttctg gacacccagg acctatcgga cctccgggtc ctagaggtaa   9840
tagaggagaa cgtggttccg agggtagtcc tggtcaccct ggtcaacctg gcccaccagg   9900
gcctccaggt gcacccggtc catgttgtgg tgcaggcggt gtggctgcaa ttgctggtgt   9960
gggtgctgaa aaggccggcg gtttcgctcc atattatggt gatgaaccga ttgattttaa  10020
gatcaatact gacgaaatca tgacttcctt aaagtccgtt aatggtcaaa ttgagtctct  10080
aatctcccca gatggttcac gtaaaaatcc tgctagaaat tgtagagatt tgaagttttg  10140
tcaccccgag ttgcagtccg gtgagtactg ggtggacccc aatcaaggtt gtaagttaga  10200
cgctattaaa gtttactgca atatggagac aggagaaact tgcatcagcg cttctccatt  10260
gactatccca caaaaaaatt ggtggactga ctctggagct gagaaaaagc atgtatggtt  10320
cggggaatcg atggaaggtg gtttccaatt cagctacggt aaccctgaac ttcctgaaga  10380
tgttcttgac gttcaattgg catttctgag attgttgtcc agtcgtgcaa gccaaaacat  10440
tacataccat tgcaaaaatt ccatcgcata tatggatcat gctagcggaa atgtgaaaaa  10500
ggcattgaag ctgatgggat caaatgaagg tgaatttaaa gcagagggta attctaagtt  10560
tacttacact gtattggagg atggttgtac gaagcataca ggtgaatggg gtaaaacagt  10620
gtttcaatat caaacccgca aagcagttag attgccaatc gtcgatatcg caccatacga  10680
cattggagga ccagatcaag agttcggagc tgacatcggt ccggtgtgtt tcctttgata  10740
atcaagagga tgtcagaatg ccatttgcct gagagatgca ggcttcattt ttgatacttt  10800
tttatttgta acctatatag tataggattt tttttgtcat tttgtttctt ctcgtacgag  10860
cttgctcctg atcagcctat ctcgcagctg atgaatatct tgtggtaggg gtttgggaaa  10920
atcattcgag tttgatgttt ttcttggtat ttcccactcc tcttcagagt acagaagatt  10980
aagtgagacg ttcgtttgtg cccgcggatt taaatgatcc ttcagtaatg tcttgtttct  11040
tttgttgcag tggtgagcca ttttgacttc gtgaaagttt ctttagaata gttgtttcca  11100
gaggccaaac attccacccg tagtaaagtg caagcgtagg aagaccaaga ctggcataaa  11160
tcaggtataa gtgtcgagca ctggcaggtg atcttctgaa agtttctact agcagataag  11220
atccagtagt catgcatatg gcaacaatgt accgtgtgga tctaagaacg cgtcctacta  11280
accttcgcat tcgttggtcc agtttgttgt tatcgatcaa cgtgacaagg ttgtcgattc  11340
cgcgtaagca tgcataccca aggacgcctg ttgcaattcc aagtgagcca gttccaacaa  11400
tctttgtaat attagagcac ttcattgtgt tgcgcttgaa agtaaaatgc gaacaaatta  11460
agagataatc tcgaaaccgc gacttcaaac gccaatatga tgtgcggcac acaataagcg  11520
ttcatatccg ctgggtgact ttctcgcttt aaaaaattat ccgaaaaaat tttctagagt  11580
gttgttactt tatacttccg gctcgtataa tacgacaagg tgtaaggagg actaaaccat  11640
ggctaaactc acctctgctg ttccagtcct gactgctcgt gatgttgctg gtgctgttga  11700
gttctggact gataggctcg gtttctcccg tgacttcgta gaggacgact ttgccggtgt  11760
tgtacgtgac gacgttaccc tgttcatctc cgcagttcag gaccaggttg tgccagacaa  11820
cactctggca tgggtatggg ttcgtggtct ggacgaactg tacgctgagt ggtctgaggt  11880
cgtgtctacc aacttccgtg atgcatctgg tccagctatg accgagatcg gtgaacagcc  11940
```

ctggggtcgt gagtttgcac tgcgtgatcc agctggtaac tgcgtgcatt tcgtcgcaga 12000
agagcaggac taacaattga caccttacga ttatttagag agtatttatt agttttattg 12060
tatgtata 12068

<210> SEQ ID NO 18
<211> LENGTH: 5735
<212> TYPE: DNA
<213> ORGANISM: Artificial Sequence
<220> FEATURE:
<223> OTHER INFORMATION: MMV84

<400> SEQUENCE: 18
aacatccaaa gacgaaaggt tgaatgaaac ctttttgcca tccgacatcc acaggtccat 60
tctcacacat aagtgccaaa cgcaacagga ggggatacac tagcagcaga ccgttgcaaa 120
cgcaggacct ccactcctct tctcctcaac acccactttt gccatcgaaa aaccagccca 180
gttattgggc ttgattggag ctcgctcatt ccaattcctt ctattaggct actaacacca 240
tgactttatt agcctgtcta tcctggcccc cctggcgagg ttcatgtttg tttatttccg 300
aatgcaacaa gctccgcatt acacccgaac atcactccag atgagggctt tctgagtgtg 360
gggtcaaata gtttcatgtt ccccaaatgg cccaaaactg acagtttaaa cgctgtcttg 420
gaacctaata tgacaaaagc gtgatctcat ccaagatgaa ctaagtttgg ttcgttgaaa 480
tgctaacggc cagttggtca aaaagaaact tccaaaagtc ggcataccgt ttgtcttgtt 540
tggtattgat tgacgaatgc tcaaaaataa tctcattaat gcttagcgca gtctctctat 600
cgcttctgaa ccccggtgca cctgtgccga aacgcaaatg gggaaacacc cgctttttgg 660
atgattatgc attgtctcca cattgtatgc ttccaagatt ctggtgggaa tactgctgat 720
agcctaacgt tcatgatcaa aatttaactg ttctaacccc tacttgacag caatatataa 780
acagaaggaa gctgccctgt cttaaacctt ttttttatc atcattatta gcttactttc 840
ataattgcga ctggttccaa ttgacaagct tttgatttta acgactttta acgacaactt 900
gagaagatca aaaaacaact aattattgaa agaattcaaa acgaaaatga gattcccatc 960
tattttcacc gctgtcttgt tcgctgcctc ctctgcattg gctgcccctg ttaacactac 1020
cactgaagac gagactgctc aaattccagc tgaagcagtt atcggttact ctgaccttga 1080
gggtgatttc gacgtcgctg ttttgccttt ctctaactcc actaacaacg gtttgttgtt 1140
cattaacacc actatcgctt ccattgctgc taaggaagag ggtgtctctc tcgagaaaag 1200
agaggccgaa gctgcacccg atgaggaaga tcatgtttta gtattgcata aaggaaattt 1260
cgatgaagct ttggccgctc acaaatatct gctcgtcgag ttttacgctc cctggtgcgg 1320
tcattgtaag gcccttgcac cagagtacgc caaggcagct ggtaagttaa aggccgaagg 1380
ttcagagatc agattagcaa aagttgatgc tacagaagag tccgatcttg ctcaacaata 1440
cggggttcga ggatacccaa caattaagtt tttcaaaaat ggtgatactg cttccccaaa 1500
ggaatatact gctggtagag aggcagacga catagtcaac tggctcaaaa agagaacggg 1560
cccagctgcg tctacattaa gcgacggagc agcagccgaa gctcttgtgg aatctagtga 1620
agttgctgta atcggtttct ttaaggacat ggaatctgat tcagctaaac agttcctttt 1680
agcagctgaa gcaatcgatg acatcccttt cggaatcacc tcaaatagtg acgtgttcag 1740
caagtaccaa cttgacaaag atggagtggt cttgttcaaa aagtttgacg aaggcagaaa 1800
caatttcgag ggtgaggtta caaaggagaa actgcttgat ttcattaaac ataaccaact 1860

-continued

```
acccttagtt atcgaattca ctgaacaaac tgctcctaag attttcggtg gagaaatcaa   1920
aacacatatc ttgttgtttt tgccaaagtc cgtatcggat tatgaaggta aactctccaa   1980
tttcaaaaag gccgctgaga gctttaaggg caagattttg ttcatcttta ttgactcaga   2040
ccacacagac aatcagagga ttttggagtt tttcggtttg aaaaaggagg aatgtccagc   2100
agtccgtttg atcaccttgg aggaggagat gaccaaatac aaaccagagt cggatgagtt   2160
gactgccgag aagataacag aattttgtca cagatttctg gaaggtaaga tcaagcctca   2220
tcttatgtct caagagttgc ctgatgactg ggataagcaa ccagttaaag tattggtggg   2280
taaaaacttt gaggaagtgg ccttcgacga gaaaaaaaat gtctttgttg aattctatgc   2340
tccgtggtgt ggtcactgta agcagctggc accaatttgg gataaactgg gtgaaactta   2400
caaagatcac gaaaacattg ttattgcaaa gatggacagt actgctaacg aagtggaggc   2460
tgtgaaagtt cactccttcc ctacgctgaa gttctttcct gcatctgctg acagaactgt   2520
tatcgactat aatggagaga ggacattgga tggttttaaa aagtttcttg aatccggagg   2580
tcaagacgga gctggtgacg acgatgattt ggaagatctg gaggaggctg aggaacctga   2640
tcttgaggag gatgacgacc agaaggcagt caaagatgaa ctgtgataag gggggttaaa   2700
ggggcggccg ctcaagagga tgtcagaatg ccatttgcct gagagatgca ggcttcattt   2760
ttgatacttt tttatttgta acctatatag tataggattt tttttgtcat tttgtttctt   2820
ctcgtacgag cttgctcctg atcagcctat ctcgcagcag atgaatatct tgtggtaggg   2880
gtttgggaaa atcattcgag tttgatgttt ttcttggtat ttcccactcc tcttcagagt   2940
acagaagatt aagtgaaacc ttcgtttgtg cggatccttc agtaatgtct tgtttctttt   3000
gttgcagtgg tgagccattt tgacttcgtg aaagtttctt tagaatagtt gtttccagag   3060
gccaaacatt ccacccgtag taaagtgcaa gcgtaggaag accaagactg gcataaatca   3120
ggtataagtg tcgagcactg gcaggtgatc ttctgaaagt ttctactagc agataagatc   3180
cagtagtcat gcatatggca acaatgtacc gtgtggatct aagaacgcgt cctactaacc   3240
ttcgcattcg ttggtccagt ttgttgttat cgatcaacgt gacaaggttg tcgattccgc   3300
gtaagcatgc atacccaagg acgcctgttg caattccaag tgagccagtt ccaacaatct   3360
ttgtaatatt agagcacttc attgtgttgc gcttgaaagt aaaatgcgaa caaattaaga   3420
gataatctcg aaaccgcgac ttcaaacgcc aatatgatgt gcggcacaca ataagcgttc   3480
atatccgctg ggtgactttc tcgctttaaa aaattatccg aaaaaatttt ctagagtgtt   3540
gttactttat acttccggct cgtataatac gacaaggtgt aaggaggact aaaccatggg   3600
taaggaaaag actcacgttt cgaggccgcg attaaattcc aacatggatg ctgatttata   3660
tgggtataaa tgggctcgcg ataatgtcgg gcaatcaggt gcgacaatct atcgattgta   3720
tgggaagccc gatgcgccag agttgtttct gaaacatggc aaaggtagcg ttgccaatga   3780
tgttacagat gagatggtca gactaaactg gctgacggaa tttatgcctc ttccgaccat   3840
caagcatttt atccgtactc ctgatgatgc atggttactc accactgcga tccccggcaa   3900
aacagcattc caggtattag aagaatatcc tgattcaggt gaaaatattg ttgatgcgct   3960
ggcagtgttc ctgcgccggt tgcattcgat tcctgtttgt aattgtcctt ttaacagcga   4020
tcgcgtattt cgtctcgctc aggcgcaatc acgaatgaat aacggtttgg ttgatgcgag   4080
tgattttgat gacgagcgta atggctggcc tgttgaacaa gtctggaaag aaatgcataa   4140
gcttttgcca ttctcaccgg attcagtcgt cactcatggt gatttctcac ttgataacct   4200
tatttttgac gaggggaaat taataggttg tattgatgtt ggacgagtcg gaatcgcaga   4260
```

ccgataccag gatcttgcca tcctatggaa ctgcctcggt gagttttctc cttcattaca 4320
gaaacggctt tttcaaaaat atggtattga taatcctgat atgaataaat tgcagtttca 4380
tttgatgctc gatgagtttt tctaacaatt gacaccttac gattatttag agagtattta 4440
ttagttttat tgtatgtata cggatgtttt attatctatt tatgccctta tattctgtaa 4500
ctatccaaaa gtcctatctt atcaagccag caatctatgt ccgcgaacgt caactaaaaa 4560
taagcttttt atgctgttct ctcttttttt cccttcggta taattatacc ttgcatccac 4620
agattctcct gccaaatttt gcataatcct ttacaacatg gctatatggg agcacttagc 4680
gccctccaaa acccatattg cctacgcatg tataggtgtt ttttccacaa tattttctct 4740
gtgctctctt tttattaaag agaagctcta tatcggagaa gcttctgtgg ccgttatatt 4800
cggccttatc gtgggaccac attgcctgaa ttggtttgcc ccggaagatt ggggaaactt 4860
ggatctgatt accttagctg caggtaccac tgagcgtcag accccgtaga aaagatcaaa 4920
ggatcttctt gagatccttt ttttctgcgc gtaatctgct gcttgcaaac aaaaaaacca 4980
ccgctaccag cggtggtttg tttgccggat caagagctac caactctttt tccgaaggta 5040
actggcttca gcagagcgca gataccaaat actgttcttc tagtgtagcc gtagttaggc 5100
caccacttca agaactctgt agcaccgcct acatacctcg ctctgctaat cctgttacca 5160
gtggctgctg ccagtggcga taagtcgtgt cttaccgggt tggactcaag acgatagtta 5220
ccggataagg cgcagcggtc gggctgaacg gggggttcgt gcacacagcc cagcttggag 5280
cgaacgacct acaccgaact gagataccta cagcgtgagc tatgagaaag cgccacgctt 5340
cccgaaggga gaaaggcgga caggtatccg gtaagcggca gggtcggaac aggagagcgc 5400
acgagggagc ttccaggggg aaacgcctgg tatctttata gtcctgtcgg gtttcgccac 5460
ctctgacttg agcgtcgatt tttgtgatgc tcgtcagggg ggcggagcct atggaaaaac 5520
gccagcaacg cggccttttt acggttcctg gccttttgct ggccttttgc tcacatgttc 5580
tttcctgcgg tacccagatc caattcccgc tttgactgcc tgaaatctcc atcgcctaca 5640
atgatgacat ttggatttgg ttgactcatg ttggtattgt gaaatagacg cagatcggga 5700
acactgaaaa atacacagtt attattcatt taaat 5735

<210> SEQ ID NO 19
<211> LENGTH: 7204
<212> TYPE: DNA
<213> ORGANISM: Artificial Sequence
<220> FEATURE:
<223> OTHER INFORMATION: MMV150

<400> SEQUENCE: 19
aaaaataagc tttttatgct cttctctctt tttttccctt cggtataatt ataccttgca 60
tccacagatt ctcctgccaa attttgcata atcctttaca acatggctat atgggagcac 120
ttagcgccct ccaaaaccca tattgcctac gcatgtatag gtgttttttc cacaatattt 180
tctctgtgct ctctttttat taaagagaag ctctatatcg gagaagcttc tgtggccgtt 240
atattcggcc ttatcgtggg accacattgc ctgaattggt ttgccccgga agattgggga 300
aacttggatc tgattacctt agctgcagaa aagggtacca ctgagcgtca gaccccgtag 360
aaaagatcaa aggatcttct tgagatcctt tttttctgcg cgtaatctgc tgcttgcaaa 420
caaaaaaacc accgctacca gcggtggttt gtttgccgga tcaagagcta ccaactcttt 480
ttccgaaggt aactggcttc agcagagcgc agataccaaa tactgttctt ctagtgtagc 540

```
cgtagttagg ccaccacttc aagaactctg tagcaccgcc tacatacctc gctctgctaa    600
tcctgttacc agtggctgct gccagtggcg ataagtcgtg tcttaccggg ttggacccaa    660
gacgatagtt accggataag gcgcagcggt cgggctgaac ggggggttcg tgcacacagc    720
ccagcttgga gcgaacgacc tacaccgaac tgagatacct acagcgtgag ctatgagaaa    780
gcgccacgct tcccgaaggg agaaaggcgg acaggtatcc ggtaagcggc agggtcggaa    840
caggagagcg cacgagggag cttccagggg gaaacgcctg gtatctttat agtcctgtcg    900
ggtttcgcca cctctgactt gagcgtcgat ttttgtgatg ctcgtcaggg gggcggagcc    960
tatggaaaaa cgccagcaac gcggcctttt tacggttcct ggccttttgc tggccttttg   1020
ctcacatgta ttttatgtaa gctttgaaca cttatgtaag ctcgaaacca gttaggtaag   1080
cagctttgta agcaatctgg acaatatgta agcgggttac gtaaacagtt atgtaagcag   1140
aaaaatttca aacgacaaaa cttggggtct acagacacag tagccagaag attgcactac   1200
cattcgactc ctcatgaccc actctttcga tccatgtagt taggttaccg tttttcctaa   1260
tatttaagga tgttgaaaat tcattttcat ttttttcgt ttttaagatt ttctcacaac   1320
tcttccaaag attactagtt gacttttcaa aatatttagg gtatttttct cactttttcc   1380
tagcaaactc caattggtgg gttcagtgca atggagtacc accttgcaac cacaacgtaa   1440
tagctaactt gtggccacca tgtctggttg tagagataat tggattctaa tgtggatcac   1500
atgactactc acgtgtcaaa aacccaacct gacttggccc agcttagcaa gaatatttcg   1560
aatccactct tgtggcctag tggacaactg ggaaagcttg cgacgcagtc gtttttggcg   1620
atccaggcgt agtactagga aataatgtat ctaaacgcaa actccgagct ggaaaaatgt   1680
taccggcgat gcgcggacaa tttagaggcg gcgatcaaga aacacctgct gggcgagcag   1740
tctggagcac agtcttcgat gggcccgaga tcccaccgcg ttcctgggta ccgggacgtg   1800
aggcagcgcg acatccatca aatataccag gcgccaaccg agtgtctcgg aaaacagctt   1860
ctggatatct tccgctggcg gcgcaacgac gaataatagt ccctggaggt gacggaatat   1920
atatgtgtgg agggtaaatc tgacagggtg tagcaaaggt aatattttcc taaaacatgc   1980
aatcggctgc cccgcaacgg gaaaaagaat gactttggca ctcttcacca gagtggggtg   2040
tcccgctcgt gtgtgcaaat aggctcccac tggtcacccc ggattttgca gaaaaacagc   2100
aagttccggg gtgtctcact ggtgtccgcc aataagagga gccggcaggc acggagttta   2160
catcaagctg tctccgatac actcgactac catccgggtc tctcagagag gggaatggca   2220
ctataaatac cgcctccttg cgctctctgc cttcatcaat caaatcatgc tgaggactcg   2280
aattccctag gatgttctct ccaattttgt ccttggaaat tattttagct ttggctactt   2340
tgcaatctgt cttcgctcaa cagtatccgt atgatgtgcc ggattatgcg tctccccagt   2400
acgaagcata tgatgtcaag tctggagtag caggaggagg aatcgcaggc tatcctgggc   2460
cagctggtcc tcctggccca cccggacccc ctggcacatc tggccatcct ggtgcccctg   2520
gcgctccagg ataccaaggt ccccccggtg aacctgggca agctggtccg gcaggtcctc   2580
caggacctcc tggtgctata ggtccatctg gccctgctgg aaaagatggg gaatcaggaa   2640
gacccggacg acctggagag cgaggatttc ctggccctcc tggtatgaaa ggcccagctg   2700
gtatgcctgg attccctggt atgaaaggac acagaggctt tgatggacga aatggagaga   2760
aaggcgaaac tggtgctcct ggattaaagg gggaaaatgg cgttccaggt gaaaatggag   2820
ctcctggacc catgggtcca agaggggctc ccggtgagag aggacggcca ggacttcctg   2880
gagccgcagg ggctcgaggt aatgatggag ctcgaggaag tgatggacaa ccgggccccc   2940
```

```
ctggtcctcc tggaactgca ggattccctg gttcccctgg tgctaagggt gaagttggac   3000
ctgcaggatc tcctggttca agtggcgccc ctggacaaag aggagaacct ggacctcagg   3060
gacatgctgg tgctccaggt cccccctgggc ctcctgggag taatggtagt cctggtggca   3120
aaggtgaaat gggtcctgct ggcattcctg ggctcctgg gctgatagga gctcgtggtc   3180
ctccagggcc acctggcacc aatggtgttc ccgggcaacg aggtgctgca ggtgaacccg   3240
gtaagaatgg agccaaagga gacccaggac cacgtgggga acgcggagaa gctggttctc   3300
caggtatcgc aggacctaag ggtgaagatg gcaaagatgg ttctcctgga gaacctggtg   3360
caaatggact tcctggagct gcaggagaaa ggggtgtgcc tggattccga ggacctgctg   3420
gagcaaatgg ccttccagga gaaaagggtc ctcctgggga ccgtggtggc ccaggccctg   3480
cagggcccag aggtgttgct ggagagcccg gcagagatgg tctccctgga ggtccaggat   3540
tgaggggtat tcctggtagc cccggaggac caggcagtga tgggaaacca gggcctcctg   3600
gaagccaagg agagacgggt cgacccggtc ctccaggttc acctggtccg cgaggccagc   3660
ctggtgtcat gggcttccct ggtcccaaag gaaacgatgg tgctcctgga aaaaatggag   3720
aacgaggtgg ccctggaggt cctggccctc agggtcctgc tggaaagaat ggtgagaccg   3780
gacctcaggg tcctccagga cctactggcc cttctggtga caaaggagac acaggacccc   3840
ctggtccaca aggactacaa ggcttgcctg gaacgagtgg tcccccagga gaaaacggaa   3900
aacctggtga acctggtcca aagggtgagg ctggtgcacc tggaattcca ggaggcaagg   3960
gtgattctgg tgctcccggt gaacgcggac ctcctggagc aggagggccc cctggaccta   4020
gaggtggagc tggcccccct ggtcccgaag gaggaaaggg tgctgctggt cccccctgggc   4080
cacctggttc tgctggtaca cctggtctgc aaggaatgcc tggagaaaga gggggtcctg   4140
gaggccctgg tccaaagggt gataagggtg agcctggcag ctcaggtgtc gatggtgctc   4200
cagggaaaga tggtccacgg ggtcccactg gtcccattgg tcctcctggc ccagctggtc   4260
agcctggaga taagggtgaa agtggtgccc ctggagttcc gggtatagct ggtcctcgcg   4320
gtggccctgg tgagagaggc gaacaggggc ccccaggacc tgctggcttc cctggtgctc   4380
ctggccagaa tggtgagcct ggtgctaaag gagaaagagg cgctcctggt gagaaaggtg   4440
aaggaggccc tcccggagcc gcaggacccg ccggaggttc tgggcctgcc ggtcccccag   4500
gcccccaagg tgtcaaaggc gaacgtggca gtcctggtgg tcctggtgct gctggcttcc   4560
ccggtggtcg tggtcctcct ggccctcctg gcagtaatgg taacccaggc cccccaggct   4620
ccagtggtgc tccaggcaaa gatggtcccc caggtccacc tggcagtaat ggtgctcctg   4680
gcagccccgg gatctctgga ccaaagggtg attctggtcc accaggtgag aggggagcac   4740
ctggccccca gggccctccg ggagctccag gcccactagg aattgcagga cttactggag   4800
cacgaggtct tgcaggccca ccaggcatgc caggtgctag gggcagcccc ggcccacagg   4860
gcatcaaggg tgaaaatggt aaaccaggac ctagtggtca gaatggagaa cgtggtcctc   4920
ctggccccca gggtcttcct ggtctggctg gtacagctgg tgagcctgga agagatggaa   4980
accctggatc agatggtctg ccaggccgag atggagctcc aggtgccaag ggtgaccgtg   5040
gtgaaaatgg ctctcctggt gcccctggag ctcctggtca cccaggccct cctggtcctg   5100
tcggtccagc tggaaagagc ggtgacagag gagaaactgg ccctgctggt ccttctgggg   5160
cccccggtcc tgccggatca agaggtcctc ctggtcccca aggcccacgc ggtgacaaag   5220
gggaaaccgg tgagcgtggt gctatgggca tcaaaggaca tcgcggattc cctggcaacc   5280
```

cagggggcccc cggatctccg ggtcccgctg gtcatcaagg tgcagttggc agtccaggcc 5340
ctgcaggccc cagaggacct gttggaccta gcgggccccc tggaaaggac ggagcaagtg 5400
gacaccctgg tcccattgga ccaccggggc cccgaggtaa cagaggtgaa agaggatctg 5460
agggctcccc aggccaccca ggacaaccag gccctcctgg acctcctggt gcccctggtc 5520
catgttgtgg tgctggcggg gttgctgcca ttgctggtgt tggagccgaa aaagctggtg 5580
gttttgcccc atattatgga gctagcggtt acattcctga agctcctaga gacggacaag 5640
catacgttag aaaggacggt gagtgggtgt tgctgtccac cttcttagct agcgattaca 5700
aggatgacga cgataaggga tcgtgttgcc cgggctgctg tcatcaccat catcaccata 5760
gatcttaagc ggccgcgagt cgtgagtaat caagaggatg tcagaatgcc atttgcctga 5820
gagatgcagg cttcattttt gatacttttt tatttgtaac ctatatagta taggattttt 5880
tttgtcattt tgtttcttct cgtacgagct tgctcctgat cagcctatct cgcagctgat 5940
gaatatcttg tggtaggggt ttgggaaaat cattcgagtt tgatgttttt cttggtattt 6000
cccactcctc ttcagagtac agaagattaa gtgagacgtt cgtttgtgct ccggaggatc 6060
cttcagtaat gtcttgtttc ttttgttgca gtggtgagcc attttgactt cgtgaaagtt 6120
tctttagaat agttgtttcc agaggccaaa cattccaccc gtagtaaagt gcaagcgtag 6180
gaagaccaag actggcataa atcaggtata agtgtcgagc actggcaggt gatcttctga 6240
aagtttctac tagcagataa gatccagtag tcatgcatat ggcaacaatg taccgtgtgg 6300
atctaagaac gcgtcctact aaccttcgca ttcgttggtc cagtttgttg ttatcgatca 6360
acgtgacaag gttgtcgatt ccgcgtaagc atgcataccc aaggacgcct gttgcaattc 6420
caagtgagcc agttccaaca atctttgtaa tattagagca cttcattgtg ttgcgcttga 6480
aagtaaaatg cgaacaaatt aagagataat ctcgaaaccg cgacttcaaa cgccaatatg 6540
atgtgcggca cacaataagc gttcatatcc gctgggtgac tttctcgctt taaaaaatta 6600
tccgaaaaaa ttttctagag tgttgttact ttatacttcc ggctcgtata atacgacaag 6660
gtgtaaggag gactaaacca tggctaaact cacctctgct gttccagtcc tgactgctcg 6720
tgatgttgct ggtgctgttg agttctggac tgataggctc ggtttctccc gtgacttcgt 6780
agaggacgac tttgccggtg ttgtacgtga cgacgttacc ctgttcatct ccgcagttca 6840
ggaccaggtt gtgccagaca acactctggc atgggtatgg gttcgtggtc tggacgaact 6900
gtacgctgag tggtctgagg tcgtgtctac caacttccgt gatgcatctg gtccagctat 6960
gaccgagatc ggtgaacagc cctggggtcg tgagtttgca ctgcgtgatc cagctggtaa 7020
ctgcgtgcat ttcgtcgcag aagagcagga ctaacaattg acaccttacg attatttaga 7080
gagtatttat tagttttatt gtatgtatac ggatgtttta ttatctattt atgcccttat 7140
attctgtaac tatccaaaag tcctatctta tcaagccagc aatctatgtc cgcgaacgtc 7200
aact 7204

<210> SEQ ID NO 20
<211> LENGTH: 6601
<212> TYPE: DNA
<213> ORGANISM: Artificial Sequence
<220> FEATURE:
<223> OTHER INFORMATION: MMV140

<400> SEQUENCE: 20
gatcaaagga tcttcttgag atcctttttt tctgcgcgta atctgctgct tgcaaacaaa 60
aaaaccaccg ctaccagcgg tggtttgttt gccggatcaa gagctaccaa ctctttttcc 120

```
gaaggtaact ggcttcagca gagcgcagat accaaatact gttcttctag tgtagccgta    180
gttaggccac cacttcaaga actctgtagc accgcctaca tacctcgctc tgctaatcct    240
gttaccagtg gctgctgcca gtggcgataa gtcgtgtctt accgggttgg acccaagacg    300
atagttaccg gataaggcgc agcggtcggg ctgaacgggg ggttcgtgca cacagcccag    360
cttggagcga acgacctaca ccgaactgag atacctacag cgtgagctat gagaaagcgc    420
cacgcttccc gaagggagaa aggcggacag gtatccggta agcggcaggg tcggaacagg    480
agagcgcacg agggagcttc caggggggaaa cgcctggtat ctttatagtc ctgtcgggtt    540
tcgccacctc tgacttgagc gtcgattttt gtgatgctcg tcaggggggc ggagcctatg    600
gaaaaacgcc agcaacgcgg cctttttacg gttcctggcc ttttgctggc cttttgctca    660
catgtattta aataatgtat ctaaacgcaa actccgagct ggaaaaatgt taccggcgat    720
gcgcggacaa tttagaggcg gcgatcaaga aacacctgct gggcgagcag tctggagcac    780
agtcttcgat gggcccgaga tcccaccgcg ttcctgggta ccgggacgtg aggcagcgcg    840
acatccatca aatataccag gcgccaaccg agtgtctcgg aaaacagctt ctggatatct    900
tccgctggcg gcgcaacgac gaataatagt ccctggaggt gacggaatat atatgtgtgg    960
agggtaaatc tgacagggtg tagcaaaggt aatattttcc taaaacatgc aatcggctgc   1020
cccgcaacgg gaaaaagaat gactttggca ctcttcacca gagtggggtg tcccgctcgt   1080
gtgtgcaaat aggctcccac tggtcacccc ggattttgca gaaaaacagc aagttccggg   1140
gtgtctcact ggtgtccgcc aataagagga gccggcaggc acggagttta catcaagctg   1200
tctccgatac actcgactac catccgggtc tctcagagag gggaatggca ctataaatac   1260
cgcctccttg cgctctctgc cttcatcaat caaatcatgc tgaggactcg aattccctag   1320
gatgatgagc tttgtgcaaa aggggacctg gttacttttc gctctgcttc atcccactgt   1380
tattttggca caacagtatc cgtatgatgt gccggattat gcgtctcccc agtacgaagc   1440
atatgatgtc aagtctggag tagcaggagg aggaatcgca ggctatcctg ggccagctgg   1500
tcctcctggc ccacccggac cccctggcac atctggccat cctggtgccc ctggcgctcc   1560
aggataccaa ggtccccccg gtgaacctgg gcaagctggt ccggcaggtc ctccaggacc   1620
tcctggtgct ataggtccat ctggccctgc tggaaaagat ggggaatcag gaagacccgg   1680
acgacctgga gagcgaggat ttcctggccc tcctggtatg aaaggcccag ctggtatgcc   1740
tggattccct ggtatgaaag gacacagagg ctttgatgga cgaaatggag agaaaggcga   1800
aactggtgct cctggattaa agggggaaaa tggcgttcca ggtgaaaatg gagctcctgg   1860
acccatgggt ccaagagggg ctcccggtga gagaggacgg ccaggacttc ctggagccgc   1920
aggggctcga ggtaatgatg gagctcgagg aagtgatgga caaccgggcc cccctggtcc   1980
tcctggaact gcaggattcc ctggttcccc tggtgctaag ggtgaagttg gacctgcagg   2040
atctcctggt tcaagtggcg cccctggaca aagaggagaa cctggacctc agggacatgc   2100
tggtgctcca ggtccccctg ggcctcctgg gagtaatggt agtcctggtg gcaaaggtga   2160
aatgggtcct gctggcattc ctggggctcc tgggctgata ggagctcgtg gtcctccagg   2220
gccacctggc accaatggtg ttcccgggca acgaggtgct gcaggtgaac ccggtaagaa   2280
tggagccaaa ggagacccag gaccacgtgg ggaacgcgga gaagctggtt ctccaggtat   2340
cgcaggacct aagggtgaag atggcaaaga tggttctcct ggagaacctg gtgcaaatgg   2400
acttcctgga gctgcaggag aaaggggtgt gcctggattc cgaggacctg ctggagcaaa   2460
```

-continued

```
tggccttcca ggagaaaagg gtcctcctgg ggaccgtggt ggcccaggcc ctgcagggcc   2520
cagaggtgtt gctggagagc ccggcagaga tggtctccct ggaggtccag gattgagggg   2580
tattcctggt agccccggag gaccaggcag tgatgggaaa ccagggcctc ctggaagcca   2640
aggagagacg ggtcgacccg gtcctccagg ttcacctggt ccgcgaggcc agcctggtgt   2700
catgggcttc cctggtccca aaggaaacga tggtgctcct ggaaaaaatg gagaacgagg   2760
tggccctgga ggtcctggcc ctcagggtcc tgctggaaag aatggtgaga ccggacctca   2820
gggtcctcca ggacctactg gcccttctgg tgacaaagga gacacaggac cccctggtcc   2880
acaaggacta caaggcttgc ctggaacgag tggtccccca ggagaaaacg gaaaacctgg   2940
tgaacctggt ccaaagggtg aggctggtgc acctggaatt ccaggaggca agggtgattc   3000
tggtgctccc ggtgaacgcg gacctcctgg agcaggaggg ccccctggac ctagaggtgg   3060
agctggcccc cctggtcccg aaggaggaaa gggtgctgct ggtccccctg ggccacctgg   3120
ttctgctggt acacctggtc tgcaaggaat gcctggagaa agagggggtc ctggaggccc   3180
tggtccaaag ggtgataagg gtgagcctgg cagctcaggt gtcgatggtg ctccagggaa   3240
agatggtcca cggggtccca ctggtcccat tggtcctcct ggcccagctg gtcagcctgg   3300
agataagggt gaaagtggtg cccctggagt tccgggtata gctggtcctc gcggtggccc   3360
tggtgagaga ggcgaacagg ggcccccagg acctgctggc ttccctggtg ctcctggcca   3420
gaatggtgag cctggtgcta aaggagaaag aggcgctcct ggtgagaaag gtgaaggagg   3480
ccctcccgga gccgcaggac ccgccggagg ttctgggcct gccggtcccc caggccccca   3540
aggtgtcaaa ggcgaacgtg gcagtcctgg tggtcctggt gctgctggct tccccggtgg   3600
tcgtggtcct cctggccctc ctggcagtaa tggtaaccca ggccccccag gctccagtgg   3660
tgctccaggc aaagatggtc ccccaggtcc acctggcagt aatggtgctc ctggcagccc   3720
cgggatctct ggaccaaagg gtgattctgg tccaccaggt gagaggggag cacctggccc   3780
ccagggccct ccgggagctc caggcccact aggaattgca ggacttactg gagcacgagg   3840
tcttgcaggc ccaccaggca tgccaggtgc taggggcagc ccggcccac agggcatcaa   3900
gggtgaaaat ggtaaaccag gacctagtgg tcagaatgga gaacgtggtc ctcctggccc   3960
ccagggtctt cctggtctgg ctggtacagc tggtgagcct ggaagagatg gaaaccctgg   4020
atcagatggt ctgccaggcc gagatggagc tccaggtgcc aagggtgacc gtggtgaaaa   4080
tggctctcct ggtgcccctg gagctcctgg tcacccaggc cctcctggtc ctgtcggtcc   4140
agctggaaag agcggtgaca gaggagaaac tggccctgct ggtccttctg ggcccccgg   4200
tcctgccgga tcaagaggtc ctcctggtcc ccaaggccca cgcggtgaca aaggggaaac   4260
cggtgagcgt ggtgctatgg gcatcaaagg acatcgcgga ttccctggca acccaggggc   4320
ccccggatct ccgggtcccg ctggtcatca aggtgcagtt ggcagtccag gccctgcagg   4380
ccccagagga cctgttggac ctagcgggcc ccctggaaag gacggagcaa gtggacaccc   4440
tggtcccatt ggaccaccgg ggccccgagg taacagaggt gaaagaggat ctgagggctc   4500
cccaggccac ccaggacaac caggccctcc tggacctcct ggtgcccctg gtccatgttg   4560
tggtgctggc ggggttgctg ccattgctgg tgttggagcc gaaaaagctg gtggttttgc   4620
cccatattat ggagctagcg gttacattcc tgaagctcct agagacggac aagcatacgt   4680
tagaaaggac ggtgagtggg tgttgctgtc caccttctta gctagcgatt acaaggatga   4740
cgacgataag ggatcgtgtt gcccgggctg ctgtcatcac catcatcacc atagatctta   4800
agcggccgcg agtcgtgagt aatcaagagg atgtcagaat gccatttgcc tgagagatgc   4860
```

```
aggcttcatt tttgatactt ttttatttgt aacctatata gtataggatt ttttttgtca   4920

ttttgtttct tctcgtacga gcttgctcct gatcagccta tctcgcagct gatgaatatc   4980

ttgtggtagg ggtttgggaa aatcattcga gtttgatgtt tttcttggta tttcccactc   5040

ctcttcagag tacagaagat taagtgagac gttcgtttgt gctccggagg atccttcagt   5100

aatgtcttgt ttcttttgtt gcagtggtga gccattttga cttcgtgaaa gtttctttag   5160

aatagttgtt tccagaggcc aaacattcca cccgtagtaa agtgcaagcg taggaagacc   5220

aagactggca taaatcaggt ataagtgtcg agcactggca ggtgatcttc tgaaagtttc   5280

tactagcaga taagatccag tagtcatgca tatggcaaca atgtaccgtg tggatctaag   5340

aacgcgtcct actaaccttc gcattcgttg gtccagtttg ttgttatcga tcaacgtgac   5400

aaggttgtcg attccgcgta agcatgcata cccaaggacg cctgttgcaa ttccaagtga   5460

gccagttcca acaatctttg taatattaga gcacttcatt gtgttgcgct tgaaagtaaa   5520

atgcgaacaa attaagagat aatctcgaaa ccgcgacttc aaacgccaat atgatgtgcg   5580

gcacacaata agcgttcata tccgctgggt gactttctcg ctttaaaaaa ttatccgaaa   5640

aaattttcta gagtgttgtt actttatact tccggctcgt ataatacgac aaggtgtaag   5700

gaggactaaa ccatggctaa actcacctct gctgttccag tcctgactgc tcgtgatgtt   5760

gctggtgctg ttgagttctg gactgatagg ctcggtttct cccgtgactt cgtagaggac   5820

gactttgccg gtgttgtacg tgacgacgtt accctgttca tctccgcagt tcaggaccag   5880

gttgtgccag acaacactct ggcatgggta tgggttcgtg gtctggacga actgtacgct   5940

gagtggtctg aggtcgtgtc taccaacttc cgtgatgcat ctggtccagc tatgaccgag   6000

atcggtgaac agccctgggg tcgtgagttt gcactgcgtg atccagctgg taactgcgtg   6060

catttcgtcg cagaagagca ggactaacaa ttgacacctt acgattattt agagagtatt   6120

tattagtttt attgtatgta tacggatgtt ttattatcta tttatgccct tatattctgt   6180

aactatccaa aagtcctatc ttatcaagcc agcaatctat gtccgcgaac gtcaactaaa   6240

aataagcttt ttatgctctt ctctcttttt ttcccttcgg tataattata ccttgcatcc   6300

acagattctc ctgccaaatt ttgcataatc ctttacaaca tggctatatg ggagcactta   6360

gcgccctcca aaacccatat tgcctacgca tgtataggtg tttttccac aatattttct   6420

ctgtgctctc tttttattaa agagaagctc tatatcggag aagcttctgt ggccgttata   6480

ttcggcctta tcgtgggacc acattgcctg aattggtttg ccccggaaga ttggggaaac   6540

ttggatctga ttaccttagc tgcagaaaag ggtaccactg agcgtcagac cccgtagaaa   6600

a                                                                  6601
```

```
<210> SEQ ID NO 21
<211> LENGTH: 57
<212> TYPE: DNA
<213> ORGANISM: Artificial Sequence
<220> FEATURE:
<223> OTHER INFORMATION: alpha-factor Pre

<400> SEQUENCE: 21

atgagattcc catctatttt caccgctgtc ttgttcgctg cctcctctgc attggct     57


<210> SEQ ID NO 22
<211> LENGTH: 267
<212> TYPE: DNA
<213> ORGANISM: Artificial Sequence
<220> FEATURE:
```

-continued

<223> OTHER INFORMATION: Alpha-factor Pre pro

<400> SEQUENCE: 22
atgagattcc catctatttt caccgctgtc ttgttcgctg cctcctctgc attggctgcc 60
cctgttaaca ctaccactga agacgagact gctcaaattc cagctgaagc agttatcggt 120
tactctgacc ttgagggtga tttcgacgtc gctgttttgc ctttctctaa ctccactaac 180
aacggtttgt tgttcattaa caccactatc gcttccattg ctgctaagga agagggtgtc 240
tctctcgaga aaagagaggc cgaagct 267

<210> SEQ ID NO 23
<211> LENGTH: 1298
<212> TYPE: DNA
<213> ORGANISM: Artificial Sequence
<220> FEATURE:
<223> OTHER INFORMATION: pGCW14-GAP1 bidirectional promoter

<400> SEQUENCE: 23
ttttgttgtt gagtgaagcg agtgacggaa cggtaaaatg taagtaacaa aagaaaaaga 60
gaaccagggg ggggaggaga gtatgtattt ataccgtacg gcaccaggcg aaaagctata 120
aacaaacctt tttcgcggta tatttgttta tatttcctat tttaaactca aaatctgccc 180
taatctggac ttttcatgca aagttatgca cctgaggcag gaatgaagca ggctcgacga 240
cgaaaaggct ggaatgggta actatggatc gattgatttg tctgttgaaa tcttgatttg 300
gcactcgttt aaattaacat tctgcatcat ggtgaattgc ggtcacaggt actggttttt 360
cctgaagctc taggcggtgt tactgttccc acaacttaaa acctaaaaga ggtgggtgct 420
tctttgcgtg ggtgaccaaa aataaaaccg actgcctagt ggcattgata cctttttttg 480
ggtgttgtcc tggaaaccac tgaacgtatc tgcgagatac aaaagtattt ttagataagt 540
ggcaaatgca aaaaatctga ttggtcagtt aatgattgat gaacgacttt aaggttaaaa 600
agcaaaatag tgactgctgc catgtgcctg tatagcacat gaactgatta ttctgttccc 660
acgctacgat gaaaacgcct tctctgccga aagattaaag ctgcgcggga aaaaaaaatt 720
aactttacgg ggcgagcacg gttccccgaa acaaaagatg gttggctttc acccagcgag 780
ctcactggat cccagttaaa aatagttagg tgggttcacc tgtttttgta gaaatgtctt 840
ggtgtcctcg accaatcagg tagccatccc tgaaatacct ggctccgtgg caacaccgaa 900
cgacctgctg gcaacgttaa attctccggg gtaaaactta aatgtggagt aatagaacca 960
gaaacgtctc ttcccttctc tctccttcca ccgcccgtta ccgtccctag gaaattttac 1020
tctgctggag agcttcttct acggccccct tgcagcaatg ctcttcccag cattacgttg 1080
cgggtaaaac ggaggtcgtg tacccgacct agcagcccag ggatggaaag tcccggccgt 1140
cgctggcaat aactgcgggc ggacgcatgt cttgagatta ttggaaacca ccagaatcga 1200
atataaaagg cgaacacctt tcccaatttt ggtttctcct gacccaaaga ctttaaattt 1260
aatttatttg tccctatttc aatcaattga acaactat 1298

<210> SEQ ID NO 24
<211> LENGTH: 1251
<212> TYPE: DNA
<213> ORGANISM: Artificial Sequence
<220> FEATURE:
<223> OTHER INFORMATION: Das1-Das2 bi-directional promoter

<400> SEQUENCE: 24
ttttgatgtt tgatagtttg ataagagtga actttagtgt ttagaggggt tataatttgt 60

```
tgtaactggt tttggtctta agttaaaacg aacttgttat attaaacaca acggtcactc    120

aggatacaag aataggaaag aaaaacttta aactggggac atgttgtctt tatataattt    180

ggcggttaac ccttaatgcc cgtttccgtc tcttcatgat aacaaagctg cccatctatg    240

actgaatgtg gagaagtatc ggaacaaccc ttcactaagg atatctaggc taaactcatt    300

cgcgccttag atttctccaa ggtatcggtt aagtttcctc tttcgtactg gctaacgatg    360

gtgttgctca acaaagggat ggaacggcag ctaaagggag tgcatggaat gactttaatt    420

ggctgagaaa gtgttctatt tgtccgaatt tcttttttct attatctgtt cgtttgggcg    480

gatctctcca gtgggggta aatggaagat ttctgttcat ggggtaagga agctgaaatc    540

cttcgtttct tataggggca agtatactaa atctcggaac attgaatggg gtttactttc    600

attggctaca gaaattatta agtttgttat ggggtgaagt taccagtaat tttcattttt    660

tcacttcaac ttttggggta tttctgtggg gtagcataga gcaatgatat aaacaacaat    720

tgagtgacag gtctactttg ttctcaaaag gccataacca tctgtttgca tctcttatca    780

ccacaccatc ctcctcatct ggccttcaat tgtggggaac aactagcatc ccaacaccag    840

actaactcca cccagatgaa accagttgtc gcttaccagt caatgaatgt tgagctaacg    900

ttccttgaaa ctcgaatgat cccagccttg ctgcgtatca tccctccgct attccgccgc    960

ttgctccaac catgtttccg cctttttcga acaagttcaa atacctatct ttggcaggac   1020

ttttcctcct gcctttttta gcctcagctc tcggttagcc tctaggcaaa ttctggtctt   1080

catacctata tcaacttttc atcagatagc ctttgggttc aaaaaagaac taaagcagga   1140

tgcctgatat ataaatccca gatgatctgc ttttgaaact attttcagta tcttgattcg   1200

tttacttaca aacaactatt gttgatttta tctggagaat aatcgaacaa a            1251
```

```
<210> SEQ ID NO 25
<211> LENGTH: 550
<212> TYPE: DNA
<213> ORGANISM: Artificial Sequence
<220> FEATURE:
<223> OTHER INFORMATION: pHTX1 bi-directional promoter

<400> SEQUENCE: 25

tgttgtagtt ttaatatagt ttgagtatga gatggaactc agaacgaagg aattatcacc     60

agtttatata ttctgaggaa agggtgtgtc ctaaattgga cagtcacgat ggcaataaac    120

gctcagccaa tcagaatgca ggagccataa attgttgtat tattgctgca agatttatgt    180

gggttcacat tccactgaat ggttttcact gtagaattgg tgtcctagtt gttatgtttc    240

gagatgtttt caagaaaaac taaaatgcac aaactgacca ataatgtgcc gtcgcgcttg    300

gtacaaacgt caggattgcc accacttttt tcgcactctg gtacaaaagt tcgcacttcc    360

cactcgtatg taacgaaaaa cagagcagtc tatccagaac gagacaaatt agcgcgtact    420

gtcccattcc ataaggtatc ataggaaacg agagtcctcc ccccatcacg tatatataaa    480

cacactgata tcccacatcc gcttgtcacc aaactaatac atccagttca agttacctaa    540

acaaatcaaa                                                           550
```